United States Patent
Ichelmann et al.

(10) Patent No.: US 12,329,421 B2
(45) Date of Patent: Jun. 17, 2025

(54) ROTATING ROD CONNECTORS FOR SPINE STABILIZATION

(71) Applicant: ZIMMER BIOMET SPINE, INC., Westminster, CO (US)

(72) Inventors: Bruno Ichelmann, Limoges (FR); David Rigotto, Saint Selve (FR); Nicolas Roche, Saint Medard en Jalles (FR); Nicolas Bidegaimberry, Gradignan (FR)

(73) Assignee: Zimmer Biomet Spine, Inc., Westminster, CO (US)

( * ) Notice: Subject to any disclaimer, the term of this patent is extended or adjusted under 35 U.S.C. 154(b) by 0 days.

(21) Appl. No.: 18/091,217

(22) Filed: Dec. 29, 2022

(65) Prior Publication Data

US 2023/0200860 A1 Jun. 29, 2023

Related U.S. Application Data

(60) Provisional application No. 63/294,745, filed on Dec. 29, 2021.

(51) Int. Cl.
*A61B 17/70* (2006.01)
(52) U.S. Cl.
CPC ................. *A61B 17/7037* (2013.01)
(58) Field of Classification Search
CPC .............. A61B 17/7049; A61B 17/705; A61B 17/7052; A61B 17/7041
See application file for complete search history.

(56) References Cited

U.S. PATENT DOCUMENTS

| 8,147,519 | B2 | 4/2012 | Wilcox |
| 8,236,028 | B2* | 8/2012 | Kalfas ................ A61B 17/7049 |
| | | | 606/246 |

(Continued)

FOREIGN PATENT DOCUMENTS

CN 109998657 7/2019

OTHER PUBLICATIONS

Official Action for Great Britain Patent Application No. 2219883.2, dated Jun. 19, 2023 9 pages.
(Continued)

*Primary Examiner* — Ellen C Hammond
*Assistant Examiner* — Holly Joanna Lane
(74) *Attorney, Agent, or Firm* — Sheridan Ross P.C.

(57) ABSTRACT

A pivoting rod connector for spinal stabilization members comprises first and second connector blocks, each comprising a rod slot for receiving a stabilization member and a closure bore for receiving a closure device, a pivot mechanism connecting the first connector block and the second connector block to allow for angulation between the rod slots, and a locking mechanism to inhibit angulation of the pivot mechanism. Methods of connecting stabilization members in a spinal procedure can comprise adjusting of the angular positioning of the first connector block relative to the second connector block via the pivot mechanism, and locking a position of the first connector body relative to the second connector block following adjustment. The positioning of the connector blocks relative to the spine of the patient are adjustable when the stabilization members are coupled to the spine and inserted into the connector blocks.

20 Claims, 17 Drawing Sheets

(56) References Cited

U.S. PATENT DOCUMENTS

| | | | |
|---|---|---|---|
| 9,931,140 B2* | 4/2018 | Akbarnia | A61B 17/705 |
| 10,105,163 B2* | 10/2018 | Keyer | A61B 17/705 |
| 10,405,892 B2* | 9/2019 | Harvey | A61B 17/7049 |
| 10,610,268 B2 | 4/2020 | Barry et al. | |
| 11,426,211 B2* | 8/2022 | Kim | A61B 17/7032 |
| 2004/0133203 A1* | 7/2004 | Young | A61B 17/7052 |
| | | | 606/252 |
| 2008/0015588 A1* | 1/2008 | Hawkes | A61B 17/7052 |
| | | | 606/64 |
| 2017/0280063 A1* | 9/2017 | Jeon | G06V 20/56 |
| 2017/0281245 A1 | 10/2017 | Murray et al. | |
| 2018/0280062 A1* | 10/2018 | Lee | A61B 17/7052 |
| 2018/0280063 A1 | 10/2018 | Lee et al. | |

OTHER PUBLICATIONS

Official Action for United Kingdom Patent Application No. GB2219883.2, dated Feb. 28, 2024 5 pages.

* cited by examiner

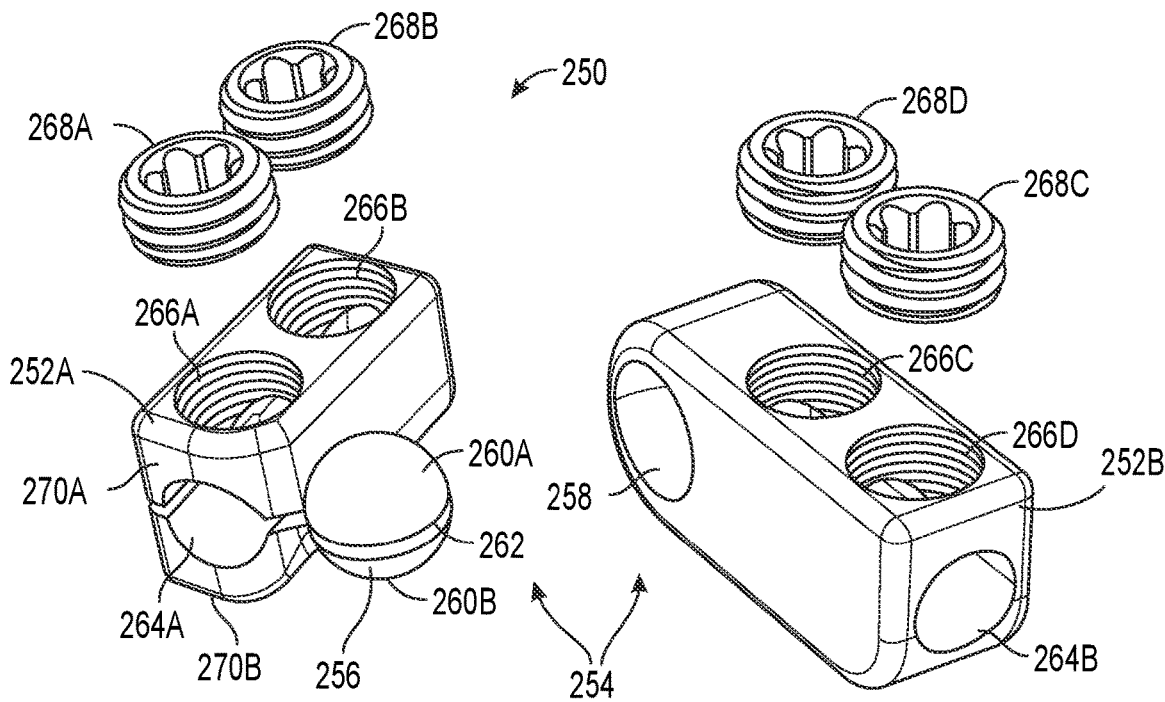
FIG. 21
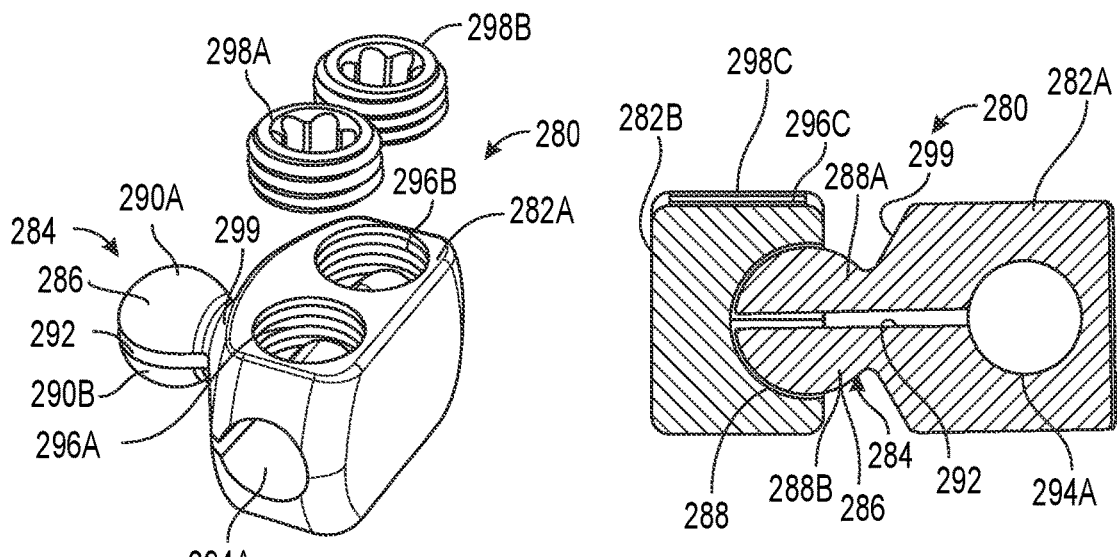
FIG. 22A
FIG. 22B

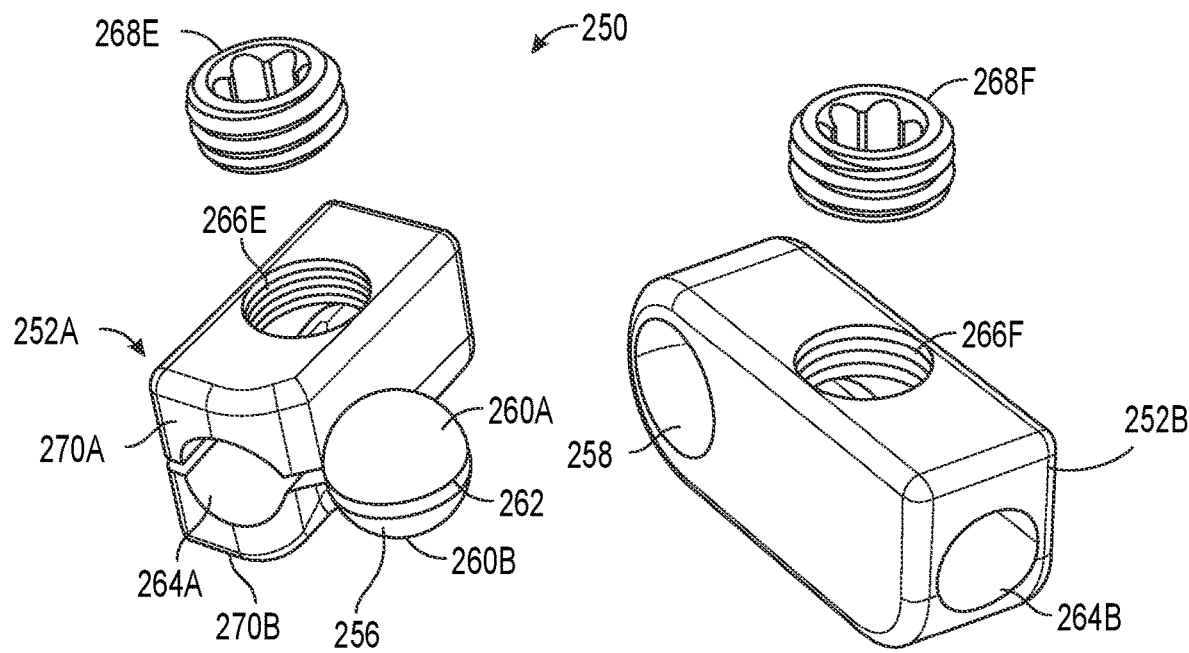
FIG.23
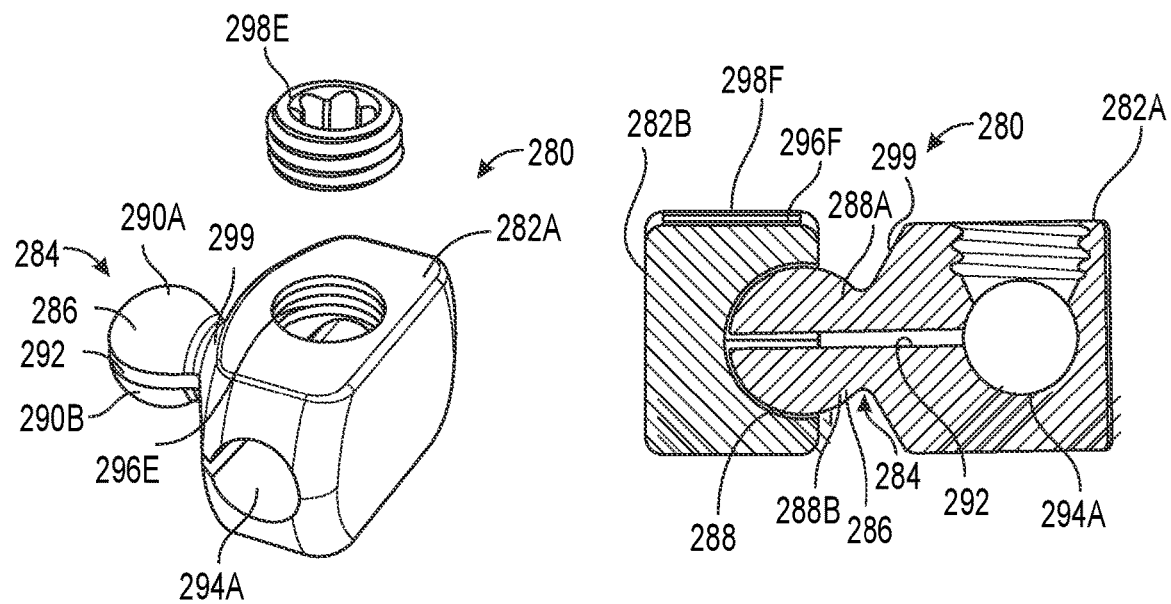
FIG. 24A
FIG. 24B

ROTATING ROD CONNECTORS FOR SPINE STABILIZATION

CROSS-REFERENCE TO RELATED APPLICATION

This U.S. Non-Provisional patent application claims the benefit of priority under 35 U.S.C. § 119(e) of U.S. Provisional Patent Application Ser. No. 63/294,745, filed Dec. 29, 2021, the entire disclosure of each of which is hereby incorporated by reference.

TECHNICAL FIELD

The present disclosure pertains generally, but not by way of limitation, to devices used in spinal stabilization procedures, such as those using elongate stabilization members including rigid rods. More specifically, but not by way of limitation, the present disclosure relates to devices that can be used to connect spinal stabilization members.

BACKGROUND

Elongate stabilization members can be used in various surgical procedures to provide support to adjacent bones. The elongate stabilization members can be attached to the bones using fixation devices that can be implanted directly to the bones. In spinal procedures, pedicle screws or bone anchors can be implanted into a plurality of vertebrae of a spinal column and then each pedicle screw or bone anchor can be attached to an elongate stabilization member to support the spinal column. Some surgical procedures can involve the use of multiple rods, and/or revision surgeries can involve the extension of a previously implanted construct with additional rods. Various systems and methods have been developed for interconnecting multiple rods during a surgical procedure, including systems and methods for interconnecting multiple rods in an end-to-end or parallel configuration. While placing and interconnecting multiple rods using a connector during a surgical procedure, it can be desirable to adjust a distance between the rods and a distance between the connector and the rods. Additionally, it can be desirable to have a connector that can be coupled with curved rods, to adequately match patient anatomy.

Examples of spinal rod connectors are described in U.S. Pat. No. 8,236,028 to Kalfas et al.; U.S. Pat. No. 8,147,519 to Wilcox; U.S. Pat. No. 9,931,140 to Akbarnia et al.; and U.S. Pat. No. 10,610,268 to Barry et al.

SUMMARY

Aspects of the present disclosure are directed to solving problems in spinal procedures involving elongate stabilization members can include the difficulty of aligning connectors with adjacent components and anatomy. For example, a first rod can extend along a first portion of a spinal column along a first axis, and it can be desirable to place a second rod along a different portion of the spinal column that extends along a second axis due to curvature of the spinal column. Rigid rods can be curved or bent by the surgeon to provide the desired alignment. Furthermore, use of adjustable rod connectors can alleviate some of the difficulties in aligning ends of adjacent rods. However, it can be difficult to simultaneously align the angular position between rods being connected as well as maintain the rods in a desired axial position while the stabilization members or rods, pedicle screws or bone anchors, and other components are being locked into position.

The present subject matter can help provide solutions to these problems and other problems, such as by providing adjustable connectors for elongate stabilization members including rigid rods. For example, the adjustable connectors of the present disclosure can simultaneously lock the axial and angular position of a first rod relative to a second rod, such as an already implanted and fixated rod. The adjustable connectors of the present disclosure can additionally be configured to allow for adjustment of connected rods in multiple planes. Furthermore, the adjustable connectors of the present disclosure can provide easy access to adjusters for locking the adjustable connectors in place. Furthermore, the adjustable connector of the present disclosure can provide the ability to adjust (e.g., increase or decrease) the total length of the stabilization member/pivoting rod connector system through distraction of the pivoting rod connectors, without needing to uninstall and reinstall/disengage and re-engage the components (e.g., pedicle screws or bone anchors, stabilization members or rods, and the like) in the patient.

In an example, a pivoting rod connector for spinal stabilization members can comprise a first connector block, a second connector block, and a pivot mechanism connecting the first connector block and the second connector block. The first connector block comprises a first rod slot for receiving a first stabilization member and a first closure bore for receiving a first closure device. Engaging the first stabilization member with the first closure device secures the first stabilization member within the first rod slot. The second connector block comprises a second rod slot for receiving a second stabilization member and a second closure bore for receiving a second closure device. Engaging the second stabilization member with the second closure device secures the second stabilization member within the second rod slot. The pivot mechanism is configured to allow for angulation between the first rod slot and the second rod slot. The pivoting rod connector is lockable to inhibit angulation of the pivot mechanism.

In another example, a method of connecting stabilization members in a spinal procedure can include, but is not limited to, securing a first stabilization member in a first connector block by engaging the first stabilization member inserted in a first rod slot of the first connector block with a first closure device inserted in a first closure bore of the first connector block. The method can include, but is not limited to, securing a second stabilization member to a second connector block by engaging the second stabilization member inserted in a second rod slot of the second connector block with a second closure device inserted in a second closure bore of the second connector block. The method can include, but is not limited to, adjusting a pivot mechanism connecting the first connector block and the second connector block to adjust an angular position between the first stabilization member and the second stabilization member. The method can include, but is not limited to, locking the pivot mechanism to inhibit angulation between the first stabilization member and the second stabilization member.

In another example, a pivoting rod connector for spinal stabilization members, the pivoting rod connector can comprise a first stabilization member, a second stabilization member, and a pivoting rod connector. The pivoting rod connector can comprise a first connector block, a second connector block, and a pivot mechanism connecting the first connector block and the second connector block. The first connector block can comprise a first rod slot for receiving a first end of the first stabilization member, and a first closure bore for receiving a first closure device, wherein engaging the first end of the first stabilization member with the first closure device secures the first stabilization member within the first rod slot. The second connector block can comprise a second rod slot for receiving a second end of a second stabilization member, and a second closure bore for receiving a second closure device, wherein engaging the second end of the second stabilization member with the second closure device secures the second stabilization member within the second rod slot. The pivot mechanism is configured to allow for angulation between the first rod slot and the second rod slot, and wherein the pivoting rod connector is lockable to inhibit angulation of the pivot mechanism.

In another example, a pivoting rod connector for spinal stabilization members can comprise a first connector body comprising a first rod slot for receiving a first stabilization member and a first closure bore for receiving a closure device. The pivoting rod connector can comprise a second connector body comprising a second rod slot for receiving a second stabilization member and a second closure bore for receiving a closure device. The pivoting rod connector can comprise a pivot mechanism connecting the first connector body and the second connector body to allow for angulation between the first and second rod slots. The pivoting rod connector can comprise a locking mechanism to inhibit angulation of the pivot mechanism. The locking mechanism is operable via insertion of a closure device in at least one of the closure bores to secure a corresponding stabilization member therein.

In another example, a method of connecting stabilization members in a spinal procedure may include, but is not limited to, connecting a first connector body to a first stabilization member. The method may include, but is not limited to, connecting a second connector body to a second stabilization member. The method may include, but is not limited to, adjusting a pivot mechanism connecting the first connector body and the second connector body to adjust an angular position between the first stabilization member and the second stabilization member. The method may include, but is not limited to, adjusting a closure device to simultaneously lock the first stabilization member in the first connector body and lock a position of the first connector body relative to the second connector body.

In an additional example, a pivoting rod connector for spinal stabilization members can comprise a first connector body comprising a first rod slot for receiving a first stabilization member and a first closure bore for receiving a closure device. The pivoting rod connector can comprise a second connector body comprising a second rod slot for receiving a second stabilization member and a second closure bore for receiving a closure device. The pivoting rod connector can comprise a pivot mechanism connecting the first connector body and the second connector body to allow for angulation between the first and second rod slots. The pivot mechanism can comprise a pivot ball extending from the first connector body and a pivot socket or ball socket positioned on the second connector body, where the ball socket may be configured to receive the pivot ball to allow multi-planar angulation between the first and second connector bodies. The pivoting rod connector can comprise a locking mechanism to inhibit angulation of the pivot mechanism. The locking mechanism can comprise an expansion slot in the pivot ball to split the pivot ball into deflectable portions and a fastener configured to be threaded into the first connector body to push the deflectable portions apart.

In a further example, a method of connecting stabilization members in a spinal procedure may include, but is not limited to, connecting a first connector body to a first stabilization member. The method may include, but is not limited to, connecting a second connector body to a second stabilization member. The method may include, but is not limited to, adjusting a ball and socket pivot mechanism connecting the first connector body and the second connector body to adjust a multi-angular position between the first stabilization member and the second stabilization member. The method may include, but is not limited to, expanding a ball of the ball and socket pivot mechanism within a socket of the ball and socket pivot mechanism to lock the ball and socket pivot mechanism.

This Summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood the drawings are not necessarily drawn to scale. In certain instances, details that are not necessary for an understanding of the disclosure or that render other details difficult to perceive may have been omitted. In addition, it should be understood that the disclosure is not necessarily limited to the particular embodiments illustrated herein. Further, it should be understood like numerals may describe similar components in different views. Like numerals having different letter suffixes may represent different instances of similar components. The drawings illustrate generally, by way of example, but not by way of limitation, various embodiments discussed in the present document.

FIG. 21 is an exploded view of a second example or variation of FIG. 17 of a pivoting rod connector connected by a swivel locking system wherein the ball connector and ball socket can be offset to a side of each connector block.

FIG. 22A is an exploded view of a third example or variation of FIG. 17 of a pivoting rod connector connected by a swivel locking system wherein the ball connector is centered on a connector block and the ball socket is off-center on a connector block.

FIG. 22B is a cross-sectional view of the pivoting rod connector of FIG. 22A taken to show a slot extending through the ball connector.

FIG. 23 is an exploded view of a second example or variation of FIG. 21 of a pivoting rod connector connected by a swivel locking system wherein the ball connector and ball socket can be offset to a side of each connector block.

FIG. 24A is an exploded view of a second example or variation of FIG. 22A of a pivoting rod connector connected by a swivel locking system wherein the ball connector is centered on a connector block and the ball socket is off-center on a connector block.

FIG. 24B is a cross-sectional view of the pivoting rod connector of FIG. 24A taken to show a slot extending through the ball connector.

Figure 1:
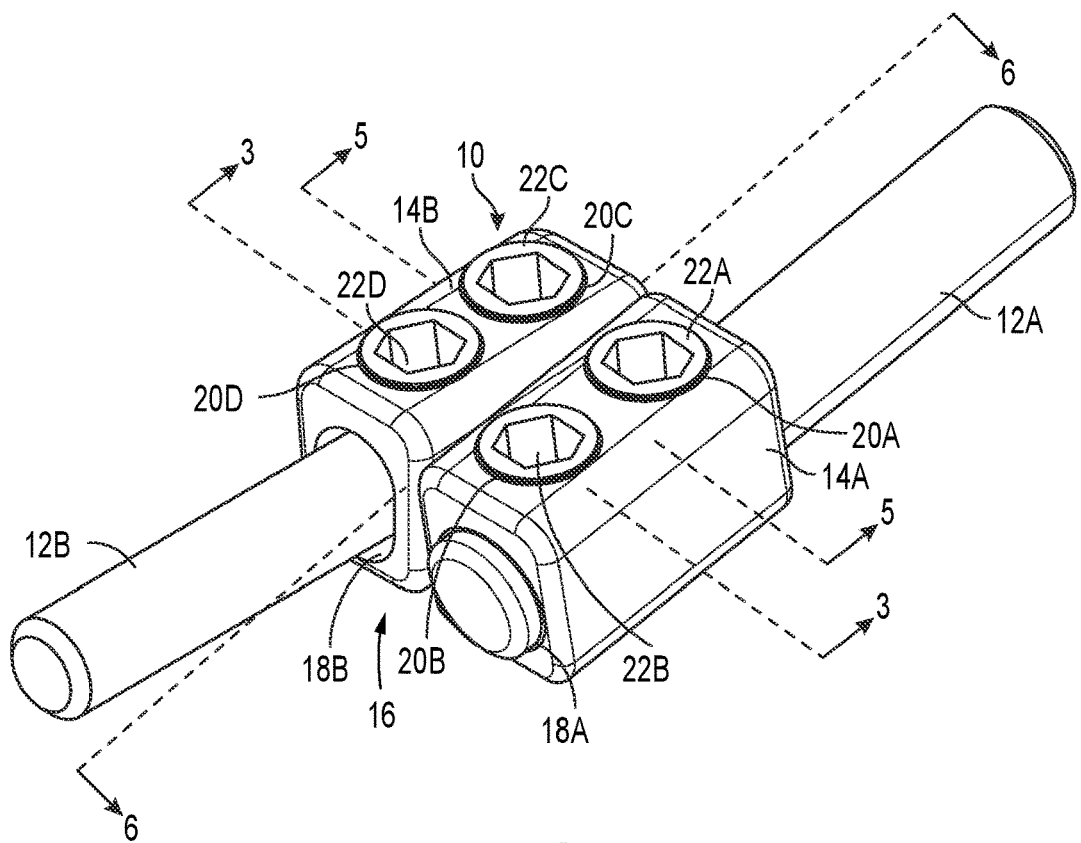
FIG. 1 is a perspective view of a pivoting rod connector coupling a pair of elongate stabilization members using connector blocks connected by a wedged locking system.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The ensuing description provides embodiments only, and is not intended to limit the scope, applicability, or configuration of the claims. Rather, the ensuing description will provide those skilled in the art with an enabling description for implementing the described embodiments. It being understood that various changes may be made in the function and arrangement of elements without departing from the spirit and scope of the appended claims.

Various aspects of the present disclosure will be described herein with reference to drawings that may be schematic illustrations of idealized configurations.

The present disclosure is directed to pivoting rod connectors for spine stabilization. The pivoting rod connectors discussed below can be used to couple stabilization members (or stabilizing rods) together. The pivoting rod connectors operable to receive the stabilization members may include one or more components to lock the stabilization members within the rod connectors and/or at desired angles. The stabilization members may be positioned in different axes along the spine or in the same axis. The stabilization members may be installed separately, with the pivoting rod connector couplable to an installed or fixed first stabilizing rod and then a second stabilizing rod be installed to extend the total length of a stabilization member/pivoting rod connector system. The present disclosure is also directed to various locking mechanisms for use to lock the stabilization members within the rod connectors and/or lock the rod connectors at a particular angle.

The pivoting rod connectors of the present disclosure may be provided as part of a fixation system that also includes implants that are installable within spinal vertebrae (e.g., bone anchors 2, as illustrated in FIGS. 7, 15, 30, 31), connecting rods or stabilization members of various length, and/or any instruments for the surgical procedure being performed. For example, the instruments can include tools for pedicle targeting, pedicle preparation, screw insertion, rod and closure top insertion, and manipulation. Manipulation tools include rod reduction instruments, such as rod rockers and reducers, or distractors. Commercial examples of fixation systems provided by ZimVie include the Vital™ Spinal Fixation System, the Tether™ Vertebral Body Tethering System, and the Polaris™ Spinal Deformity Correction System. Details regarding how the rod connectors of the present disclosure connect with other components of the various fixation systems are not discussed in detail, except as needed under the features and aspects of the present disclosure discussed herein. It is noted the illustrations of the bone anchors 2 are provided for exemplary purposes only, and are not intended to be limiting as to the form or design of the bone anchors 2.

It is noted that "pivoting" and "rotating" as used throughout the disclosure may be considered a same or similar motions, without departing from the scope of the present disclosure. For example, "rotating" and/or "pivoting" may refer to a single-axis or single-planar actuation, and/or may refer to a multi-axis or multi-planar actuation including the aforementioned single-axis or single-planar actuation.

FIGS. 1-8 in general illustrate a pivoting rod connector 10, in accordance with one or more embodiments of the present disclosure. It is noted aspects and/or components of the pivoting rod connector 10 may be shared with and/or combinable with one or more aspects and/or components of pivoting rod connectors 100, 200, 250, 280, 300, 350, 360, 370 without departing from the scope of the present disclosure, unless otherwise noted.

FIG. 1 is a perspective view of the pivoting rod connector 10 coupling a first elongate stabilization member 12A and a second elongate stabilization member 12B using a first connector block 14A and a second connector block 14B, in accordance with embodiments of the present disclosure. The pivoting rod connector 10 includes the first connector block 14A and the second connector block 14B. The connector blocks 14A, 14B are linked by a wedged locking system 16. It is noted the wedged locking system 16 may be considered a pivot mechanism, for purposes of the present disclosure. The first connector block 14A includes a rod slot 18A and the second connector block 14B includes a rod slot 18B.

In some embodiments, the first connector block 14A may include a closure bore 20A and/or a closure bore 20B. The closure bore 20A and/or the closure bore 20B may be operable to receive a closure device 22A or a closure device 22B, respectively. In additional embodiments, the second connector block 14B may include a closure bore 20C and/or a closure bore 20D. For instance, the closure bore 20C and/or the closure bore 20D may be operable to receive a closure device 22C and/or a closure device 22D, respectively. The closure devices 22A-22D may be configured to engage the closure bores 20A-20D. For example, as discussed in detail herein, the closure bores 20A-20D may include threading that is complementary to threading on the closure devices 22A-22D.

In some examples, the elongate stabilization members 12A and 12B can include rigid rods or members. However, in other examples, the elongate stabilization members 12A and 12B can include other components including, but not limited to, flexible cords or members.

The pivoting rod connector 10 can be configured to hold the first and second elongate stabilization members 12A and 12B in a fixed angular relationship. The first and second elongate stabilization members 12A and 12B can be inserted into the rod slots 18A and 18B, respectively, and held therein via the closure devices 22A-22D. The closure devices 22A-22D can be inserted into the closure bores 20A-20D to axially lock the positions of the elongate stabilization members 12A and 12B relative to the connector blocks 14A and 14B, respectively. Simultaneously, the closure devices 22C and/or 22D can push the elongate stabilization member 12B downward within rod slot 18B to push the elongate stabilization member 12B laterally into engagement with the connector block 14A, thereby locking the angular position between the connector blocks 14A and 14B. In this regard, at least the closure bore 20C and the closure device 22C, and/or the closure bore 20D and the closure device 22D may be considered a single locking mechanism for both the stabilization member 12B and for the pivoting or angulation of the pivoting rod connector 10.

Figure 2:
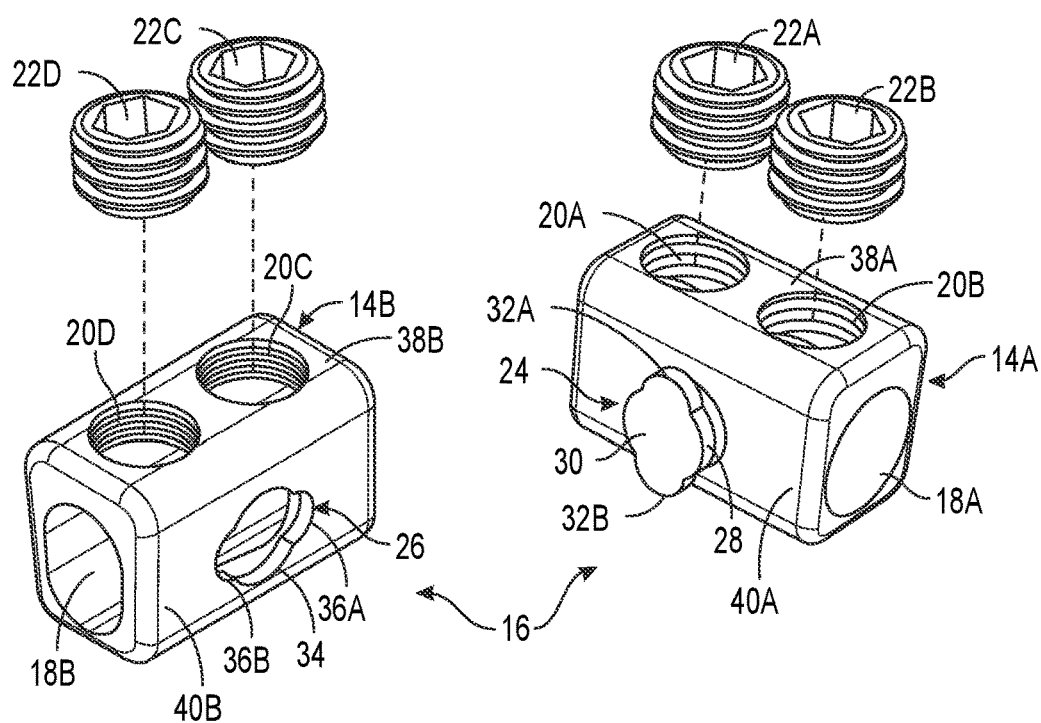
FIG. 2 is an exploded view of the pivoting rod connector of FIG. 1 showing a pair of connector blocks couplable via a wedged pivot pin of the wedged locking system.

FIG. 2 is an exploded view of pivoting rod connector 10 of FIG. 1 showing the connector blocks 14A and 14B couplable via a wedged pivot pin 24 and a pivot socket 26, in accordance with embodiments of the present disclosure. In some embodiments, at least the wedged pivot pin 24 and the pivot socket 26 form the wedged locking system 16. The wedged pivot pin 24 can include a pivot post including an extension 28 with a wedge face 30 and protruding lobes 32A and 32B. The pivot socket 26 can include an opening 34 with recessed lobes 36A and 36B. It is noted, however, that the pivot pin 24 and the pivot socket 26 are not limited to the lobed shapes in FIG. 2, and may be a different set of corresponding, interlocking shapes without departing from the scope of the present disclosure.

The connector block 14A can include a rectangular body having an upper surface 38A and a side surface 40A. The upper surface 38A can include the closure bores 20A and 20B. The extension 28 can extend from the side surface 40A. The rod slot 18A can have an aperture within a front surface of the connector block 14A. In some embodiments, the rod slot 18A may extend from the front surface of the connector block 14A and exit through an aperture in a rear surface of the connector block 14A. In other embodiments, the rod slot 18A may only be within a portion of the length of the rectangular body, and does not exit the rear surface of the connector block 14A. The closure bores 20A and 20B can extend into or through the upper surface 38A to penetrate the rod slot 18A, allowing for the closure devices 22A and/or 22B to make contact with the stabilization member 12A, as described in detail herein.

The connector block 14B can include a rectangular body having an upper surface 38B and a side surface 40B. The upper surface 38B can include the closure bores 20C and 20D. The opening 34 can be located in the side surface 40B. The rod slot 18B can have an aperture within a front surface of the connector block 14A. In some embodiments, the rod slot 18B may extend from the front surface of the connector block 14B and exit through an aperture in a rear surface of the connector block 14B. In other embodiments, the rod slot 18B may only be within a portion of the length of the rectangular body, and does not exit the rear surface of the connector block 14B. The closure bores 20C and 20D can extend into or through the upper surface 38B to penetrate the rod slot 18B, allowing for the closure devices 22C and/or 22D to make contact with the stabilization member 102B, as described in detail herein.

It is noted that the connector blocks 14A, 14B are not limited to the rectangular body shape as shown in FIGS. 1-8, and may be other shapes having other two-dimensional cross-sections without departing from the scope of the present disclosure. For example, the connector block 14A can include a cylindrical shape of a body having a flat surface for the closure bores 20A and 20B and a curved surface wrapping around the rod slot 18A. By way of another example, the connector block 14B can include a cylindrical shape of a body having a flat surface for the closure bores 20C and 20D and a curved surface wrapping around the rod slot 18B. In addition, it is noted the connector block 14B need not have the same shape as the connector block 14A.

The wedged pivot pin 24 can be inserted into the pivot socket 26 to link the connector blocks 14A and 14B. The side surfaces 40A and 40B can be flat or planar such that they can be configured to abut flush against each other, as shown in FIGS. 3 and 4, to facilitate rotation.

The wedged pivot pin 24 can be configured for insertion into and interlocking with the pivot socket 26. For example, the connector blocks 14A and 14B can be rotated such that the axes of rod slot 18A and rod slot 18B are perpendicular and the protruding lobes 32A and 32B of the wedged pivot pin 24 align with the recessed lobes 36A and 36B of the pivot socket 26. As such, the connector blocks 14A and 14B can be moved laterally toward each other so that the protruding lobes 32A and 32B are within the recessed lobes 36A and 36B of the opening 34, and then further moved until the protruding lobes 32A and 32B are through the opening 34 and within the rod slot 18B. Thereafter, the connector blocks 14A and 14B can be rotated such that the axes of the rod slot 18A and the rod slot 18B are closer to parallel. The protruding lobes 32A and 32B can then engage the inside of the rod slot 18B to prevent the connector blocks 14A and 14B from laterally separating, but the extension 28 can rotate against interior surfaces surrounding the opening 34, thereby permitting the connector blocks 14A and 14B to pivot relative to each other. In this regard, the wedged locking system 16 of the pivoting rod connector 10 can be employed to lock the relative angular position of the connector blocks 14A and 14B.

In one non-limiting example, the connector block 14A is oriented in a first direction and the connector block 14B is oriented in a second, different direction to allow for the insertion of the wedged pivot pin 24 into the pivot socket 26. Following insertion, the connector block 14A and/or 14B may be pivoted (e.g., rotated about an axis through the wedged pivot pin 24 and the pivot socket 26) to cause the wedge face 30 and/or the protruding lobes 32A and 32B to engage with portions of an interior cavity defined within the connector block 14B and forming the rod slot 18B (e.g., an interior surface). It is noted the connector block 14A and connector block 14B may be set at any angle relative to one another that does not allow for the passage of the wedged pivot pin 24 through the pivot socket 26 and subsequent disconnecting of the connector block 14A from the connector block 14B.

Figure 3:
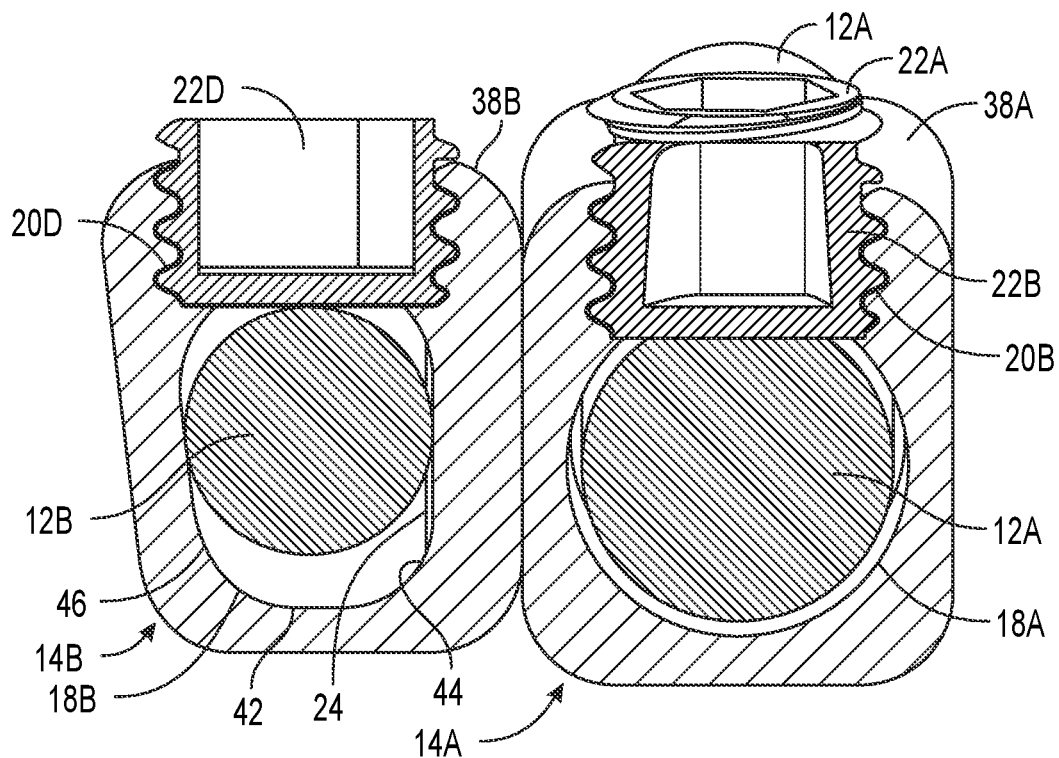
FIG. 3 is a cross-sectional view of the connector blocks of FIG. 1 taken at section 3-3 to show a tapered rod slot and a circular rod slot with rods therein.
Figure 4:
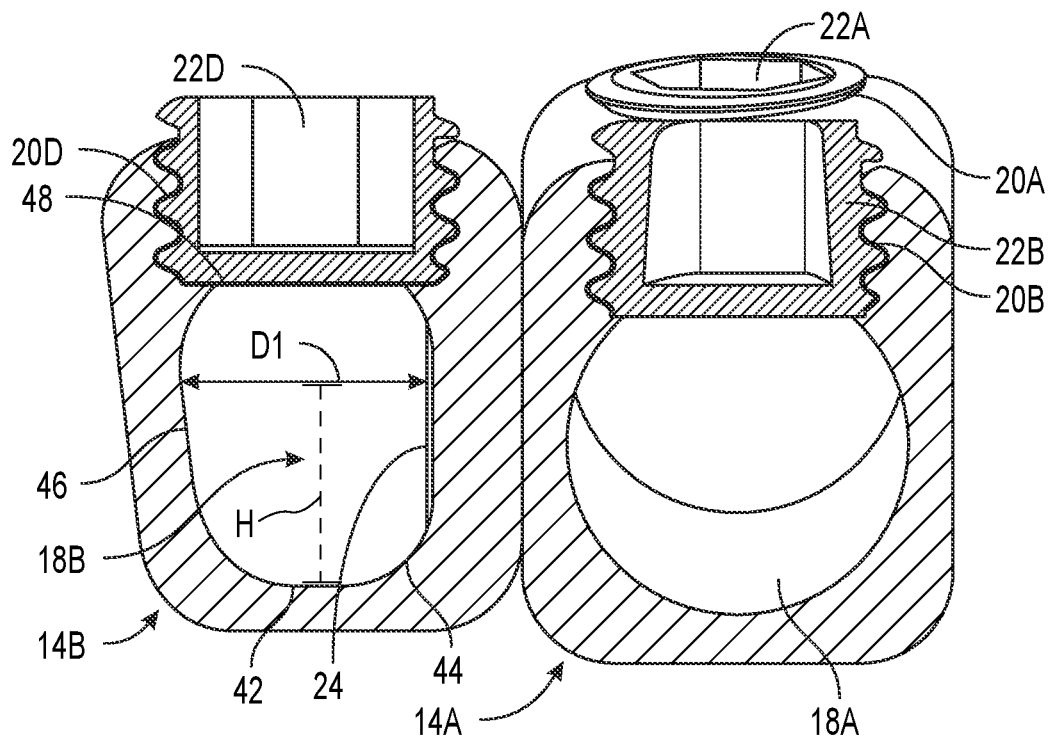
FIG. 4 is a cross-sectional view of the connector blocks of FIG. 1 taken at section 3-3 to show the tapered rod slot and the circular rod slot with the rods removed.

FIGS. 3 and 4 are example embodiments of the pivoting rod connector 10, in accordance with embodiments of the present disclosure. FIG. 3 is a cross-sectional view of the connector blocks 14A and 14B of FIG. 1 taken at section 3-3 to show the tapered rod slot 18B and the circular rod slot 18A with the elongate stabilization members 12A and 12B therein, respectively. FIG. 4 is a cross-sectional view of the connector blocks 14A and 14B of FIG. 1 taken at section 3-3 to show the tapered rod slot 18B and the circular rod slot 18A with the elongate stabilization members 12A and 12B removed. FIGS. 3 and 4 are discussed concurrently.

The rod slot 18A of connector block 14A can include a round or circular hole having a mating profile of elongate stabilization member 12A. In one example, the diameter of rod slot 18A may be slightly larger than the diameter of the elongate stabilization member 12A, such that the elongate stabilization member 12A can freely slide within the rod slot 18A. The elongate stabilization member 12A may be constrained by rod slot 18A from moving relative to the connector block 14A, except for axially along the axis of the rod slot 18A and rotationally about the axis of the rod slot 18A.

The rod slot 18B of the connector block 14B can include a tapered hole (e.g., wedge-shaped or trapezoidal-shaped) including a trough 42, a first sidewall 44, a second sidewall 46 and a ceiling 48. In one example, the first sidewall 44 and the second sidewall 46 may include planar or flat surfaces arranged at an angle relative to each other, such that the second sidewall 46 may be at a distance D1 from the first sidewall 44. In addition, the distance D1 may be different depending on the distance or height H from the trough 42. For instance, the sidewalls 44 and 46 may be closer together proximate to the trough 42 (e.g., where D1 is less) than proximate to the ceiling 48 (e.g., where D2 is greater). In some non-limiting examples, D1 can be less than the diameter of the elongate stabilization member 12B proximate to the trough 42, and distance D1 can be greater than the diameter of elongate stabilization member 12B proximate to the ceiling 48. It is noted that the stabilization member 12B may abut against or press against the wedged pivot pin 24 when the wedged pivot pin 24 is inserted into the pivot socket 26 and the stabilization member 12B is inserted into the rod slot 18B.

The closure bores 20A-20D can be threaded to receive mating threading on closure devices 22A-22D. Closure devices 22A-22D can include threaded fasteners such as set screws having threads along outer diameter surfaces and a socket for a drive tool on upper surfaces. It is noted, however, that the interlocking of the closure bores 20A-20D and the closure devices 22A-22D is not limited to complementary threading, but instead may include any interlocking mechanism (e.g., tab-and-slot, protrusion-and-groove, or the like) that allows for the closure devices 22A-22D to be held in place in the closure bores 20A-20D and hold against the stabilization members 12A, 12B when in a particular angular orientation or an orientation within a range of angles.

In one example, the closure bores 20A and 20B can penetrate through to the rod slot 18A. The closure devices 22A and 22B can be inserted into the closure bores 20A and 20B, respectively, and can exit into the rod slot 18A. The closure devices 22A and 22B can push the elongate stabilization member 12A into firm engagement with at least one interior surface or wall of the interior cavity defined within the connector block 14A and forming the rod slot 16A (e.g., a bottom and/or a side surface of the rod slot 18A), thereby axially and rotationally locking the elongate stabilization member 12A relative to the connector block 14A.

In another example, closure bores 20C and 20D can penetrate through to the rod slot 18B. The closure devices 22C and 22D can be inserted into the closure bores 20C and 20D, respectively, and can exit into the rod bore 18B. The closure devices 22C and 22D can push the elongate stabilization member 12B into firm engagement with at least one interior surface or wall of the interior cavity defined within the connector block 14B and forming the rod slot 18B (e.g., the first sidewall 44 and/or the second sidewall 46), thereby axially and rotationally locking the elongate stabilization member 12B relative to the connector block 14A. Furthermore, the closure devices 22C and 22D can push the elongate stabilization member 12B into firm engagement with the wedged pivot pin 24 (e.g., with the wedge face 30 and/or the protruding lobes 32A, 32B of the extension 28 of the wedged pivot pin 24), thereby locking the pivoting or angulation position of the connector block 14B relative to the connector block 14A.

Figure 5:
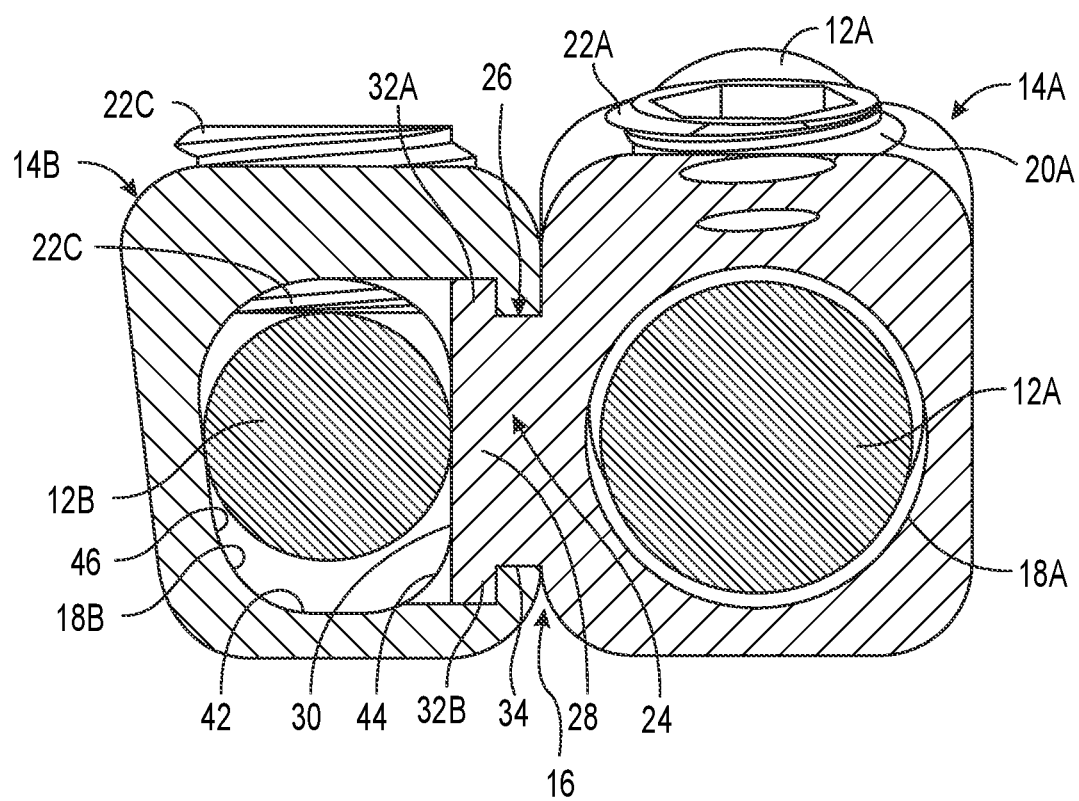
FIG. 5 is a cross-sectional view of the connector blocks of FIG. 1 taken at section 5-5 to show the wedged pivot pin engaged with a rod.
Figure 6:
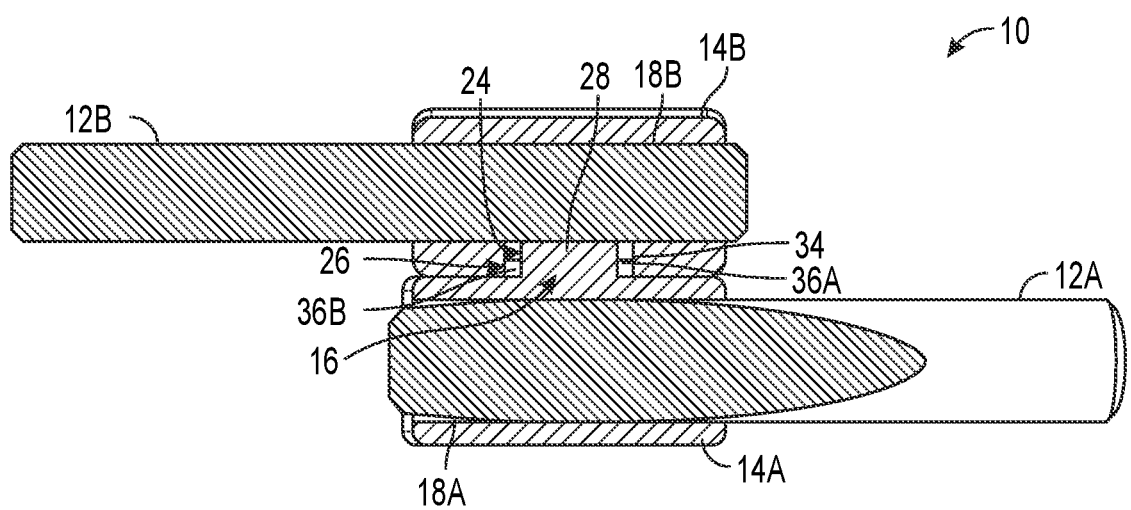
FIG. 6 is a cross-sectional view of the connector blocks of FIG. 1 taken at section 6-6 to show the wedged pivot pin engaged with a rod.

FIGS. 5 and 6 are example embodiments of the pivoting rod connector 10, in accordance with embodiments of the present disclosure. FIG. 5 is a cross-sectional view of the connector blocks 14A and 14B of FIG. 1 taken at section 5-5 to show the wedged pivot pin 24 engaged with the elongate stabilization member 12B. FIG. 6 is a cross-sectional view of the connector blocks 14A and 14B of FIG. 1 taken at section 6-6 to show wedged pivot pin 24 engaged with the elongate stabilization member 12B. FIGS. 5 and 6 are discussed concurrently.

In one example, the closure devices 22A and/or 22B (22B shown in FIG. 1) can be threaded into closure bores 20A and/or 20B (20B shown in FIG. 1) to axially lock the elongate stabilization member 12A. In particular, the closure devices 22A and/or 22B can push the elongate stabilization member 12A downward against the bottom of the rod slot 18A.

In another example, closure devices 22C and/or 22D (22D shown in FIG. 1) can be threaded into the closure bores 20C and/or 20D (20D shown in FIG. 1) to axially lock the elongate stabilization member 12B. In particular, the closure devices 22C and/or 22D can push the elongate stabilization member 12B downward toward the trough 42. The elongate stabilization member 12B can be prevented from touching the trough 42 due to the angling of the sidewall 46 relative to the sidewall 44. The sidewall 46 can push, or wedge, the elongate stabilization member 12B toward the sidewall 44. The insertion of the extension 28 into the rod slot 18B can prevent the elongate stabilization member 12B from contacting the sidewall 44. Thus, the elongate stabilization member 12B may be pushed downward by the closure devices 22C, 22D and rightward by the sidewall 46 (e.g., with respect to the orientation of FIG. 5) toward the extension 28 (and may or may not contact the sidewall 44). In addition, engagement of the elongate stabilization member 12B against the extension 28 can push the sidewall 44 of the connector block 14B leftward (with respect to the orientation of FIG. 5) into engagement with the protruding lobes 32A and 32B, thereby securing the position of the connector blocks 14A relative to the connector block 14B (and vice versa). As such, the engagement of the stabilization member 12B and the wedged pivot pin 24 may operate as a locking mechanism for the pivoting rod connector 10, for purposes of the present disclosure.

In this regard, tightening of the closure devices 22C and 22D can therefore simultaneously lock the axial and rotational position of the elongate stabilization member 12B relative to the connector block 14B, and the pivoted position between the connector block 14B and the connector block 14A. Such simultaneous tightening can facilitate precise implantation (e.g., at the desired orientation, distance, and/or angle) of the elongated stabilization members 12A and 12B by the surgeon.

It is noted that the pivoting rod connector 10 may be oriented within a patient such that access to the closure devices 22C and 22D is on the posterior side of the patient in a location easily accessible and visible to the surgeon through a posterior incision in the patient.

Figure 7:
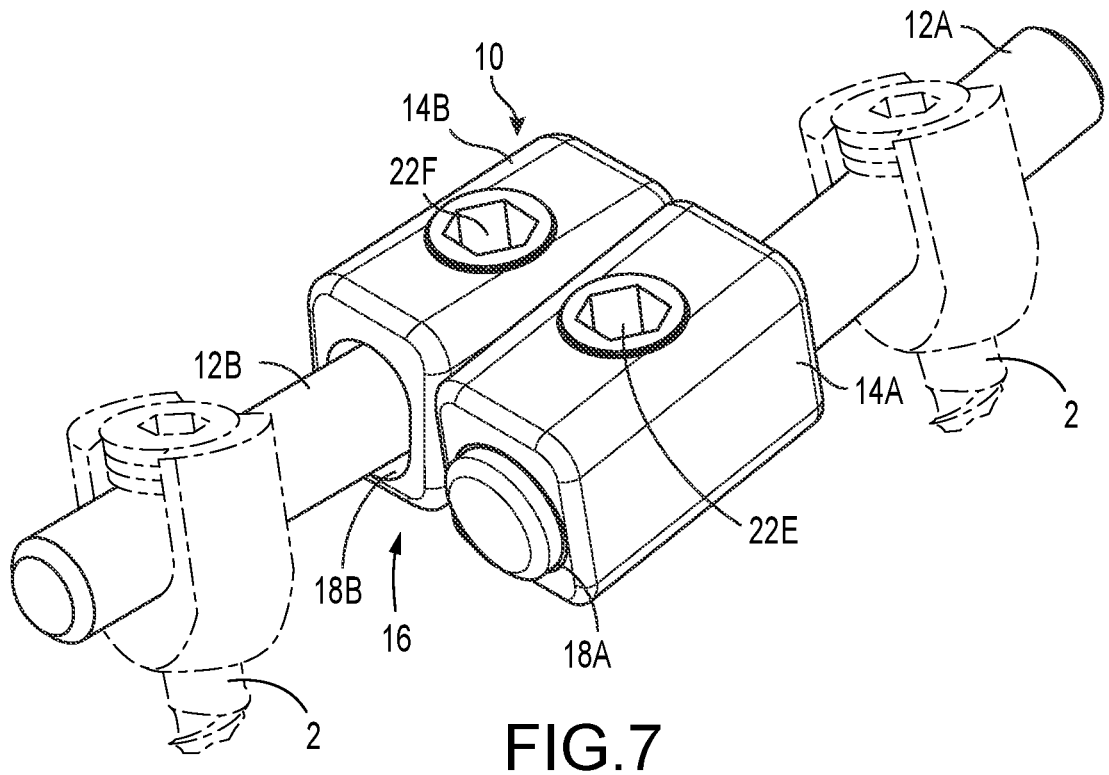
FIG. 7 is a perspective view of a second example or variation of FIG. 1 of a pivoting rod connector coupling a pair of elongate stabilization members using connector blocks connected by a wedged locking system.
Figure 8:
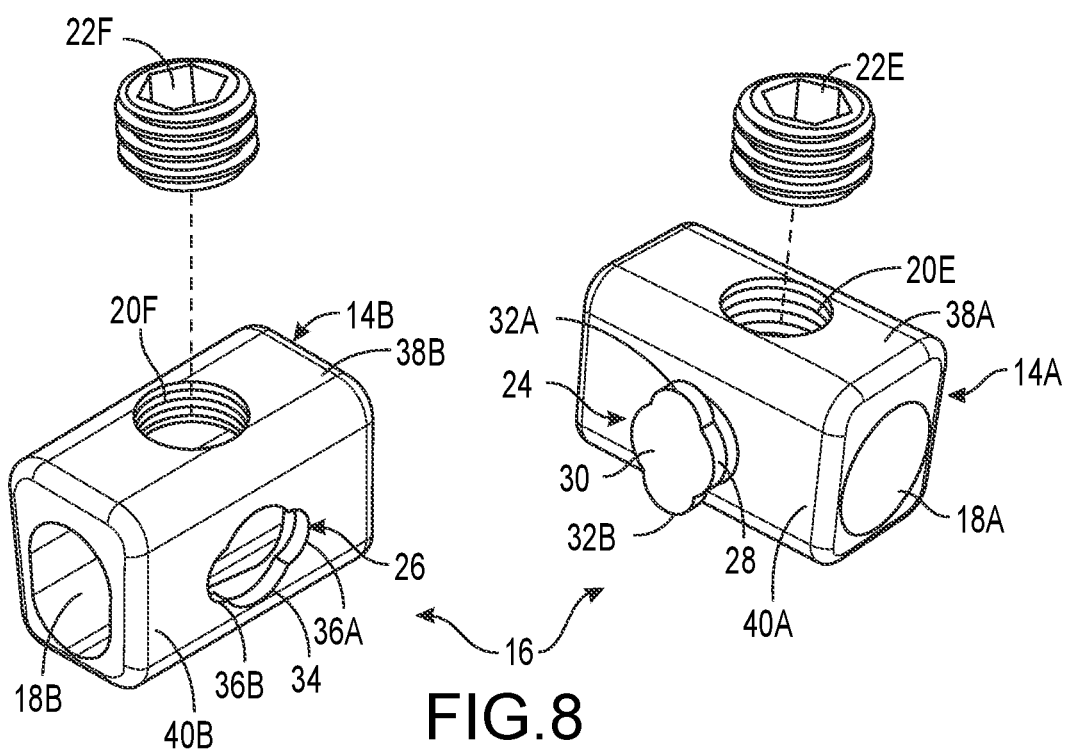
FIG. 8 is an exploded view of the pivoting rod connector of FIG. 7 showing a pair of connector blocks couplable via a wedged pivot pin of the wedged locking system.

Although FIGS. 1-6 are illustrated as including the closure bores 20A-20D and corresponding the closure devices 22A-22D, it is noted that the pivoting rod connector 10 may include any number of closure bores and corresponding closure devices without departing from the scope of the present disclosure, to the extent the total length and/or width of the pivoting rod connector 10 does not inhibit the installation of the pivoting rod connector 10 into a patient, and/or does not weaken the coupling of the pivoting rod connector 10 to the stabilization members 12A, 12B. For example, FIGS. 7-8 illustrate a variation of FIGS. 1-6, in which the pivoting rod connector 10 only includes a single closure bore 20E and a single closure device 22E on a first side, and a single closure bore 20F and a single closure device 22F on a second side. By way of another example, each side of the pivoting rod connector 10 may include three or more closure bores 20/corresponding closure devices 22. Further, the sides of the pivoting rod connector 10 may include an unequal number of closure bores 20/corresponding closure devices 22. In addition, it is noted the closure bores 20 (and corresponding closure devices 22) may be the same or different diameters and/or lengths within the pivoting rod connector 10, without departing from the scope of the present disclosure.

It is noted that FIGS. 1-8 provide a non-obvious benefit of a lower total height requirement for the pivoting rod connector 10 with the components of the wedged locking system 16 extending from side surfaces 40A and 40B and not from top or bottom surfaces of the block connectors 14A, 14B, respectively.

FIGS. 9-16 in general illustrate a pivoting rod connector 100, in accordance with one or more embodiments of the present disclosure. It is noted aspects and/or components of the pivoting rod connector 100 may be shared with and/or combinable with one or more aspects and/or components of pivoting rod connectors 10, 200, 250, 280, 300, 350, 360, 370 without departing from the scope of the present disclosure, unless otherwise noted.

Figure 9:
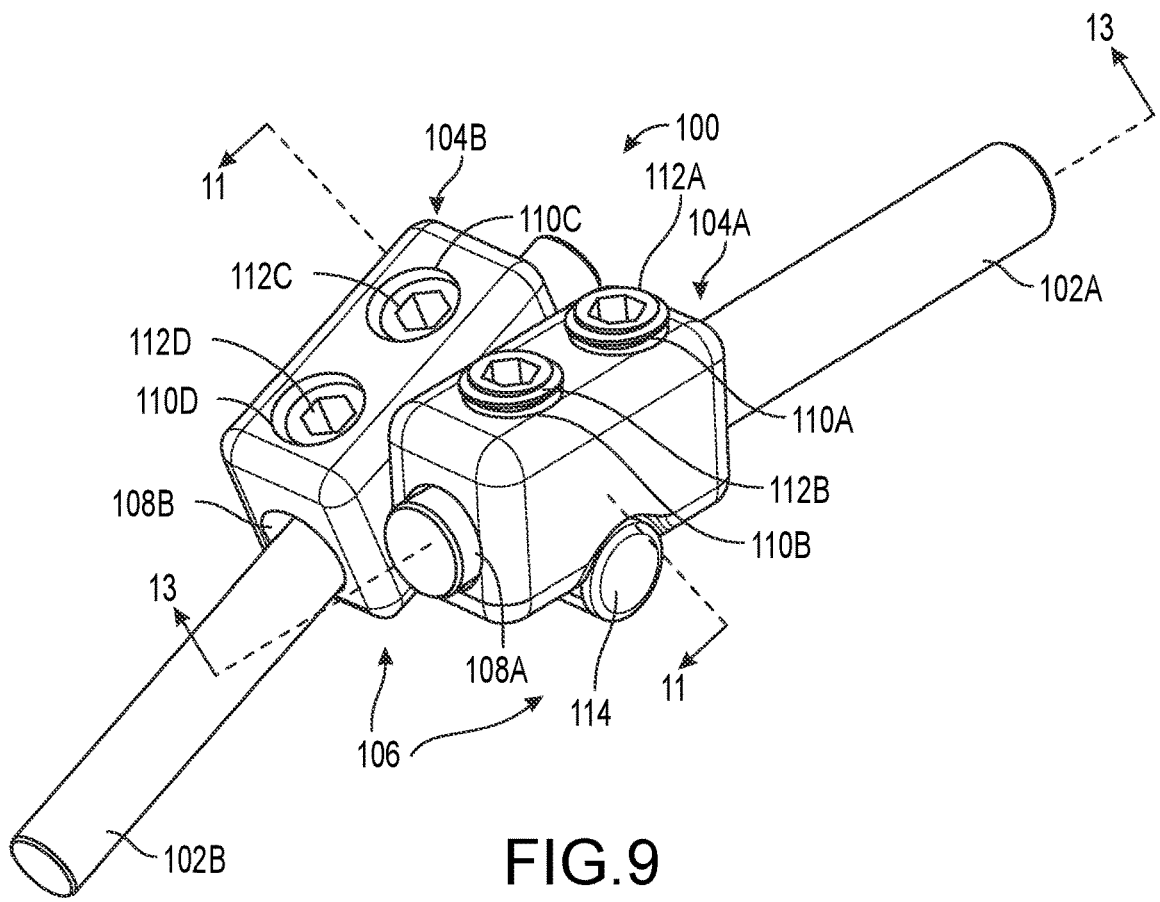
FIG. 9 is a perspective view of a pivoting rod connector coupling a pair of elongate stabilization members using connector blocks connected by a pivot pin locking system.

FIG. 9 is a perspective view of the pivoting rod connector 100 coupling a first elongate stabilization member 102A and a second elongate stabilization member 102B using a first connector block 104A and a second connector block 104B, in accordance with embodiments of the present disclosure.

The pivoting rod connector 100 includes the first connector block 104A and the second connector block 104B. The connector blocks 104A, 104B are linked by a threaded locking system 106. It is noted the threaded locking system 106 may be considered a pivot mechanism, for purposes of the present disclosure. The connector block 104A includes a rod slot 108A and the second connector block 104B includes a rod slot 108B.

In some embodiments, the first connector block 104A may include a closure bore 110A and/or a closure bore 110B. The closure bore 110A and/or the closure bore 110B may be operable to receive a closure device 112A or a closure device 112B, respectively. In additional embodiments, the second connector block 104B may include a closure bore 110C and/or a closure bore 110D. The closure bore 110C and/or the closure bore 110D may be operable to receive a closure device 112C and/or a closure device 112D, respectively. The closure devices 112A-112D may be configured to engage the closure bores 110A-110D. For example, as discussed in detail herein, the closure bores 110A-110D may include threading that is complementary to threading on the closure devices 112A-112D.

In some examples, the elongate stabilization members 102A and 102B can include rigid rods or members. However, in other examples, the elongate stabilization members 102A and 102B can include other components including, but not limited to, flexible cords or members.

The pivoting rod connector 100 can be configured to hold the first and second elongate stabilization members 102A and 102B in a fixed angular relationship. The first and second elongate stabilization members 102A and 102B can be inserted into the rod slots 108A and 108B, respectively, and held therein via closure devices 112A-112D. The closure devices 112A-112D can be inserted into closure bores 110A-110D to axially lock the positions of the elongate stabilization members 102A and 102B relative to the connector blocks 104A and 104B, respectively. Simultaneously, the closure devices 112A and/or 112B can push the elongate stabilization member 102A downward within the rod slot 108A to push the elongate stabilization member 102A downward into engagement with a threaded pivot pin 114, thereby locking the angular position between the connector blocks 104A and 104B.

Figure 10:
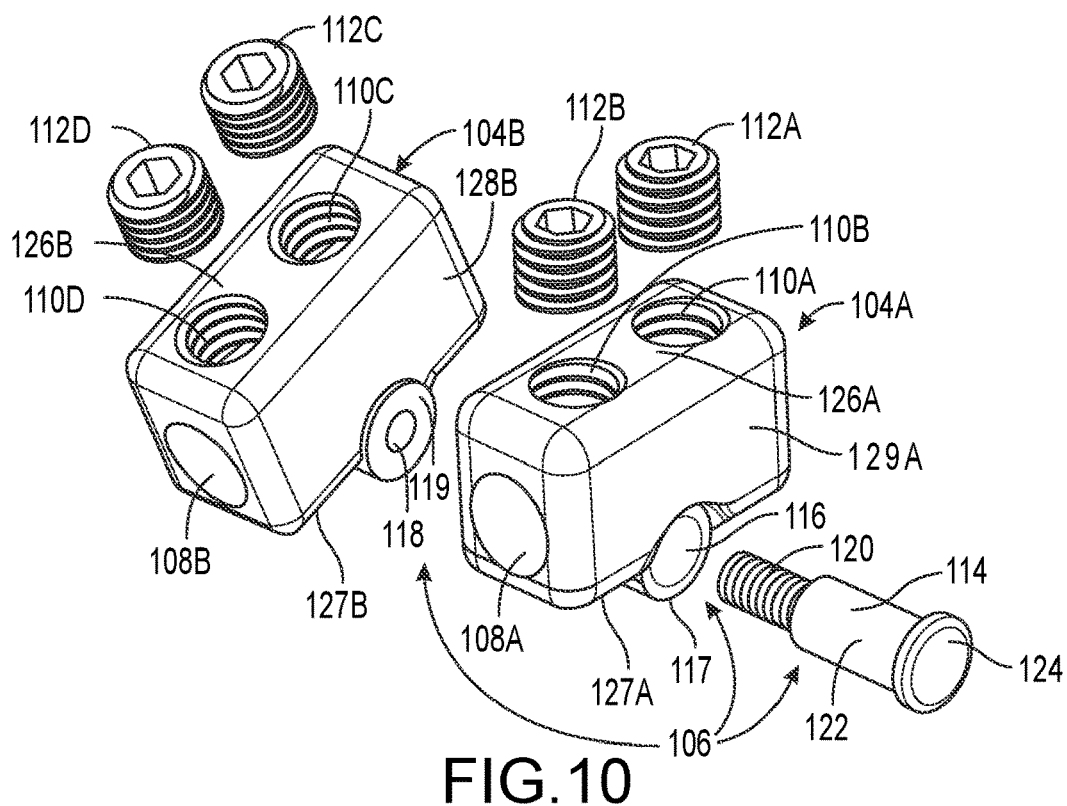
FIG. 10 is an exploded view of the rod connector of FIG. 9 showing a pair of connector blocks coupled via a threaded pivot pin of the pivot pin locking system.

FIG. 10 is an exploded view of the pivoting rod connector 100 of FIG. 9 showing the first connector block 104A and the second connector block 104B coupled via the threaded pivot pin 114 and bores 116, 118, in accordance with embodiments of the present disclosure. In some embodiments, at least the pivot pin 114 and the bores 116, 118 form the threaded locking system 106. The first connector block 104A can include the bore 116 (e.g., which is either smooth-bore or threaded) within a first lower body portion 117. The second connector block 104B can include the bore 118 (e.g., which is either smooth-bore or threaded, and which may be pass-through or stop some distance into a width of the second connector block 104B) within a second lower body portion 119. The threaded pivot pin 114 can include a shaft with a threaded shaft portion 120, a smooth shaft portion 122, and a head 124. It is noted, however, that the shaft of the threaded pivot pin 114 may be entirely threaded. In addition, it is noted the threaded pivot pin 114 may engage another threaded component (e.g., a nut or the like) inserted within or proximate to the first connector block 104A and/or the second connector block 104B. In one non-limiting example, a nut may be inserted within a recess or embedded underneath a surface of the connector block 104A and/or 104B, such that the bores 116, 118 may be smooth-bore or threaded).

The connector block 104A can include a rectangular body having an upper surface 126A, a bottom surface 127A, and a side surface 128A. The upper surface 126A can include the closure bores 110A and 110B. The first lower body portion 117 can extend from the bottom surface 127A. The rod slot 108A can have an aperture within a front surface of the connector block 104A. In some embodiments, the rod slot 108A may extend from the front surface of the connector block 104A and exit through an aperture in a rear surface of the connector block 104A. In other embodiments, the rod slot 108A may only be within a portion of the length of the rectangular body, and does not exit the rear surface of the connector block 104A. The closure bores 110A and 110B can extend into or through the upper surface 126A to penetrate the rod slot 108A, allowing for the closure devices 112A and/or 112B to make contact with the stabilization member 102A, as described in detail herein.

The connector block 104B can include a rectangular body having an upper surface 126B, a bottom surface 127B, and a side surface 128B. The upper surface 126B can include the closure bores 110C and 110D. The second lower body portion 119 can extend from the bottom surface 127B. The rod slot 108B can have an aperture within a front surface of the connector block 104B. In some embodiments, the rod slot 108B may extend from the front surface of the connector block 104B and exit through an aperture in a rear surface of the connector block 104B. In other embodiments, the rod slot 108B may only be within a portion of the length of the rectangular body, and does not exit the rear surface of the connector block 104B. The closure bores 110C and 110D can extend into or through the upper surface 126B to penetrate the rod slot 108B, allowing for the closure devices 112C and/or 112D to make contact with the stabilization member 102B, as described in detail herein.

It is noted that the connector blocks 104A, 104B are not limited to the rectangular body shape as shown illustrated in FIGS. 9-16, and may be other shapes having other two-dimensional cross-sections without departing from the scope of the present disclosure. For example, the connector block 104A can include a cylindrical shape of a body having a flat surface for the closure bores 110A and 110B and a curved surface wrapping around the rod slot 108A. By way of another example, the connector block 104B can include a cylindrical shape of a body having a flat surface for the closure bores 110C and 110D and a curved surface wrapping around the rod slot 108B. In addition, it is noted the connector block 104B need not have the same shape as the connector block 104A.

Figure 11:
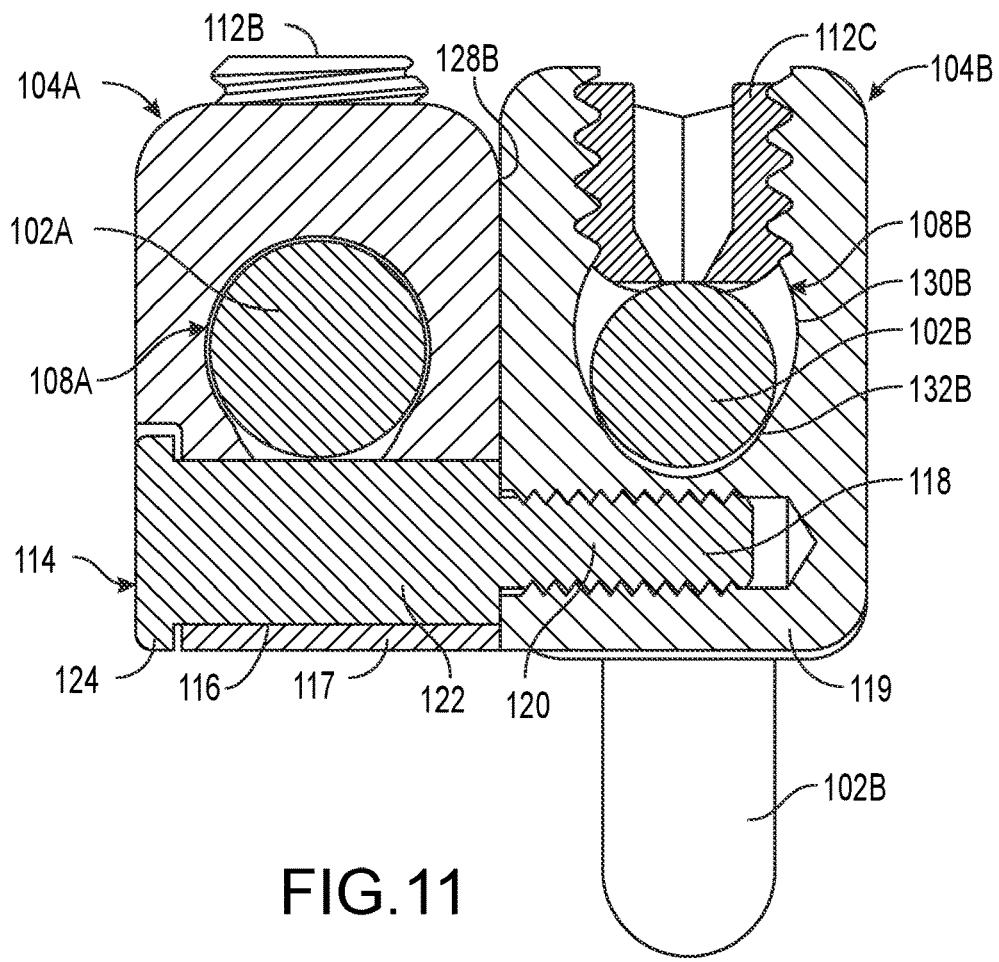
FIG. 11 is a cross-sectional view of the connector blocks of FIG. 9 taken at section 11-11 to show a rod pinned against the threaded pivot pin.
Figure 13:
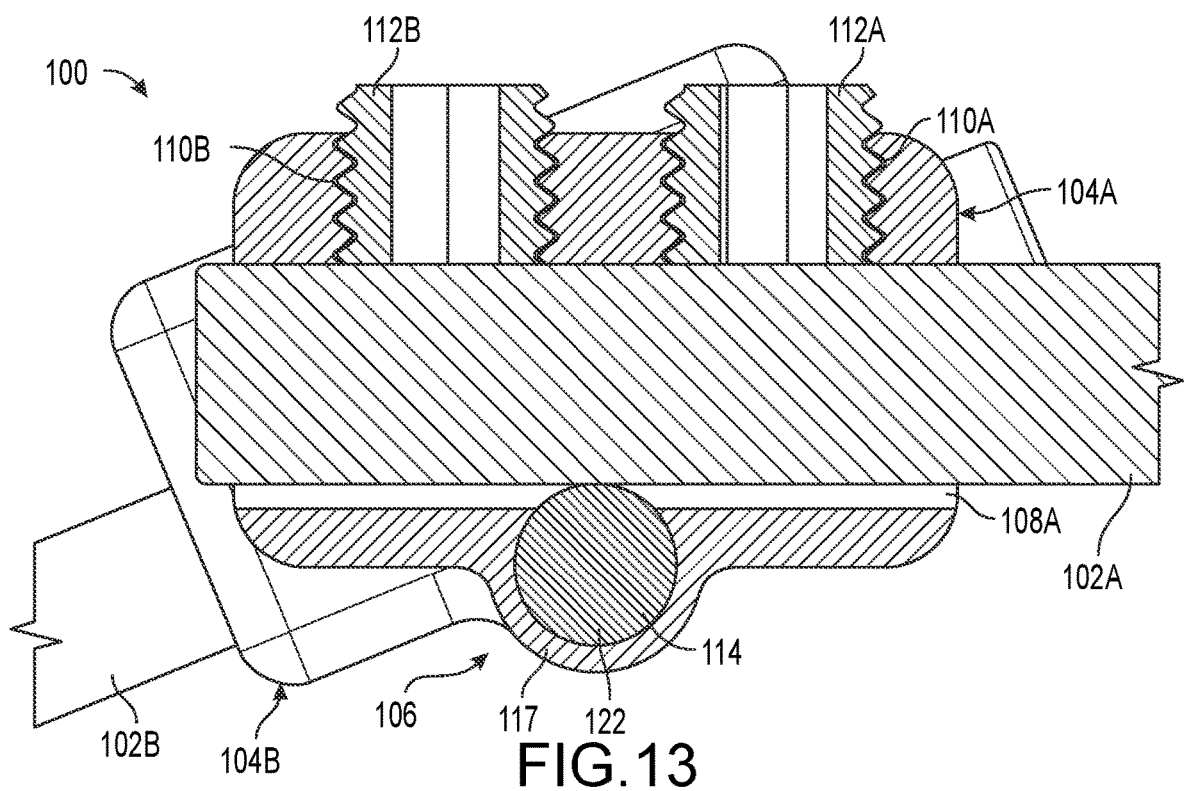
FIG. 13 is a cross-sectional view of the connector blocks of FIG. 9 taken at section 13-13 to show a rod pinned against the threaded pivot pin.
Figure 14:
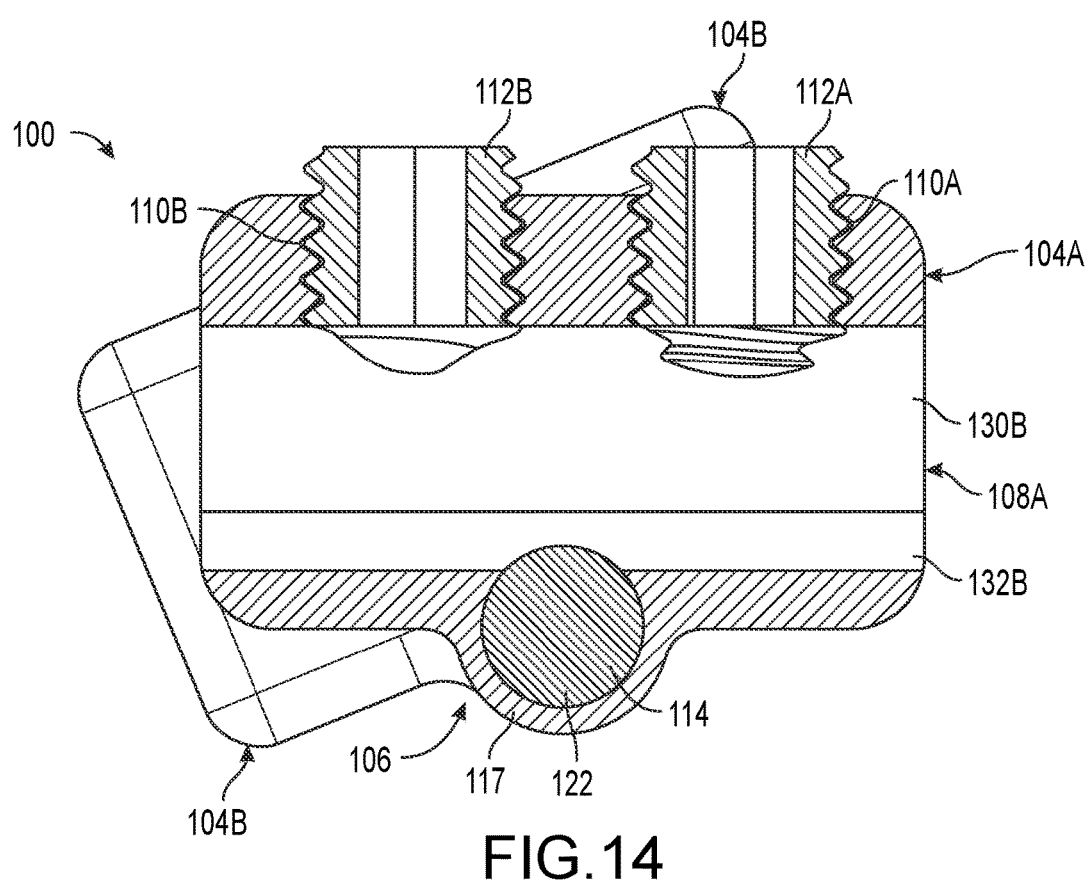
FIG. 14 is a cross-sectional view of the connector blocks of FIG. 9 taken at section 13-13 with the rods removed to show the threaded pivot pin protruding into a rod slot.

The threaded pivot pin 114 can be threaded into the bore 118 to couple the connector block 104A with the connector block 104B. For example, the threaded pivot pin 114 may be threaded until the head 124 of the threaded pivot pin 114 makes contact with the protrusion 117 of the first connector block 104A. The side surfaces 128A (e.g., as shown in FIG. 11) and 128B can be flat or planar such that they can be configured to abut flush against each other (e.g., as illustrated in FIGS. 13 and 14), to facilitate rotation. In some embodiments, the sidewall 129A may be counterbored to accept the head 124, so that the head 124 does not extend beyond the sidewall 129A (which may increase the width of the connector block 104A/the pivoting rod connector 100, and adversely affect or inhibit the installation of the pivoting rod connector 100 into a patient). It is noted that head 124 may have a diameter larger than the shaft of the threaded pivot pin 114 (e.g., the smooth shaft portion 122) to abut the first lower body portion 117. It is noted that the head 124 can prevent the connector block 104A from moving laterally away from the connector block 104B.

The threaded pivot pin 114 can be inserted through the bore 116 and into the bore 118. For example, the connector blocks 104A and 104B can be positioned such that the axes of the bore 116 and the bore 118 are co-axially aligned. The connector blocks 104A and 104B can be moved laterally toward each other until the side surfaces 128A and 128B are flush. In some example embodiments, the threaded pivot pin 114 can be positioned such that the threaded shaft 120 can be within the bore 118 and the smooth shaft 122 can be within the bore 116. In other embodiments, the threaded shaft 120 and the bore 118 can be threadedly engaged to prevent the connector blocks 104A and 104B from laterally separating.

In some embodiments, the width of the shaft 122 can be greater than the width of the connector block 104A such that the connector block 104A can freely pivot about the threaded pivot pin 114 between the connector block 104B and the head 124 when the threaded pivot pin 114 is fully seated in the bore 118. In examples, the width of the shaft 122 can be less than the width of the connector block 104A such that the connector block 104A can be pinned to the connector block 104B via the head 124.

The shaft 122 and the bore 116 can be freely engaged such that the connector block 104A can pivot about the threaded pivot pin 114, thereby permitting the connector blocks 104A and 104B to pivot relative to each other. In this regard, the threaded locking system 106 of the pivoting rod connector 100 can be employed to lock the relative angular position of the connector blocks 104A and 104B by engaging the threaded pivot pin 114 to prevent rotation of the connector block 104A thereabouts. Furthermore, as mentioned above, the threaded pivot pin 114 can be tightened to push the connector block 104A against the connector block 104B and prevent relative rotation by squeezing of the connector block 104A between the connector block 104B and the head 124. For example, tightening the threaded pivot pin 114 may cause the first connector block 104A and the second connector block 104B is draw or pull closer together, such that friction or interlocking components between the adjacent surfaces of the first connector block 104A and the second connector block 104B inhibits angulation of the pivoting rod connector 100. As such, the threaded locking system 106 may operate as a locking mechanism for the pivoting rod connector 100, for purposes of the present disclosure.

Figure 12:
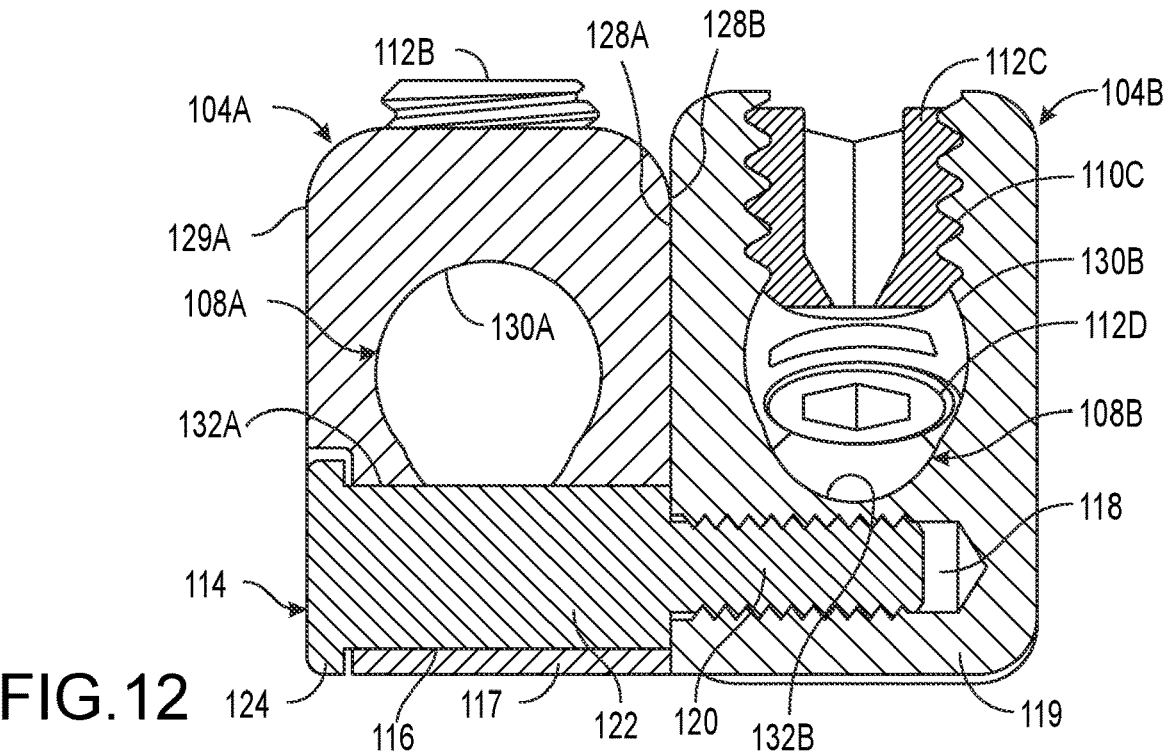
FIG. 12 is a cross-sectional view of the connector blocks of FIG. 9 taken at section 11-11 with the rods removed to show the threaded pivot pin protruding into the rod slot.

FIGS. 11 and 12 are example embodiments of the pivoting rod connector 100, in accordance with embodiments of the present disclosure. FIG. 11 is a cross-sectional view of the connector blocks 104A and 104B of FIG. 9 taken at section 11-11 to show the elongate stabilization member 102A pinned against the threaded pivot pin 114. FIG. 12 is a cross-sectional view of the connector blocks 104A and 104B of FIG. 9 taken at section 11-11 with the elongate stabilization members 102A and 102B removed to show the threaded pivot pin 114 protruding into the rod slot 108A. FIGS. 11 and 12 are discussed concurrently.

The rod slot 108A of the connector block 104A can include a lobed hole having a round or circular upper portion 130A intersecting a round or circular lower portion 132A. In one example, the diameter of the upper portion 130A can be larger than the lower portion 132A to form a lobed shape. The threaded pivot pin 114 can extend into the rod slot 108A to extend across the lower portion 132A to provide a base for the threaded pivot pin 114 at approximately the lower end of the diameter of upper portion 130A. The upper portion 130A of the rod slot 108A can have a mating profile of the elongate stabilization member 102A. The lower portion 132A of the rod slot 108B can permit access to the upper portion 130A by the threaded pivot pin 114. As such, the elongate stabilization member 102A can be constrained from moving relative to the connector block 104A except for axially along the axis of the rod slot 108A and rotationally about the axis of the rod slot 108A until the closure devices 112A and 112B are engaged to push the elongate stabilization member 102A against the threaded pivot pin 114. The elongate stabilization members having diameters smaller than the elongate stabilization member 102A can additionally rest on the threaded pivot pin 114 within the rod slot 108A. As such, the stabilization member 102A may abut against or press against the threaded pivot pin 114 when the threaded pivot pin 114 is inserted into the bore 116 and the stabilization member 102A is inserted into the rod slot 108A. Thus, the stabilization member 102 abutting against the threaded pivot pin 114 may operate as a locking mechanism for the pivoting rod connector 100, for purposes of the present disclosure.

The slot 108B of the connector block 104B can include a lobed hole having a round or circular upper portion 130B intersecting a round or circular lower portion 132B. In one example, the diameter of the upper portion 130B can be larger than the lower portion 132B to form a lobed shape. The upper portion 130B can be sized to have a mating profile with large sized elongate stabilization members such as the elongate stabilization member 102A, and the lower portion 132B can be sized to have a mating profile with small sized elongate stabilization members such as the elongate stabilization member 102B. As such, the elongate stabilization member 102A (when placed in the rod slot 108B) can be constrained from moving relative to the connector block 104B except for axially along the axis of the rod slot 108B and rotationally about the axis of the rod slot 108B. Likewise, the elongate stabilization member 102B can be constrained from moving relative to the connector block 104B except for axially along the axis of the rod slot 108B and rotationally about the axis of the rod slot 108B when the closure devices 112C and 112D are extended into the rod slot 108B.

The closure bores 110A-110D can be threaded to receive mating threading on the closure devices 112A-112D. The closure devices 112A-112D can include fasteners such as set screws having threads along outer diameter surfaces and a socket for a drive tool on upper surfaces. It is noted, however, that the interlocking of the closure bores 110A-110D and the closure devices 112A-112D is not limited to complementary threading, but instead may include any interlocking mechanism (e.g., tab-and-slot, protrusion-and-groove, or the like) that allows for the closure devices 112A-112D to be held in place in the closure bores 110A-110D and hold against the stabilization members 102A, 102B when in a particular angular orientation or an orientation within a range of angles.

In one example, the closure bores 110A and 110B can penetrate through to the rod slot 108A. The closure devices 112A and 112B can be inserted into the closure bores 110A and 110B, respectively, and can exit into the rod slot 108A.

In another example, the closure bores 110C and 110D can penetrate through to the rod slot 108B. The closure devices 112C and 112D can be inserted into the closure bores 110C and 110D, respectively, and can exit into the rod slot 108B.

FIGS. 13 and 14 are example embodiments of the pivoting rod connector 100, in accordance with embodiments of the present disclosure. FIG. 13 is a cross-sectional view of the connector blocks 104A and 104B of FIG. 9 taken at section 13-13 to show the elongate stabilization member 102A pinned against the threaded pivot pin 114. FIG. 14 is a cross-sectional view of the connector blocks 104A and 104B of FIG. 9 taken at section 13-13 to show the threaded pivot pin 114 protruding into the rod slot 108A. FIGS. 13 and 14 are discussed concurrently.

In one example, the closure devices 112C and 112D (112C and 112D shown in FIG. 9) can be threaded into the closure bores 110C and 110D (112C and 112D shown in FIG. 9) to axially lock the elongate stabilization member 102B. In particular, the closure devices 112C and 112D can push the elongate stabilization member 102B downward against the bottom of rod slot 108B.

In another example, the closure devices 112A and 112B can be threaded into the closure bores 110A and 110B to axially lock the elongate stabilization member 102A. In particular, the closure devices 112A and 112B can push the elongate stabilization member 102A downward toward the threaded pivot pin 114. The elongate stabilization member 102A can be prevented from touching the bottom of the rod slot 108A due to the threaded pivot pin 114. Engagement of the elongate stabilization member 102A against the threaded pivot pin 114 can prevent the connector block 104A from rotating about the threaded pivot pin 114, thereby binding up the relative positions of the connector blocks 104A and 104B.

In this regard, tightening of the closure devices 112A and 112B can therefore simultaneously lock the axial and rotational position of the elongate stabilization member 102A relative to the connector block 104A, and the pivoted position between the connector block 104A and the connector block 104B. Such simultaneous tightening can facilitate precise implantation (e.g., at the desired orientation, distance, and/or angle) of the elongated stabilization members 102A and 102B by the surgeon.

It is noted that the pivoting rod connector 100 may be oriented within a patient such that access to the closure devices 112A and 112B is on the posterior side of the patient in a location easily accessible and visible to the surgeon through a posterior incision in the patient.

Figure 15:
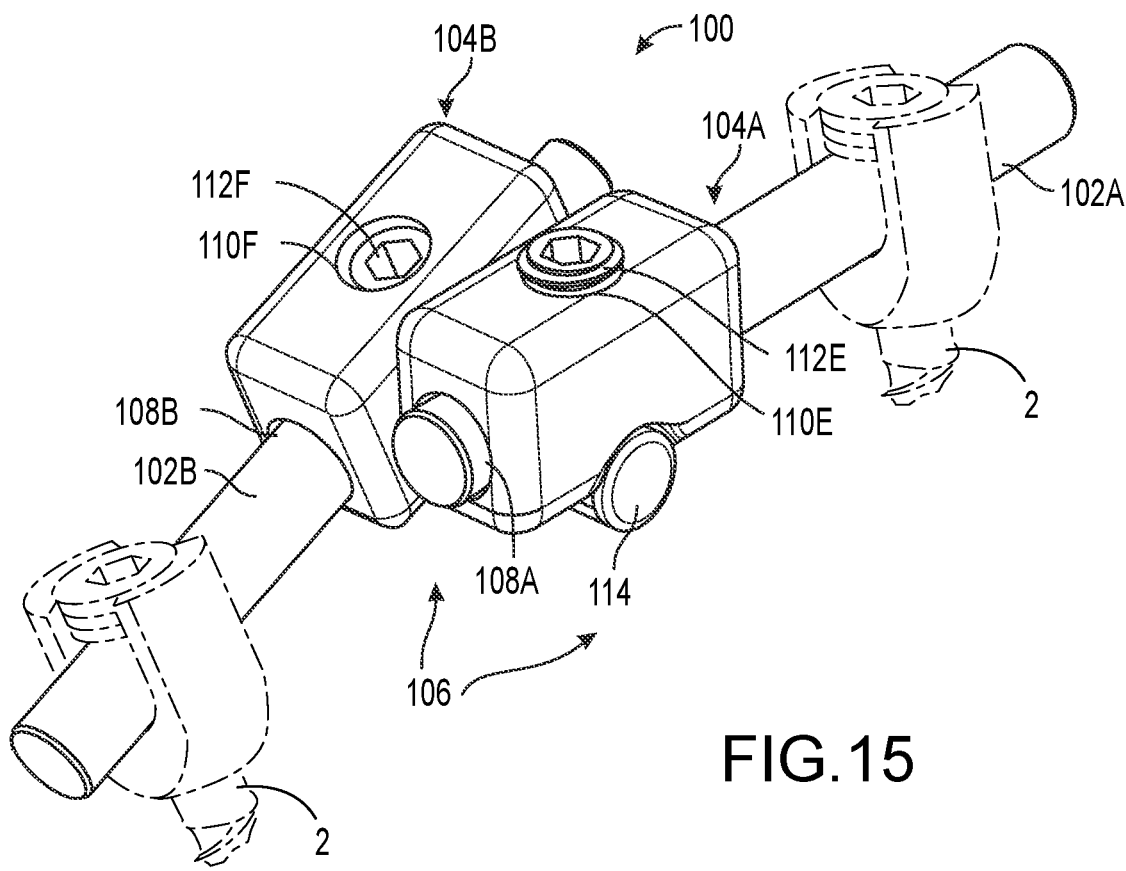
FIG. 15 is a perspective view of a second example or variation of FIG. 9 of a pivoting rod connector coupling a pair of elongate stabilization members using connector blocks connected by a wedged locking system.
Figure 16:
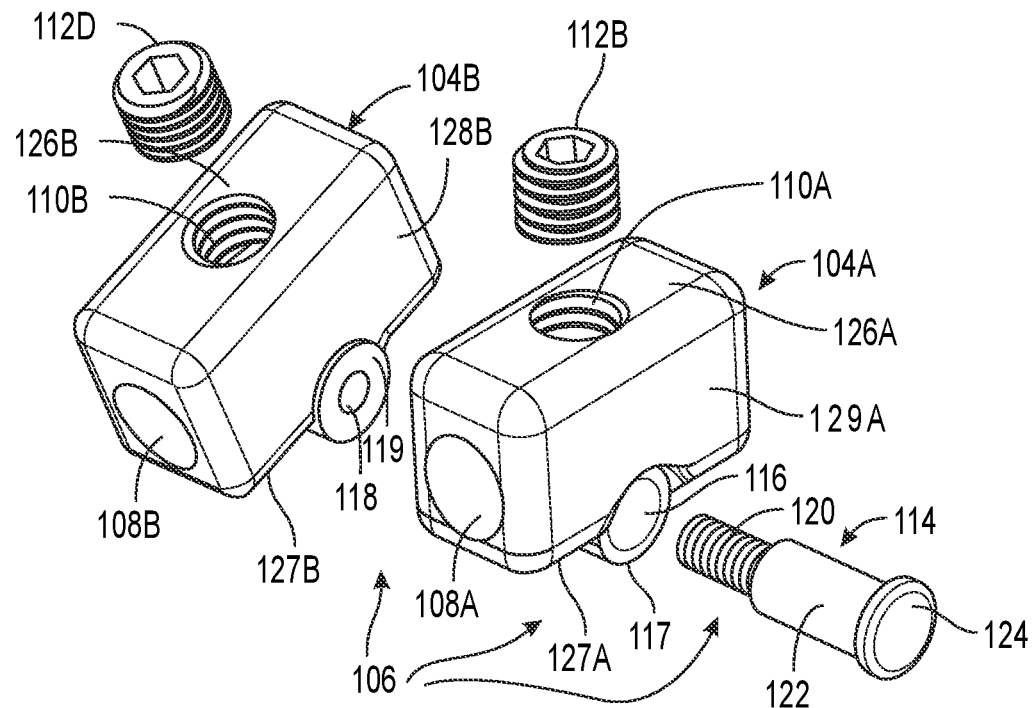
FIG. 16 is an exploded view of the pivoting rod connector of FIG. 15 showing a pair of connector blocks couplable via a wedged pivot pin of the wedged locking system.

Although FIGS. 9-14 are illustrated as including closure bores 110A-110D and corresponding closure devices 112A-112D, it is noted that the pivoting rod connector 100 may include any number of closure bores and corresponding closure devices without departing from the scope of the present disclosure, to the extent the total length and/or width of the pivoting rod connector 100 does not inhibit the installation of the pivoting rod connector 100 into a patient, and/or does not weaken the coupling of the pivoting rod connector 100 to the stabilization members 102A, 102B. For example, FIGS. 15 and 16 illustrate a variation of FIGS. 9-14, in which the pivoting rod connector 100 only includes a closure bore 110E/closure device 112E on a first side, and a closure bore 110F/closure device 112F on a second side. By way of another example, each side of the pivoting rod connector 100 may include three or more closure bores 110/corresponding closure devices 112. Further, the sides of the pivoting rod connector 100 may include an unequal number of closure bores 110/corresponding closure devices 112. In addition, it is noted the closure bores 110 (and corresponding closure devices 112) may be the same or different diameters and/or lengths within the pivoting rod connector 100, without departing from the scope of the present disclosure.

FIGS. 17-20 in general illustrate a pivoting rod connector 200, in accordance with one or more embodiments of the present disclosure. It is noted aspects and/or components of the pivoting rod connector 200 may be shared with and/or combinable with one or more aspects and/or components of pivoting rod connectors 10, 100, 250, 300, 350, 360, 370 without departing from the scope of the present disclosure, unless otherwise noted.

Figure 17:
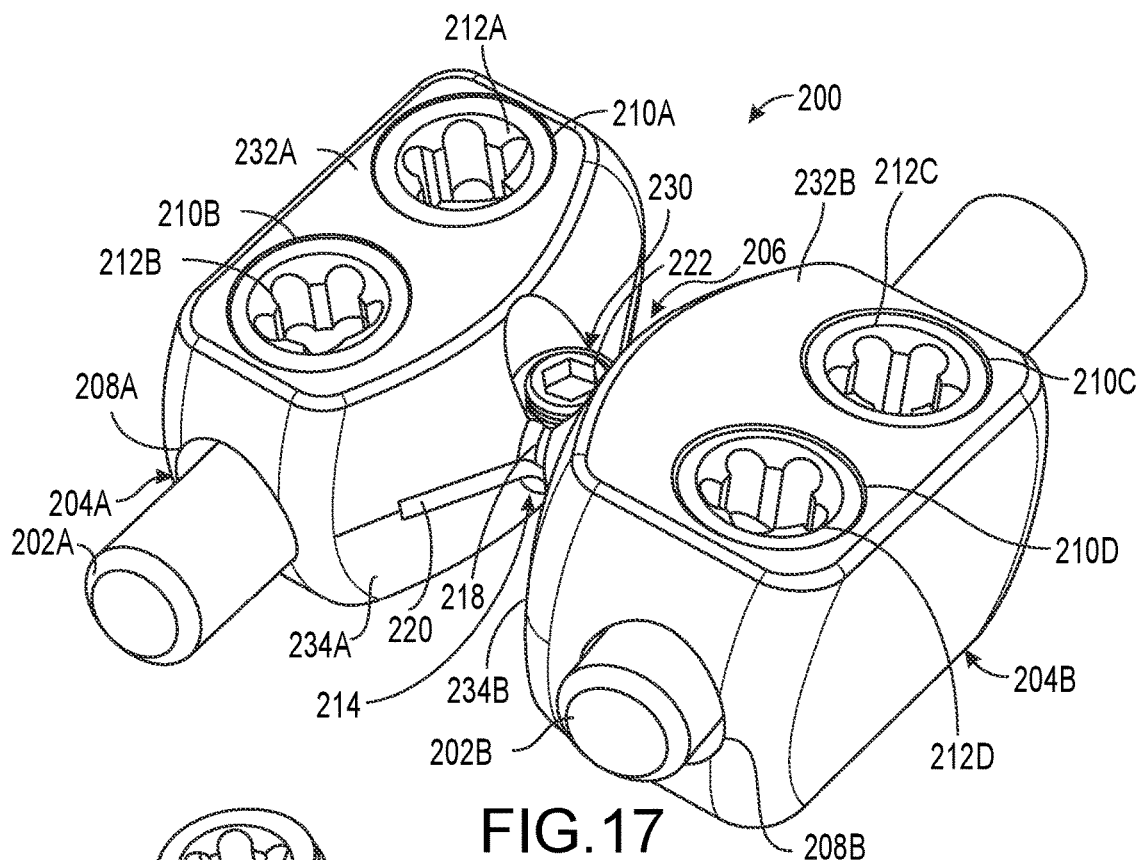
FIG. 17 is a perspective view of a first example of a pivoting rod connector coupling a pair of elongate stabilization members using connector blocks connected by a swivel locking system.

FIG. 17 is a perspective view of the pivoting rod connector 200 for coupling a first elongate stabilization member 202A and a second elongate stabilization member 202B using a first connector block 204A and a second connector block 204B, in accordance with embodiments of the present disclosure. The pivoting rod connector 200 includes the first connector block 204A and the second connector block 204B. The connector blocks 204A, 204B are linked by a swivel locking system 206. It is noted the swivel locking system 206 may be considered a pivot mechanism, for purposes of the present disclosure. The first connector block 204A includes a first rod slot 208A and the second connector block 204B includes a second rod slot 210B.

In some embodiments, the first connector block 204A may include a closure bore 210A and/or a closure bore 210B. The closure bore 210A and/or the closure bore 210B may be operable to receive a closure device 212A or a closure device 212B, respectively. In additional embodiments, the second connector block 204B may include a closure bore 210C and/or a closure bore 210D. The closure devices 212A-212D may be configured to engage the closure bores 210A-210D. For example, as discussed in detail herein, the closure bores 210A-210D may include threading that is complementary to threading on the closure devices 212A-212D.

In some examples, the elongate stabilization members 202A and 202B can include rigid rods or members. However, in other examples, the elongate stabilization members 202A and 202B can include other components including, but not limited to, flexible cords or members.

The pivoting rod connector 200 can be configured to hold the first and second elongate stabilization members 202A and 202B in a fixed angular relationship. The first and second elongate stabilization members 202A and 202B can be inserted into the rod slots 208A and 208B, respectively, and held therein via the closure devices 212A-212D, in a similar manner to other examples described herein. The closure devices 212A-212D can be inserted into the closure bores 210A-210D to axially lock the positions of the elongate stabilization members 202A and 202B relative to the connector blocks 204A and 204B, respectively. Additionally, a fastener 230 can be threaded into a fastener bore 222 to expand a pivot ball 218 within a pivot socket or ball socket 224, thereby locking the angular position between the first and second connector blocks 204A and 204B.

Figure 18:
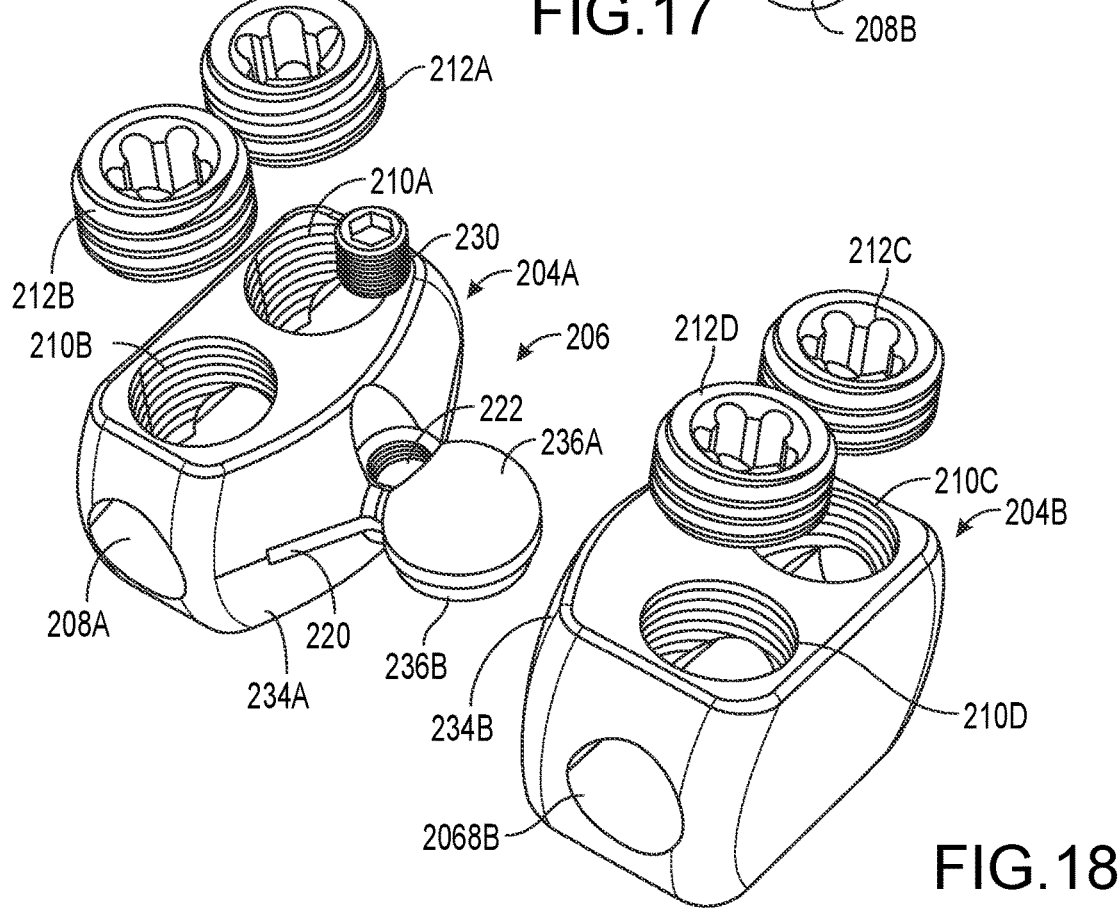
FIG. 18 is an exploded view of the rod connector of FIG. 17 showing a pair of connector blocks coupled via a ball connector of the swivel locking system.
Figure 20:
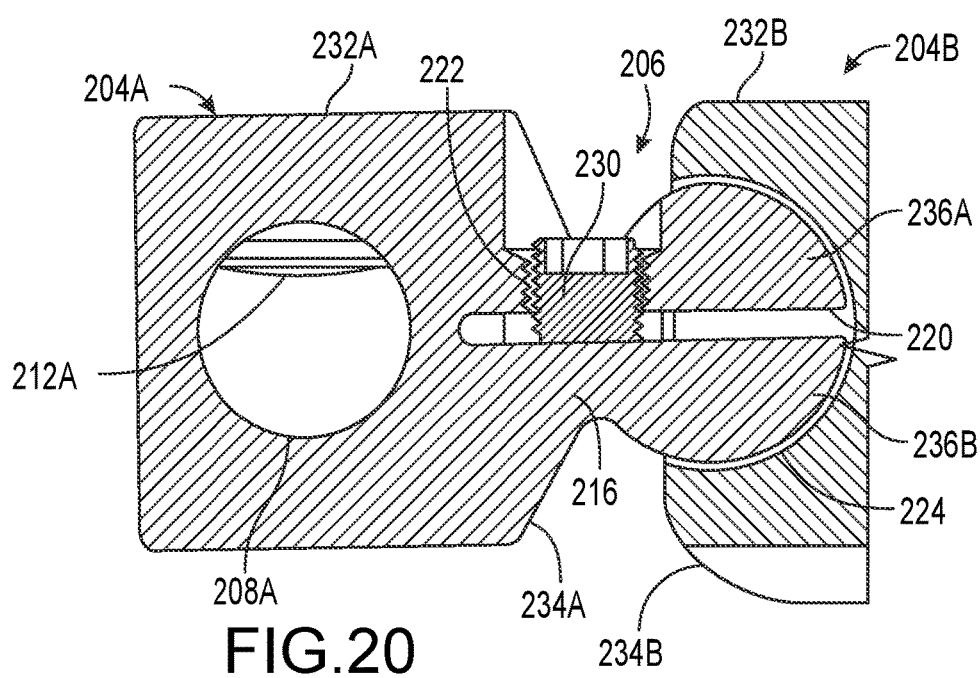
FIG. 20 is a cross-sectional view of the connector blocks of FIG. 19 taken at section 20-20 to show the ball connector in the ball socket.

FIG. 18 is an exploded view of the rod connector 200 of FIG. 17 showing the first and second connector blocks 204A and 204B couplable via a ball connector 214 and a ball socket 224 (e.g., as shown in FIG. 20), in accordance with embodiments of the present disclosure. In some embodiments, at least the ball connector 214 and the ball socket 224 form the swivel locking system 206. The ball connector 214 (and thus the first connector block 204A) can include a neck 216, a pivot ball 218, an expansion slot 220 and a fastener bore 222. The second connector block 204B can include the ball socket 224.

The connector block 204A can include a rectangular body having an upper surface 232A and a side surface 234A. The upper surface 232A can include the closure bores 210A and 210B. The neck 216 can extend from a side surface 234A. The rod slot 208A can extend from a front surface of the connector block 204A and exit through an aperture in a rear surface of the connector block 204A. In other embodiments, the rod slot 208A may only be within a portion of the length of the rectangular body, and does not exit the rear surface of the connector block 204A. The closure bores 210A and 210B can extend into or through the upper surface 232A to penetrate the rod slot 208A.

The connector block 204B can include a rectangular body having an upper surface 232B and a side surface 234B. The upper surface 232B can include the closure bores 210CA and 210D. The ball socket 224 can be located in the side surface 234B. The rod slot 208B can extend from a front surface of the connector block 204B and extend through an aperture in a rear surface of the connector block 204B. In other embodiments, the rod slot 208B may only be within a portion of the length of the rectangular body, and does not exit the rear surface of the connector block 204B. The closure bores 210C and 210D can extend into or through the upper surface 232B to penetrate the rod slot 208B.

It is noted that the connector blocks 204A, 204B are not limited to the rectangular body shape as shown in FIGS. 17-20, and may be other shapes having other two-dimensional cross-sections without departing from the scope of the present disclosure. For example, the connector block 204A can include a cylindrical shape of a body having a flat surface for the closure bores 210A and 210B and a curved surface wrapping around the rod slot 208A. By way of another example, the connector block 204B can include a cylindrical shape of a body having a flat surface for closure bores 210C and 210D and a curved surface wrapping around rod slot 208B. In addition, it is noted the connector block 204B need not have the same shape as the connector block 204A.

The side surfaces 234A and 234B can be curved or convex such that the connector blocks 204A and 204B can be permitted to move multi-directionally at the swivel locking system 206 formed by the ball connector 214 (e.g., the pivot ball 218) and the ball socket 224 to facilitate rotation. For example, with respect to FIG. 19, the connector blocks 204A and 204B can move medial-laterally relative to each other in the plane of FIG. 19 and anterior-posteriorly relative to each other into and out of the plane of FIG. 19, thereby providing multi-planar pivoting. Thus, the ball connector 214 (e.g., the pivot ball 218) and the ball socket 224 can form a ball joint (e.g., the swivel locking system 206) that allows for multiple degrees of freedom of movement between the connector block 204A and 204B while maintaining a fixed relationship in the axial direction extending across the centers of the ball connector 214 (e.g., the pivot ball 218) and the ball socket 224.

The pivot ball 218 can be configured for insertion into the ball socket 224. For example, the connector blocks 204A and 204B can be rotated such that the axes of the rod slot 208A and rod slot 208B are coplanar. As such, the connector blocks 204A and 204B can be moved laterally toward each other until the pivot ball 218 can be brought into engagement with the ball socket 224. The pivot ball 218 can be configured to compress to fit into the ball socket 224. In particular, an upper portion 236A and a lower portion 236B of the pivot ball 218 can be configured to be brought closer together at the expansion slot 220. Each of the upper portion 236A and the lower portion 236B can flex or deflect at the neck 216 to allow the pivot ball 218 to fit into the ball socket 224. With the pivot ball 218 seated within the ball socket 224, the connector blocks 204A and 204B can be permitted to pivot, rotate and swivel relative to each other. The swivel locking system 206 of the pivoting rod connector 200, including the fastener 230, can be employed to lock the relative positions of the connector blocks 204A and 204B.

The closure bores 210A-210D can be threaded to receive mating threading on the closure devices 212A-212D. The closure devices 212A-212D can include fasteners such as set screws having threads along outer diameter surfaces and a socket for a drive tool on upper surfaces. It is noted, however, that the interlocking of the closure bores 210A-210D and the closure devices 212A-212D is not limited to complementary threading, but instead may include any interlocking mechanism (e.g., tab-and-slot, protrusion-and-groove, or the like) that allows for the closure devices 212A-212D to be held in place in the closure bores 210A-210D and hold against the stabilization members 202A, 202B when in a particular angular orientation or an orientation within a range of angles.

In this regard, tightening of the closure devices 212A and 212B can therefore lock the axial position of the elongate stabilization member 202A relative to the connector block 204A, and tightening of the closure devices 212C and 212D can therefore lock the axial position of the elongate stabilization member 202B relative to the connector block 204B. Such tightening can facilitate precise implantation (e.g., at the desired orientation, distance, and/or angle) of the elongated stabilization members 202A and 202B by the surgeon.

Figure 19:
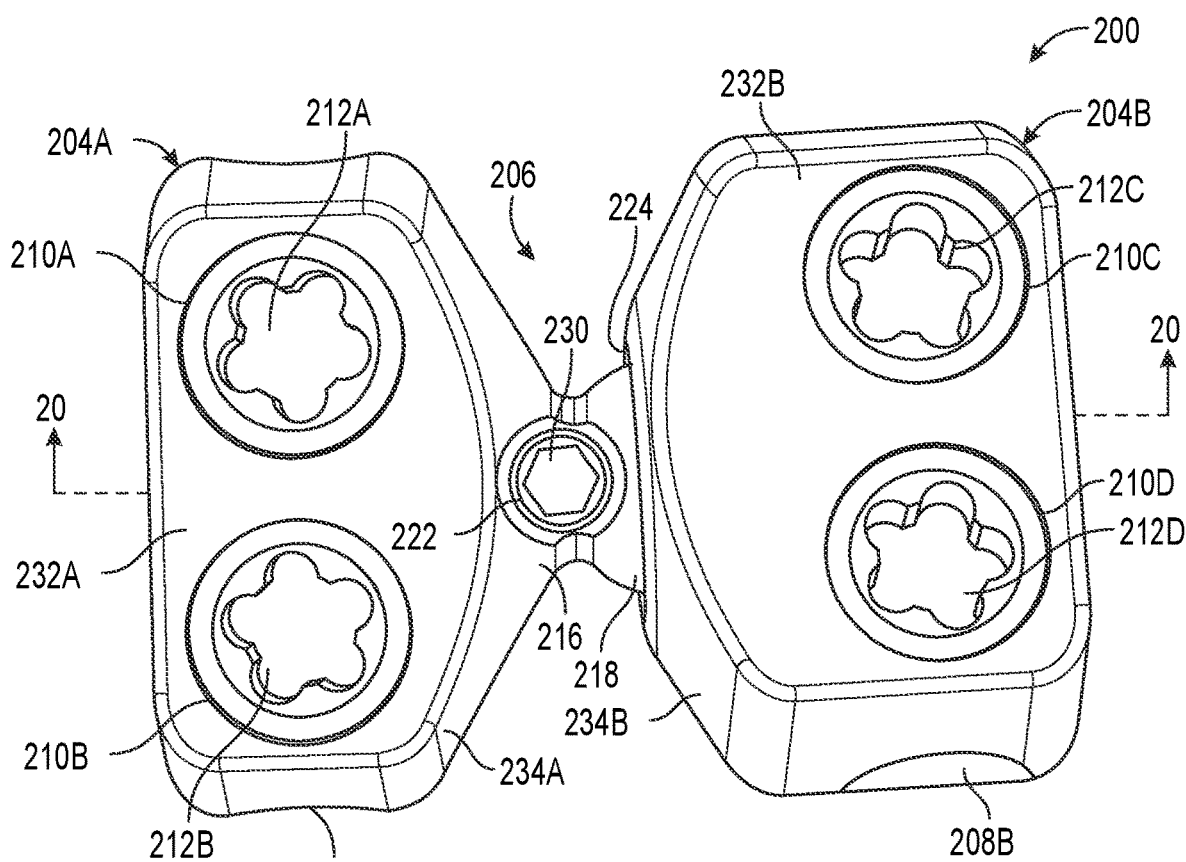
FIG. 19 is a top view of the pivoting rod connector of FIG. 17 showing the ball connector extended into a ball socket.

FIGS. 19 and 20 are example embodiments of the pivoting rod connector 200, in accordance with embodiments of the present disclosure. FIG. 19 is a top view of the pivoting rod connector 200 of FIG. 17 showing the pivot ball 218 extended into the ball socket 224. FIG. 20 is a cross-sectional view of the connector blocks 204A and 204B of FIG. 19 taken at section 20-20 to show the pivot ball 218 in the ball socket 224. FIGS. 19 and 20 are discussed concurrently.

In one example, the closure devices 212A and 212B (212B shown in FIG. 17) can be threaded into the closure bores 210A and 210B to axially lock the elongate stabilization member 202A. In particular, the closure devices 212A and 211B can push the elongate stabilization member 202A downward against the bottom of the rod slot 208A.

In another example, the closure devices 212C and 212D (212D shown in FIG. 17) can be threaded into the closure bores 210C and 210D to axially lock the elongate stabilization member 202B. In particular, the closure devices 212C and 212D can push the elongate stabilization member 202B downward against the bottom of the rod slot 208B.

The fastener 230 can include a threaded set screw having a threaded outer diameter and a socket on an upper surface to receive a drive tool. The fastener 230 can be threaded into the fastener bore 222 in the upper portion 236A to push down on the lower portion 236B through the slot 220, thereby pushing the upper portion 236A and the lower portion 236B away from each other and increasing the height or separation distance defined by the expansion slot 220. The upper portion 236A and the lower portion 236B can thereby be pushed into engagement with an interior surface of the ball socket 224 (when the pivot ball 218 is inserted into the ball socket 224) to immobilize the connector block 204A relative to the connector block 204B. The slot 220 can extend across the entirety of portions 236A and 236B and the neck 216 and into the side surface 234A to provide flexibility to the upper portion 236A and lower portion 236B. Thus, the fastener 230 engaging the upper portion 236A and the lower portion 236B via the fastener bore 222 to increase the separation distance defined by the expansion slot 220 may operate as a locking mechanism for the pivoting rod connector 200, for purposes of the present disclosure. It is noted, however, that the immobilizing of the pivot ball 218 in the ball socket 224 is not limited to the fastener 230 and the fastener bore 222 with complementary threading, but instead may include any interlocking mechanism (e.g., tab-and-slot, protrusion-and-groove, or the like) that allows for the pivot ball 218 to be immobilized within the ball socket 224, thus locking the connector blocks 204A, 204B in a particular angular orientation or an orientation within a range of angles.

In this regard, tightening of the fastener 230 can therefore lock the pivoted position between the connector block 204A and the connector block 204B. Such tightening can facilitate precise implantation (e.g., at the desired orientation, distance, and/or angle) of the elongated stabilization members 202A and 202B by the surgeon.

Although FIGS. 17-20 are illustrated as including closure bores 210A-210D and corresponding closure devices 212A-212D, it is noted that the pivoting rod connector 200 may include any number of closure bores and corresponding closure devices without departing from the scope of the present disclosure, to the extent the total length and/or width of the pivoting rod connector 200 does not inhibit the installation of the pivoting rod connector 200 into a patient, and/or does not weaken the coupling of the pivoting rod connector 200 to the stabilization members 202A, 202B. For example, the pivoting rod connector 200 may only include a closure bore 210A/closure device 212A on a first side, and a closure bore 210C/closure device 212C on a second side. By way of another example, each side of the pivoting rod connector 200 may include three or more closure bores 210/corresponding closure devices 212. Further, the sides of the pivoting rod connector 200 may include an unequal number of closure bores 210/corresponding closure devices 212. In addition, it is noted the closure bores 210 (and corresponding closure devices 212) may be the same or different diameters and/or lengths within the pivoting rod connector 200, without departing from the scope of the present disclosure.

FIG. 21 is an exploded view of a pivoting rod connector 250, in accordance with one or more embodiments of the present disclosure. It is noted aspects and/or components of the pivoting rod connector 250 may be shared with and/or combinable with one or more aspects and/or components of pivoting rod connectors 10, 100, 200, 280, 300, 350, 360, 370 without departing from the scope of the present disclosure, unless otherwise noted. In particular, the pivoting rod connector 250 should be understood to be a variation of the pivoting rod connector 200, without departing from the scope of the present disclosure. Although not shown, the pivoting rod connector 250 should be understood as configured to receive and engage with stabilization members (e.g., rigid rods or flexible cords) such as those described throughout the present disclosure, including at least in FIGS. 17-20.

The pivoting rod connector 250 has a first connector block 252A and a second connector block 252B. The connector blocks 252A, 252B are connected by a swivel locking system 254. It is noted the swivel locking system 254 may be considered a pivot mechanism, for purposes of the present disclosure. In some embodiments, the swivel locking system 254 may include a pivot ball 256 and a pivot socket or ball socket 258 that are offset to a side of each of the connector blocks 252A and 252B. For instance, the pivot ball 256 can include an upper portion 260A and a lower portion 260B separated by an expansion slot 262. The first connector block 252A includes a first rod slot 264A and the second connector block 204B includes a second rod slot 264B.

In some embodiments, the first connector block 252A may include a closure bore 266A and/or a closure bore 266B. The closure bore 266A and/or the closure bore 266B may be operable to receive a closure device 268A or a closure device 268B, respectively. In additional embodiments, the second connector block 252B can include a closure bore 266C and/or a closure bore 266D. The closure bore 266C and/or the closure bore 266D may be operable to receive a closure device 268C or a closure device 268D, respectively. For example, the closure bores 266A-266D may include, but are not limited to, threading that is complementary to threading on the closure devices 268A-268D.

The closure devices 268A-268D can be coupled to the closure bores 266A-266D to secure elongate stabilization members within the rod slots 264A, 264B in a fixed angular relationship as described herein (e.g., at least with respect to FIGS. 17-20). The rod slot 264A can extend from a front surface of the connector block 204A and exit through an aperture in a rear surface of the connector block 252A. In other embodiments, the rod slot 208A may only be within a portion of the length of the connector block 204A, and does not exit the rear surface of the connector block 204A. The rod slot 264B can include a blind end bore or closed bore into which the stabilization member is inserted. It is noted the bore may stop before the ball socket 258 (e.g., some amount of material forms a dividing wall or surface between the ball socket 258 and the bore within the connector block 204B), or that the bore and the ball socket 258 are interconnected. Where the bore and the ball socket 258 are interconnected, the pivot ball 256 may make contact with the elongate stabilization member within the rod slot 264B and the pivot ball 256 within the ball socket 258.

It is noted that the pivot ball 256 and the ball socket 258 can function similarly to the pivot ball 218 and the ball socket 224 of FIGS. 13-16. For example, the upper portion 260A and the lower portion 260B of the pivot ball 256 can flex to fit within the ball socket 258, thereby allowing the connector blocks 252A and 252B to pivot relative to each other in a multi-planar fashion. However, the pivot ball 256 can be configured to expand via operation of one or both of the closure devices 268A and 268B. In other examples, the pivot ball 256 can further or alternatively include a set screw similar to the fastener 230 of FIGS. 17-20. The expansion slot 262 can extend into the body of the connector block 252A aligned with portions forming the closure bore 266A to form an upper segment 270A and a lower segment 270B. The expansion slot 262 can extend all the way across a surface of the connector block 252A into which the rod slot 264A extends. As such, the closure device 268A can be threaded into the closure bore 266A to push against an elongate stabilization member, thereby simultaneously locking the elongate stabilization member and pushing upper segment 270A and lower segment 270B away from each other. The opposing motion of the upper segment 270A and the lower segment 270B can additionally produce an opposing motion for the upper portion 260A and the lower portion 260B of the pivot ball 256 to engage the pivot socket 258, thereby locking relative movement of the connector blocks 252A and 252B. Thus, the closure device 268A producing the opposing motion between the upper portion 260A and the lower portion 260B to increase the separation distance defined by the expansion slot 262 may operate as a locking mechanism for the pivoting rod connector 250, for purposes of the present disclosure. In this regard, at least the closure bore 266A and the closure device 268A, and/or the closure bore 266B and the closure device 268B may be considered a single locking mechanism for both a stabilization member inserted into the rod slot 264A and for the pivoting or angulation of the pivoting rod connector 250.

Although FIG. 21 is illustrated as including closure bores 266A-266D and corresponding closure devices 268A-268D, it is noted that the pivoting rod connector 250 may include any number of closure bores and corresponding closure devices without departing from the scope of the present disclosure, to the extent the total length and/or width of the pivoting rod connector 250 does not inhibit the installation of the pivoting rod connector 250 into a patient, and/or does not weaken the coupling of the pivoting rod connector 250 to the stabilization members (not shown). For example, as shown in FIG. 23, the pivoting rod connector 250 may only include a closure bore 266E/closure device 268E on a first side, and a closure bore 266F/closure device 268F on a second side. By way of another example, each side of the pivoting rod connector 250 may include three or more closure bores 266/corresponding closure devices 268. Further, the sides of the pivoting rod connector 250 may include an unequal number of closure bores 266/corresponding closure devices 268. In addition, it is noted the closure bores 266 (and corresponding closure devices 268) may be the same or different diameters and/or lengths within the pivoting rod connector 250, without departing from the scope of the present disclosure.

FIGS. 22A-22B illustrate a pivoting rod connector 280, in accordance with one or more embodiments of the present disclosure. It is noted aspects and/or components of the pivoting rod connector 280 may be shared with and/or combinable with one or more aspects and/or components of pivoting rod connectors 10, 100, 200, 250, 300, 350, 360, 370 without departing from the scope of the present disclosure, unless otherwise noted. In particular, the pivoting rod connector 280 should be understood to be a variation of the pivoting rod connectors 200 and 250, without departing from the scope of the present disclosure. Although not shown, the pivoting rod connector 280 should be understood as configured to receive and engage with stabilization members (e.g., rigid rods or flexible cords) such as those described throughout the present disclosure, including at least in FIGS. 17-20. FIGS. 22A and 22B are discussed concurrently.

FIG. 22A is an exploded view of the pivoting rod connector 280 having a first connector block 282A and a second connector block 282B, in accordance with one or more embodiments of the present disclosure. The connector blocks 282A, 282B are connected by a swivel locking system 284. In some embodiments, the swivel locking system includes a pivot ball 286 and a pivot socket or ball socket 288. It is noted the swivel locking system 284 may be considered a pivot mechanism, for purposes of the present disclosure. FIG. 22B is a cross-sectional view of the pivoting rod connector 280 of FIG. 22A taken to show an expansion slot 292 extending through the pivot ball 286 that are offset to a side of each of the connector blocks 282A and 282B. For instance, the pivot ball 286 can include an upper portion 290A and a lower portion 290B separated by the expansion slot 292. The first connector block 282A can include a rod slot 294A, and the second connector block 282B should be understood as including a second rod slot that extends into the page in FIG. 22B (although not shown).

In some embodiments, the first connector block 282A may include a closure bore 296A and/or a closure bore 296B. The closure bore 296A and/or the closure bore 296B may be operable to receive a closure device 298A or a closure device 298B, respectively. In additional embodiments, the second connector block 282B may include a closure bore 296C, and further may include a second closure bore (although not shown). The closure bore 296C and/or the second closure bore may be operable to receive a closure device 298C or a second closure device, respectively. In one non-limiting example, the connector block 282B can be configured similarly as the connector block 252B of FIG. 21, including with respect to closure bores and received closure devices.

In some embodiments, the connector block 282A may be configured similarly as the connector block 204A of FIG. 17. For example, the upper portion 290A and the lower portion 290B of the pivot ball 286 can flex to fit within the ball socket 288, thereby allowing the connector blocks 282A and 282B to pivot relative to each other in a multi-planar fashion. However, the pivot ball 286 can be configured to expand via operation of one or both of the closure devices 298A and 298B. In other examples, the pivot ball 286 can further or alternatively include a set screw similar to the fastener 230 of FIGS. 17-20. The slot 292 can extend into the body of the connector block 282A from a tip of the pivot ball 286 all the way to a curved sidewall 299 to penetrate into the rod slot 294A. The slot 292 can extend all the way across a surface of the connector block 282A from which pivot ball 286 extends (e.g., all the way across a width of the curved sidewall 299). The back side of the connector block 282A opposite the side where the pivot ball 286 extends from can flex when the closure devices 298A and 298B are threaded into the closure bores 296A and 296B. Thus, the closure device 298A producing the opposing motion between the upper portion 290A and the lower portion 290B to increase the separation distance defined by the expansion slot 292 may operate as a locking mechanism for the pivoting rod connector 280, for purposes of the present disclosure. In this regard, at least the closure bore 296A and the closure device 298A, and/or the closure bore 296B and the closure device 298B may be considered a single locking mechanism for both a stabilization member inserted into the rod slot 294A and for the pivoting or angulation of the pivoting rod connector 280.

Although FIGS. 22A-22B are illustrated as including closure bores 296A-296C (and the possibility of a fourth closure bore, per FIG. 21) and corresponding closure devices 298A-298C (and the possibility of a fourth closure device, per FIG. 21), it is noted that the pivoting rod connector 280 may include any number of closure bores and corresponding closure devices without departing from the scope of the present disclosure, to the extent the total length and/or width of the pivoting rod connector 280 does not inhibit the installation of the pivoting rod connector 280 into a patient, and/or does not weaken the coupling of the pivoting rod connector 280 to the stabilization members (not shown). For example, as shown in FIGS. 24A-24B, the pivoting rod connector 280 may only include a closure bore 296E/closure device 298E on a first side, and a closure bore 296F/closure device 298F on a second side. By way of another example, each side of the pivoting rod connector 280 may include three or more closure bores 296/corresponding closure devices 298. Further, the sides of the pivoting rod connector 200 may include an unequal number of closure bores 296/corresponding closure devices 298. In addition, it is noted the closure bores 296 (and corresponding closure devices 298) may be the same or different diameters and/or lengths within the pivoting rod connector 280 without departing from the scope of the present disclosure.

It is noted that FIGS. 16-24B provide a non-obvious benefit of a lower total height requirement for the pivoting rod connectors 200, 250, 280 with the components of the swivel locking system 206, 254, 284 extending from side surfaces and not from top or bottom surfaces of the block connectors 204A, 204B, 252A, 252B, 282A, 282B, respectively. In addition, it is noted that FIGS. 16-24B provide a non-obvious benefit of additional axes of rotation with the components of the swivel locking system 206, 254, 284, respectively.

FIGS. 25-28 in general illustrate a pivoting rod connector 300, in accordance with one or more embodiments of the present disclosure. It is noted aspects and/or components of the pivoting rod connector 300 may be shared with and/or combinable with one or more aspects and/or components of pivoting rod connectors 10, 100, 200, 250, 280, 350, 360, 370 without departing from the scope of the present disclosure, unless otherwise noted.

Figure 25:
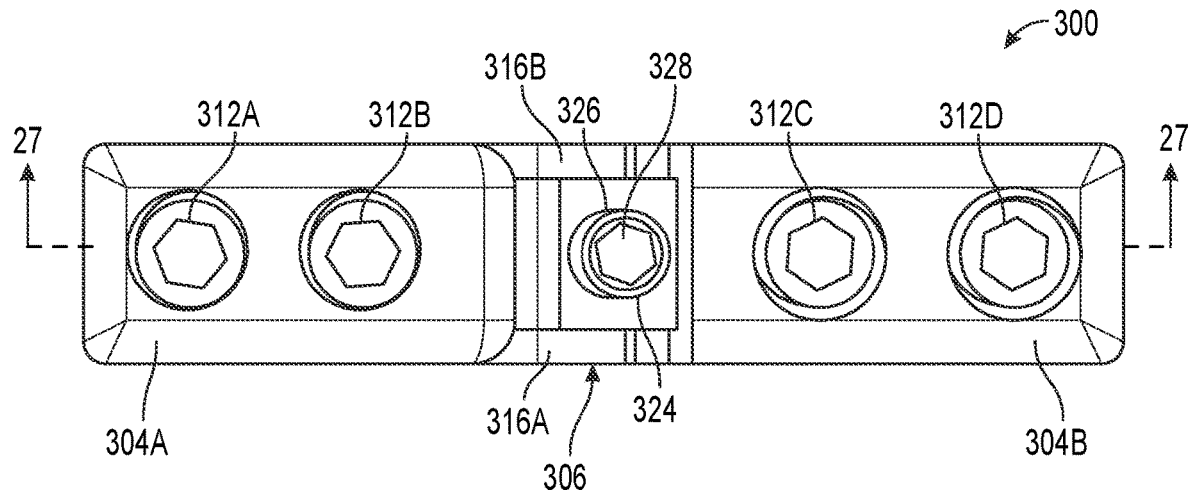
FIG. 25 is a top view of a pivoting rod connector coupling a pair of elongate stabilization members using connector blocks connected by a clamped locking system.
Figure 26:
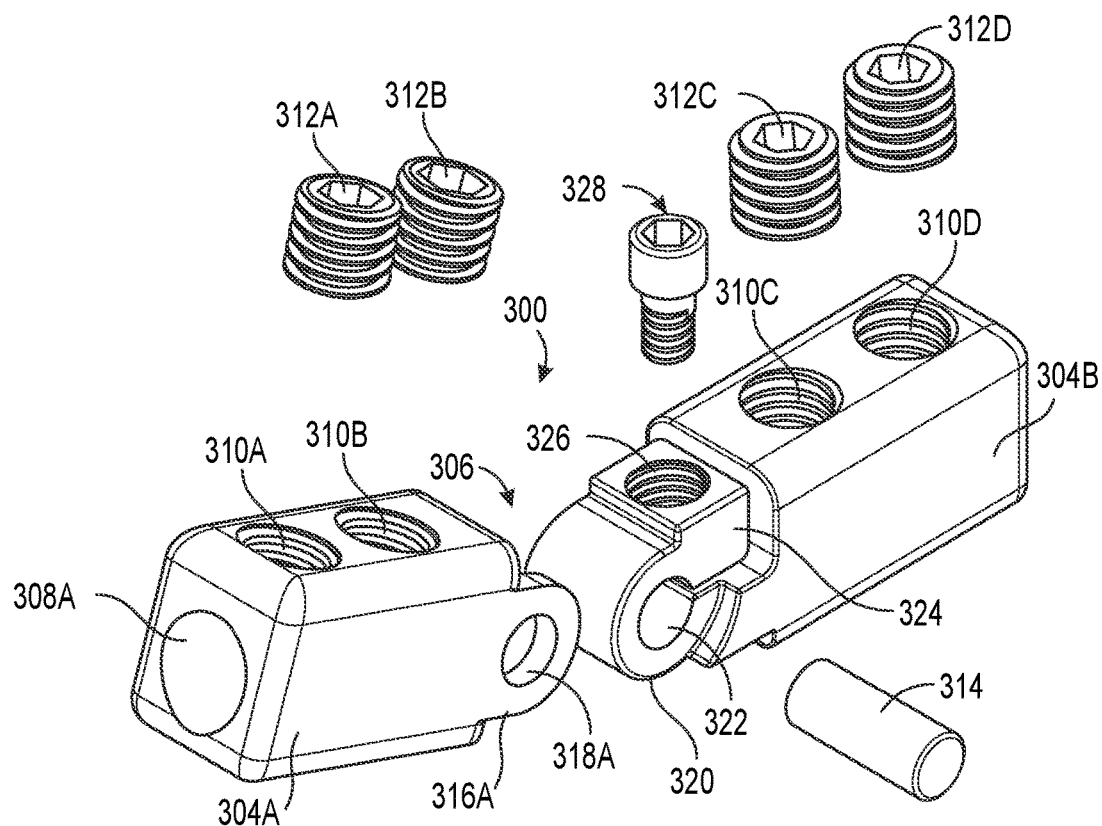
FIG. 26 is an exploded view of the pivoting rod connector of FIG. 25 showing the pair of connector blocks couplable via a tightenable hinge joint of the clamped locking system.
Figure 27:
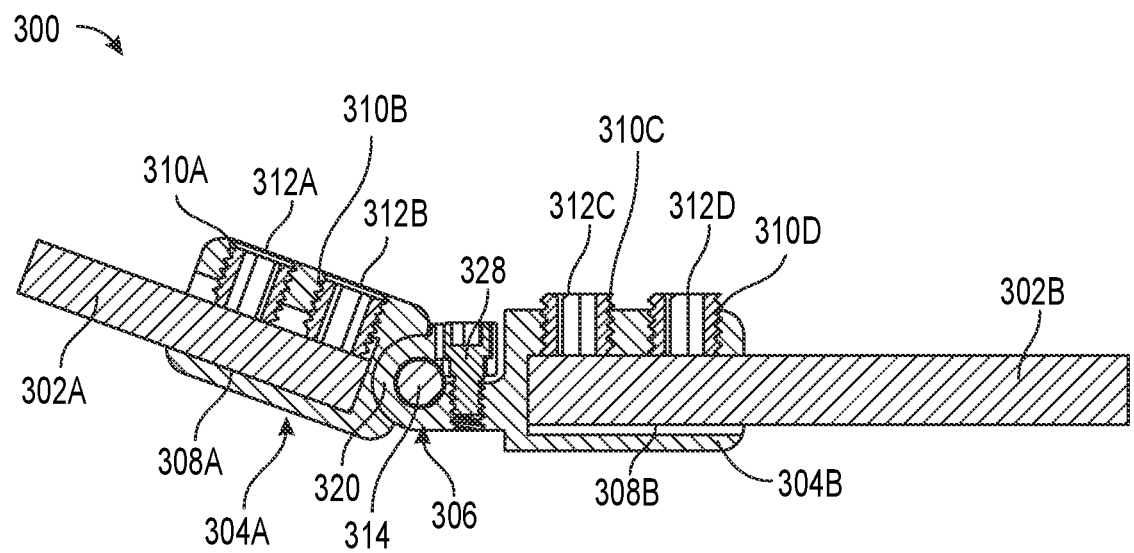
FIG. 27 is a cross-sectional view of the connector blocks of FIG. 25 taken at section 27-27 to show a clamped pivot pin of the tightenable hinge joint.

FIG. 25 is a top view of the pivoting rod connector 300 for coupling a first elongate stabilization member 302A (as shown in FIG. 27) and a second elongate stabilization member 302B (as shown in FIG. 27) using a first connector block 304A and a second connector block 304B, in accordance with embodiments of the present disclosure. The pivoting rod connector 300 includes the first connector block 304A and the second connector block 304B. The connector blocks 304A, 304B are linked by a clamped locking system 306 including a tightenable hinge joint. It is noted the clamped locking system 306 may be considered a pivot mechanism, for purposes of the present disclosure. FIG. 26 is an exploded view of the pivoting rod connector 300 of FIG. 25, in accordance with embodiments of the present disclosure. FIGS. 25 and 26 are discussed concurrently.

The first connector block 304A includes a rod slot 308A and the second connector block 304B includes a rod slot 308B (as shown in FIG. 27). In some embodiments, the first connector block 304A may include a closure bore 310A and/or a closure bore 310B. The closure bore 310A and/or the closure bore 310B may be operable to receive a closure device 312A or a closure device 312B, respectively. In additional embodiments, the second connector block 304B may include a closure bore 310C and/or a closure bore 310D. The closure bore 310C and/or the closure bore 310D may be operable to receive a closure device 312C or a closure device 312D, respectively. The closure devices 312A-312D may be configured to engage the closure bores 310A-310D. For example, the closure bores 310A-310D may include, but are not limited to, threading that is complementary to threading on the closure devices 312A-312D.

The pivoting rod connector 300 can be configured to hold the first and second elongate stabilization members 302A and 302B (as shown in FIG. 27) in a fixed angular relationship. The first and second elongate stabilization members 302A and 302B can be inserted into the rod slots 308A and 308B, respectively, and held therein via the closure devices 312A-312D. The closure devices 312A-312D can be inserted into the closure bores 310A-310D to axially lock the positions of the elongate stabilization members 302A and 302B relative to the connector blocks 304A and 304B, respectively. In this regard, tightening of the closure devices 312A and 312B can therefore lock the axial position of the elongate stabilization member 302A relative to the connector block 304A, and tightening of the closure devices 312C and 312D can therefore lock the axial position of the elongate stabilization member 302B relative to the connector block 304B. Such tightening can facilitate precise implantation (e.g., at the desired orientation, distance, and/or angle) of the elongated stabilization members 302A and 302B by the surgeon.

Figure 28:
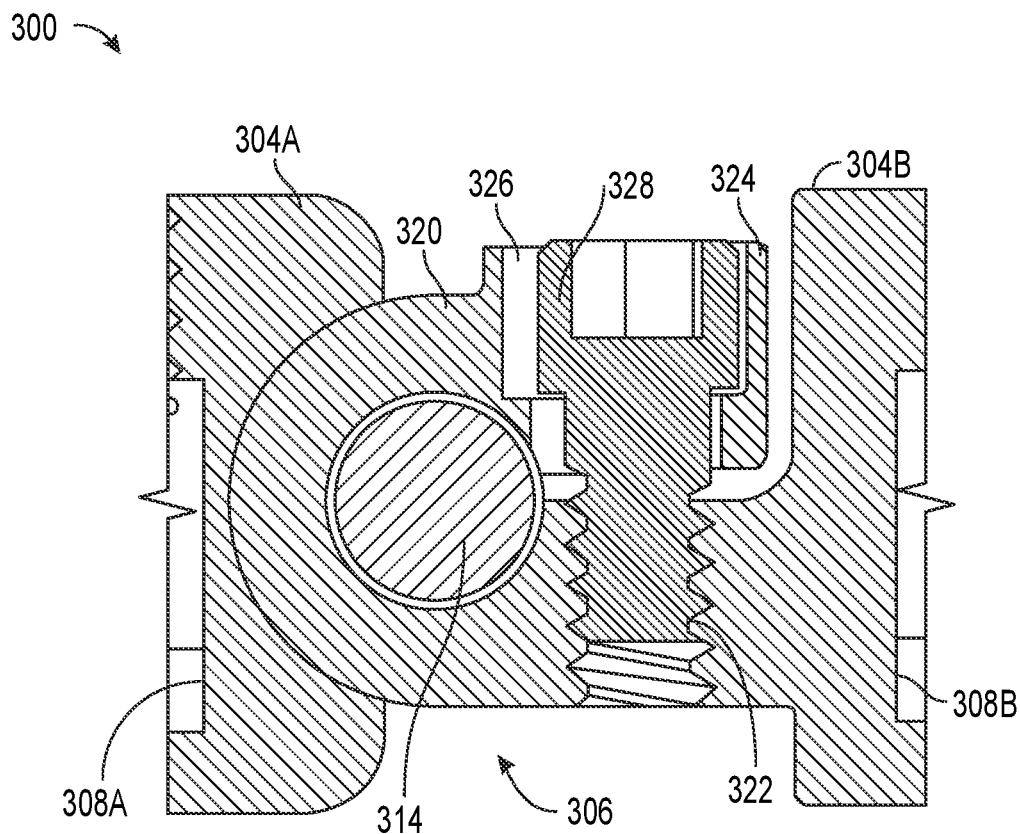
FIG. 28 is a close-up cross-sectional view of the clamped pivot pin of FIG. 27 partially wrapped by a flexible clamp.

FIG. 27 is a cross-sectional view of the connector blocks 304A and 304B of FIG. 25, in accordance with embodiments of the present disclosure. FIG. 28 is a close-up cross-sectional view of FIG. 27, in accordance with embodiments of the present disclosure. FIGS. 27 and 28 are discussed concurrently.

In some embodiments, the clamped locking system 306 may include a clamped pivot pin 314, arms 316A and 316B, and a flexible hinge arm 320. For example, the connector block 304A may include a first arm 316A and a second arm 316B, where each of the arms 316A and 316B can include a bore for receiving the pivot pin 314. For example, the arm 316A may include a bore 318A. The connector block 304B can include the flexible hinge arm 320. For example, the flexible hinge arm 320 may be curved to form a slotted bore 322. The flexible hinge arm 320 can be connected to a fastener block 324 having a fastener bore 326 for receiving a fastener 328.

The clamped pivot pin 314 is insertable into the arms 316A and 316B and the flexible hinge arm 320. The flexible hinge arm 320 can be tightened around the pivot pin 314 via the fastener 328 to lock the angular position between connector blocks 304A and 304B. As can be seen in FIG. 27, the connector block 304B can include a socket 332 for receiving the fastener 328. The bore 326 can be configured as a through-bore to allow the fastener 328 freely rotate therein. The socket 332 can include mating thread for thread on a distal end of fastener 328. Thus, the fastener 328 can be tightened into the socket 332 to pull the flexible hinge arm 320 into forcible engagement with the pivot pin 314 to immobilize the connector block 304A relative to the connector block 304B, thereby locking the angular position therebetween. Thus, the fastener 328 tightening the flexible hinge arm 320 about the clamped pivot pin 314 may operate as a locking mechanism for the pivoting rod connector 300, 350, for purposes of the present disclosure. In this regard, tightening of the fastener 328 can therefore lock the pivoted position between the connector block 304A and the connector block 304B. Such tightening can facilitate precise implantation (e.g., at the desired orientation, distance, and/or angle) of the elongated stabilization members 302A and 302B by the surgeon.

It is noted the pivoting rod connector 300 in FIGS. 25-28 provide a non-obvious benefit of keeping the stabilization members 302A, 302B in alignment along a single axis along a spine.

Figure 29:
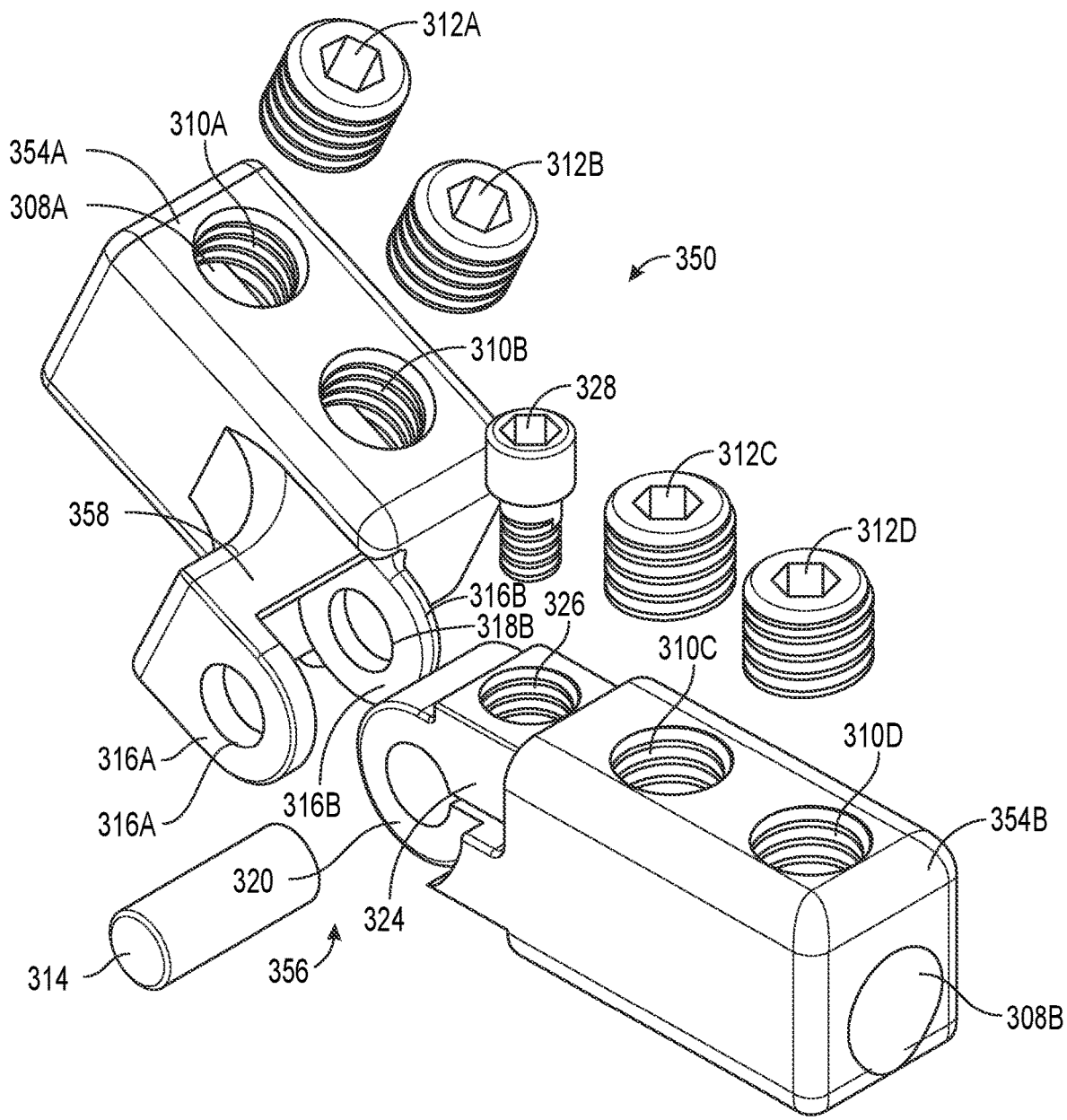
FIG. 29 is a perspective view of a second example or variation of FIG. 25 of a pivoting rod connector coupling a pair of elongate stabilization members using connector blocks connected by an offset clamped locking system.

FIG. 29 is a perspective view of pivoting rod connector 350, in accordance with one or more embodiments of the present disclosure. It is noted aspects and/or components of the pivoting rod connector 350 may be shared with and/or combinable with one or more aspects and/or components of pivoting rod connectors 10, 100, 200, 250, 280, 300, 360, 370 without departing from the scope of the present disclosure, unless otherwise noted. In particular, the pivoting rod connector 350 should be understood to be a variation of the pivoting rod connector 300, without departing from the scope of the present disclosure. Although not shown, the pivoting rod connector 350 should be understood as configured to receive and engage with stabilization members (e.g., rigid rods or flexible cords) such as those described throughout the present disclosure, including at least in FIGS. 25-28.

The pivoting rod connector 350 includes a first connector block 354A configured to receive a first elongate stabilization member (not shown) and a second connector block 354B configured to receive a second elongate stabilization member (not shown). The first connector block 354A and the second connector block 354B can be linked via an offset clamped locking system 356. It is noted the offset clamped locking system 356 may be considered a pivot mechanism, for purposes of the present disclosure.

It is noted that the connector block 354B can be configured similarly to the connector block 304B of FIGS. 25-28. In addition, it is noted that the connector block 354A can be configured similarly to the connector block 304A of FIGS. 25-28, except for the arm 316A can be positioned outside of the body of the connector block 304A via an extension 358 such that the axis of rod slot 308A can be offset from the axis of rod slot 308B.

Figure 30:
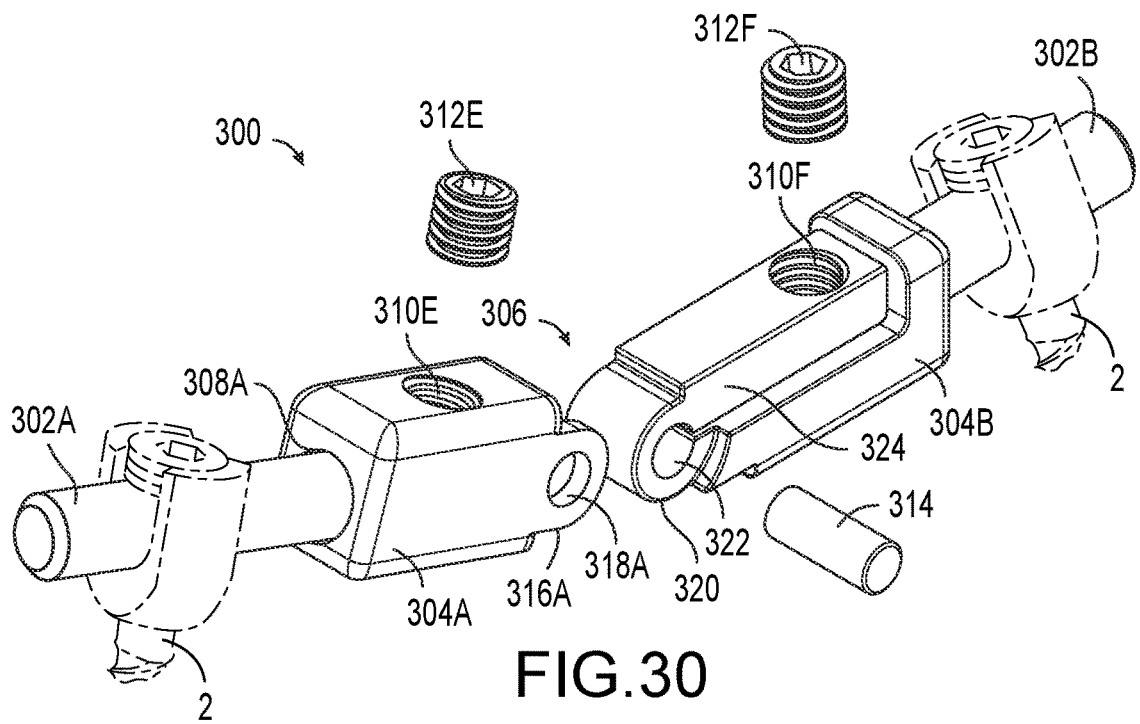
FIG. 30 is an exploded view of a second example or variation of FIG. 26 of a pivoting rod connector showing the pair of connector blocks couplable via a tightenable hinge joint of the clamped locking system.
Figure 31:
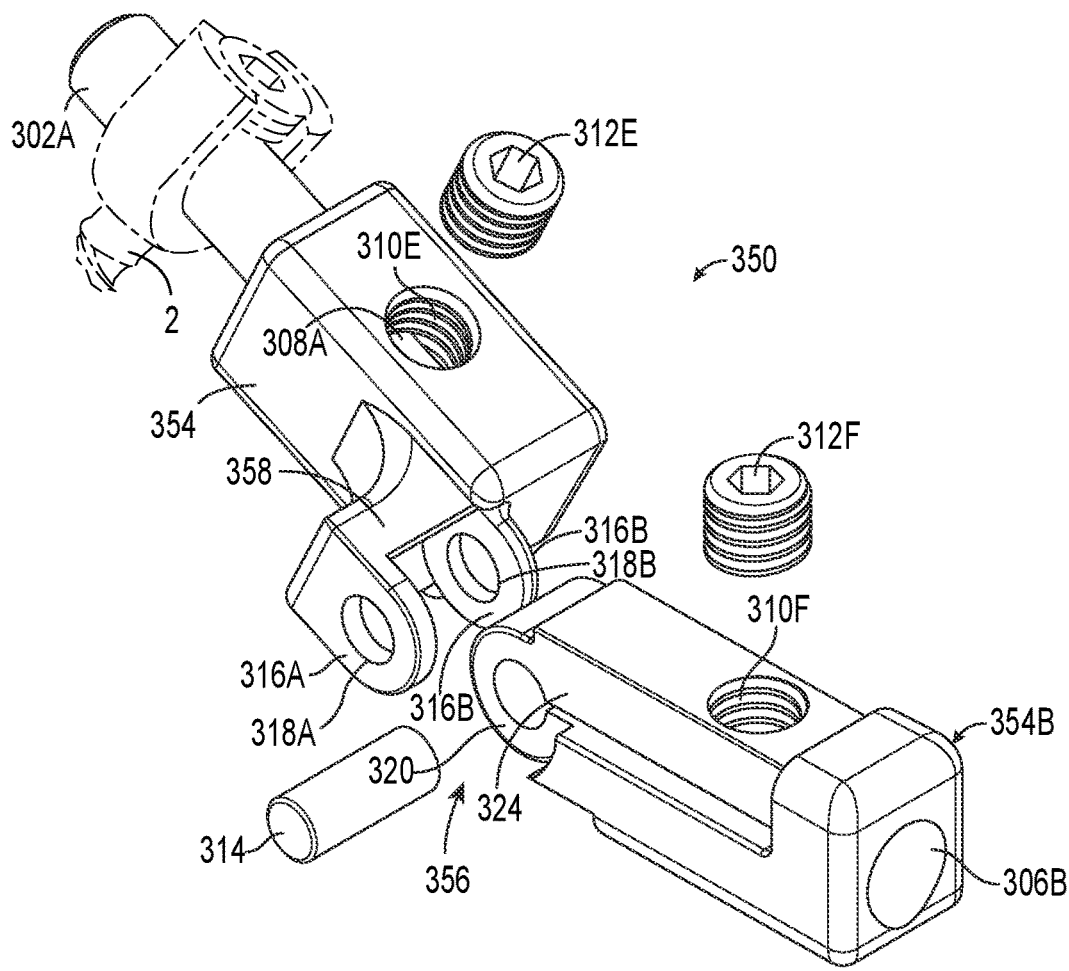
FIG. 31 is a perspective view of a second example or variation of FIG. 29 of a pivoting rod connector coupling a pair of elongate stabilization members using connector blocks connected by an offset clamped locking system.

Although FIGS. 25-29 are illustrated as including closure bores 310A-310D and corresponding closure devices 312A-312D, it is noted that the pivoting rod connector 300 may include any number of closure bores and corresponding closure devices without departing from the scope of the present disclosure, to the extent the total length and/or width of the pivoting rod connector 200 does not inhibit the installation of the pivoting rod connector 300 into a patient, and/or does not weaken the coupling of the pivoting rod connector 300 to the stabilization members 302A, 302B. For example, as illustrated in FIGS. 30 and 31, the pivoting rod connector 300 may only include a closure bore 310E/closure device 312E on a first side, and a closure bore 310F/closure device 312F on a second side. By way of another example, each side of the pivoting rod connector 300 may include three or more closure bores 310/corresponding closure devices 312. Further, the sides of the pivoting rod connector 300 may include an unequal number of closure bores 310/corresponding closure devices 312. In addition, it is noted the closure bores 310 (and corresponding closure devices 312) may be the same or different diameters and/or lengths within the pivoting rod connector 300, without departing from the scope of the present disclosure.

FIGS. 30 and 31 show an example embodiment where the flexible hinge arm 320 is extended along a length of the connector block 304B. In this example embodiment, the fastener bore 326 and the fastener 328 is removed, and both the clamping locking system 306 and the stabilization member 302B is locked by the single closure device 312F in the closure bore 310F. Thus, the closure device 320F tightening the flexible hinge arm 320 about the clamped pivot pin 314 may operate as a locking mechanism for the pivoting rod connector 300, 350, for purposes of the present disclosure. In this regard, at least the closure bore 312E and the closure device 312F may be considered a single locking mechanism for both the stabilization member 302B inserted into the rod slot 308B and for the pivoting or angulation of the pivoting rod connector 250 via the clamping locking system 306. It is noted, however, that FIGS. 30 and 31 only represent an example embodiment of a single locking mechanism employing the use of a closure device 312 instead of the fastener 328, and that other configurations are possible without departing from the scope of the present disclosure.

Figure 32:
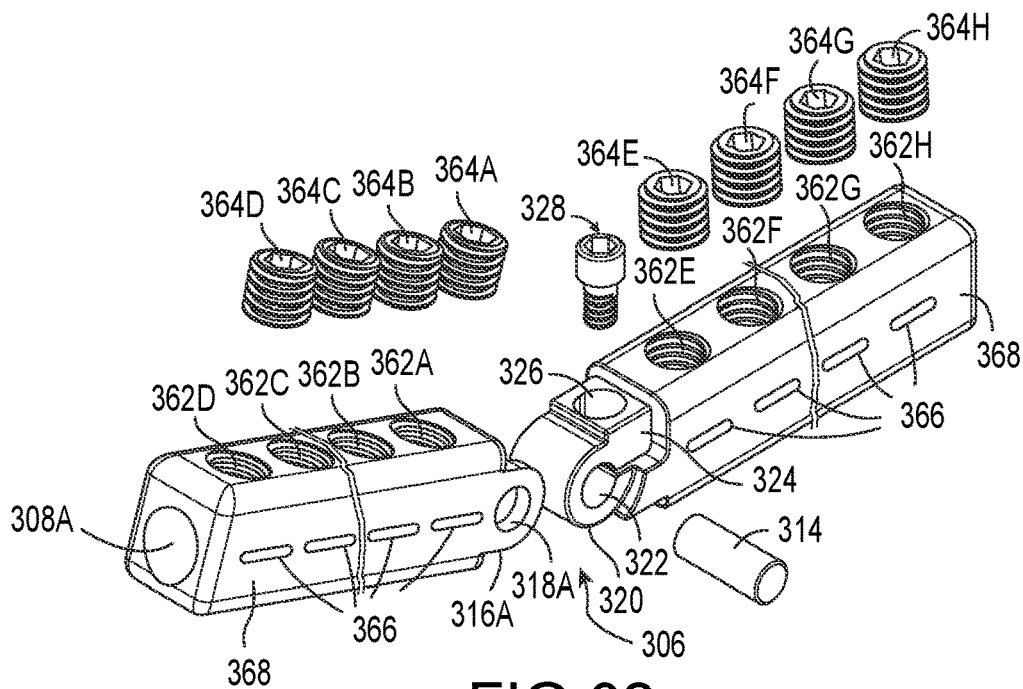
FIG. 32 is an exploded view of a third example or variation of FIG. 26 of a pivoting rod connector showing the pair of connector blocks couplable via a tightenable hinge joint of the clamped locking system.

FIG. 32 is a perspective view of pivoting rod connector 360, in accordance with one or more embodiments of the present disclosure. It is noted aspects and/or components of the pivoting rod connector 360 may be shared with and/or combinable with one or more aspects and/or components of pivoting rod connectors 10, 100, 200, 250, 280, 300, 350, 370 without departing from the scope of the present disclosure, unless otherwise noted. In particular, the pivoting rod connector 360 should be understood to be a variation of the pivoting rod connectors 300, without departing from the scope of the present disclosure. Although not shown, the pivoting rod connector 360 should be understood as configured to receive and engage with stabilization members (e.g., rigid rods or flexible cords) such as those described throughout the present disclosure, including at least in FIGS. 25-28.

The pivoting rod connector 360 includes a first connector block 304A configured to receive a first elongate stabilization member (e.g., as shown in FIG. 30) and a second connector block 304B configured to receive a second elongate stabilization member (e.g., as shown in FIG. 30). The first connector block 304A and the second connector block 304B can be linked via a clamped locking system 306.

The first connector block 304A includes a rod slot 308A and the second connector block 304B includes a second rod slot (not shown). In some embodiments, the first connector block 304A and the second connector block 304B may include one or more closure bores 362. The one or more closure bores 362 may be operable to receive corresponding closure devices 364. The closure devices 364 may be configured to engage the closure bores 362. For example, the closure bores 364 may include, but are not limited to, threading that is complementary to threading on the closure devices 362. In additional embodiments, the first connector block 304A and/or the second connector block 304B may include one or more slots or apertures 366 in one or more side surfaces 368.

The first connector block 304A and/or the second connector block 304B may be any length, and the first connector block 304A and/or the second connector block 304B may similarly include closure bores 362 and apertures 366 spaced along a portion or the entire length of the connector blocks 304A, 304B. In one non-limiting example, the first connector block 304A includes closure bores 362A-362D and closure devices 364A-364D, and the second connector block 304B includes closure bores 362E-362H and closure devices 364E-364H.

In some embodiments, the increased length of the connector blocks 304A, 304B may allow for the pivoting rod connector 360 to be utilized as a growing connector, such as where the pivoting rod connector 360 is installed in a child or other individual undergoing a growth phase. In a first configuration, a first subset of closure bores 362 and closure devices 364 (e.g., closure bores 362A/362B and closure bores 362E/362F, with corresponding closure devices 364) may be utilized to secure the stabilization members. As the child grows, the pivoting rod connector 360 may be accessed in a subsequent surgery and the closure devices may be loosened and removed. A tool such as a distraction instrument may engage the closure bores 362 and/or the apertures 366, sliding the pivoting rod connector 360 against the stabilization members to adjust the positioning of the connector blocks 304A, 304B relative to the stabilization members coupled to the spine of the patient (e.g., via the bone anchors). For example, the pivoting rod connector 360 may be adjusted so that less length of the stabilization members is within the pivoting rod connector 360 while the total length of the complete stabilization member/pivoting rod connector system is increased. Closure devices 364 may then be inserted into a second subset of closure bores 362 (e.g., closure bores 362B/362C and closure bores 362F/362G), to secure the stabilization members in the new position with increased length. In this regard, the pivoting rod connector 360 may grow with the patient, allowing for continued use of existing installations instead of needing to pull previous installation and re-implant. A benefit of the pivoting rod connector 360 being adjustable is that the pivot of the pivoting rod connector 360 may allow for a surgeon to adjust kyphosis angles during the surgery as well, in addition to adjusting for patient growth.

Figure 33:
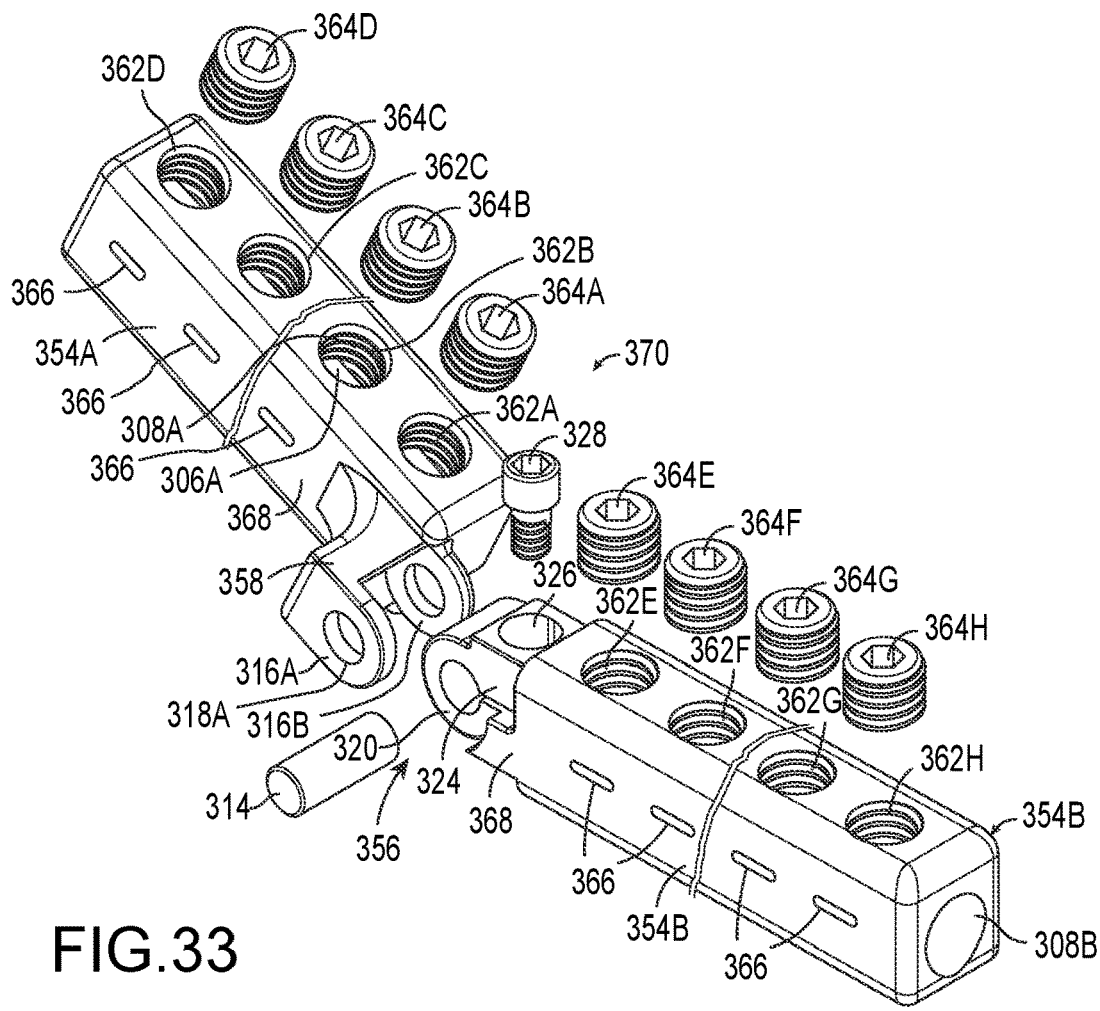
FIG. 33 is a perspective view of the pivoting rod connector of FIG. 32 coupling a pair of elongate stabilization members using connector blocks connected by an offset clamped locking system.

FIG. 33 is a perspective view of pivoting rod connector 370, in accordance with one or more embodiments of the present disclosure. It is noted aspects and/or components of the pivoting rod connector 370 may be shared with and/or combinable with one or more aspects and/or components of pivoting rod connectors 10, 100, 200, 250, 280, 300, 350, 360 without departing from the scope of the present disclosure, unless otherwise noted. In particular, the pivoting rod connector 370 should be understood to be a variation of the pivoting rod connector 350, without departing from the scope of the present disclosure. Although not shown, the pivoting rod connector 370 should be understood as configured to receive and engage with stabilization members (e.g., rigid rods or flexible cords) such as those described throughout the present disclosure, including at least in FIGS. 25-28.

The pivoting rod connector 370 includes a first connector block 354A configured to receive a first elongate stabilization member (as shown in FIG. 30) and a second connector block 354B configured to receive a second elongate stabilization member (as shown in FIG. 30). The first connector block 354A and the second connector block 354B can be linked via an offset clamped locking system 356. As discussed with respect to FIG. 32 and the pivoting rod connector 370, the pivoting rod connector 370 may be adjusted during surgery via the closure bores 364 and/or the slots 366 to adjust (e.g., reduce) a length of stabilization member within the connector blocks 354A, 354B to adjust (e.g., increase) a total length of the complete stabilization member/pivoting rod connector system.

It is noted that the single-bore and screw variations of the pivoting rod connectors 300 and 350 illustrated in FIGS. 30 and 31 may be similarly understood as reading on the pivoting rod connectors 360 and 370 of FIGS. 32 and 33, respectively, without departing from the scope of the present disclosure.

Although embodiments of the disclosure are directed to the apertures 366 being positioned in side surfaces of the connector blocks 304A, 304B of the pivoting rod connectors 300, 360 and the connector blocks 354A, 354B of the pivoting rod connectors 350, 370, it is noted herein that exterior side surfaces of any of the pivoting rod connectors 10, 100, 200, 250, 280 may be similarly modified to include the apertures 366 without departing from the scope of the present disclosure. In particular, this may be beneficial in the pivoting rod connectors 10, 100, 200, 250, 280 as respective stabilization members may pass through at least some of the connector blocks. This pass-through may allow for excess stabilization member length to be taken up at one end of the connector block or at the other end of the connector block as desired, to adjust (e.g., increase in length) the stabilization member/pivoting rod connector system to fit a patient as the patient experiences growth.

Operation and use of the pivoting rod connectors as described throughout the present disclosure may include one or more of the following steps. It is noted any of the embodiments, aspects, or components of the pivoting rod connectors 10, 100, 200, 250, 280, 300, 350, 360, 370 may be understood as being included in one or more of the following steps.

In a step, the method further includes, but is not limited to, securing a first stabilization member to a first connector block. The first stabilization member may be inserted into a first rod slot of the first connector block. A first closure device may be inserted into a first closure bore of the first connector block. The first closure device may engage the first stabilization member to secure the first stabilization member within the first rod slot.

In a step, the method further includes, but is not limited to, securing a second stabilization member to a second connector block. The second stabilization member may be inserted into a second rod slot of the second connector block. A second closure device may be inserted into a second closure bore of the second connector block. The second closure device may engage the second stabilization member to secure the second stabilization member within the second rod slot.

In a step, the method further includes, but is not limited to, adjusting a pivot mechanism coupling the first connector block and the second connector block to adjust an angular position between the first stabilization member and the second stabilization member. In some embodiments, the pivot mechanism may include the wedged locking system 16, the threaded locking system 106, the swivel locking systems 206, 254, 284, or the clamped locking systems 306, 356, as described throughout the present disclosure.

In a step, the method further includes, but is not limited to, locking the pivot mechanism to inhibit angulation between the first stabilization member and the second stabilization member. In some embodiments, locking the pivot mechanism may include preventing additional angulation within the wedged locking system 16, the threaded locking system 106, the swivel locking systems 206, 254, 284, or the clamped locking systems 306, 356, as described throughout the present disclosure.

In a step, the method further includes, but is not limited to, disengaging at least one of the first connector block from the first stabilization member and the second connector block from the second stabilization member when the pivoting rod connector is in a first position. The method further includes, but is not limited to, adjusting the positioning of at least one of the first connector block relative to the first stabilization member and the second connector block relative to the second stabilization member. For example, the adjustment may occur via a distraction tool engaging a closure bore and/or an aperture 366 in the connector blocks. The method further includes, but is not limited to, re-engaging the at least one of the first connector block to the first stabilization member and the second connector block to the second stabilization member when the pivoting rod connector is in a second, different position. It is noted this non-limiting step may be performed without disengaging the stabilization members from the patient (e.g., from the bone anchors within the spine of the patient).

While the steps have been discussed and illustrated in relation to a particular sequence of events, it should be appreciated that changes, additions, and omissions to this sequence can occur without materially affecting the operation of the disclosed embodiments, configuration, and aspects The systems, devices and methods discussed in the present application can be useful in implanting elongate stabilization members, such as rigid rods used in spinal stabilization procedures. The pivoting rod connectors of the present disclosure can provide angular adjustment between two rods being connected in an end-to-end fashion. The rods can be connected in an axially aligned configuration or an axially offset configuration. The pivoting rod connectors can facilitate mono-axial rotation, e.g., angular rotation of the rods in a single plane, or poly-axial rotation in many different planes. The pivoting rod connectors can include locking elements or fasteners that can be activated to fix the axial position of the rods and the angular orientation of the rods. In examples, separate locking elements can be provided for axial and angular fixation. In examples, locking elements that provide axial fixation can additionally simultaneously provide angular fixation. The locking elements can be accessed in convenient locations on the connectors to facilitate ease of use during a procedure.

Each of the following non-limiting examples may stand on its own, or may be combined in various permutations or combinations with one or more of the other examples.

Example 1 is a pivoting rod connector for spinal stabilization members, the pivoting rod connector comprising: a first connector block comprising: a first rod slot for receiving a first stabilization member; and a first closure bore for receiving a first closure device, wherein engaging the first stabilization member with the first closure device secures the first stabilization member within the first rod slot; a second connector block comprising: a second rod slot for receiving a second stabilization member; and a second closure bore for receiving a second closure device, wherein engaging the second stabilization member with the second closure device secures the second stabilization member within the second rod slot; and a pivot mechanism connecting the first connector block and the second connector block, wherein the pivot mechanism is configured to allow for angulation between the first rod slot and the second rod slot, and wherein the pivoting rod connector is lockable to inhibit angulation of the pivot mechanism.

In Example 2, the subject matter of Example 1 optionally includes wherein the pivot mechanism comprises: a wedged pivot pin extending from a first side surface of the first connector block; and a pivot socket positioned within a second side surface of the second connector block and configured to exit into the second rod slot, wherein engaging the second stabilization member with the second closure device pushes the second stabilization member inserted into the second rod slot against the wedged pivot pin when the wedged pivot pin is inserted into the pivot socket, wherein the second rod slot comprises a surface that is angled to push the second stabilization member against the wedged pivot pin as the second closure device engages the second stabilization member, and wherein the pushing of the second stabilization member against the wedged pivot pin inhibits angulation between the first rod slot and the second rod slot as a locking mechanism.

In Example 3, the subject matter of Example 2 optionally includes wherein the wedged pivot pin comprises a pair of protruding lobes and the pivot socket comprises a pair of mating recessed lobes, wherein the protruding lobes on the first connector block and the recessed lobes on the second connector block allow the first connector block to be uncoupled from the second connector block when the pivoting rod connector is in a first orientation, and wherein the protruding lobes on the first connector block and the recessed lobes on the second connector block cause the first connector block to interlock with the second connector block when the pivoting rod connector is in a second, different orientation.

In Example 4, the subject matter of Example 1 optionally includes wherein the pivot mechanism comprises: a threaded pivot pin configured to engage a first bore in the first connector block; and a second bore in the second connector block, wherein engaging the first stabilization member with the first closure device pushes the first stabilization member inserted into the first rod slot against the threaded pivot pin when the threaded pivot pin is inserted into the first bore, wherein the pushing of the first stabilization member against the wedged pivot pin inhibits angulation between the first rod slot and the second rod slot as a locking mechanism.

In Example 5, the subject matter of Example 4 optionally includes wherein the threaded pivot pin comprises: a head configured to engage an exterior surface of the first connector body; a smooth portion configured to pass through the first bore and around which the first connector body is configured to rotate; and a threaded portion configured to engage threading within the second bore of the second connector block, wherein the first stabilization member engages the smooth portion of the threaded pivot pin when the threaded pivot pin is inserted into the first bore and the first closure device engages the first stabilization member.

In Example 6, the subject matter of Example 1 optionally includes wherein the pivot mechanism comprises: a ball connector including a pivot ball extending from the first connector block; and a ball socket positioned on the second connector block, wherein the ball socket is configured to receive the pivot ball to allow multi-planar angulation between the first and second connector bodies.

In Example 7, the subject matter of Example 6 optionally includes wherein the pivot ball includes an upper portion and a lower portion separated by an expansion slot, wherein increasing a separation distance defined by the expansion slot causes the upper portion and the lower portion to engage with the ball socket when the pivot ball is inserted into the ball socket, and wherein the engaging of the upper portion and the lower portion of the pivot ball with the ball socket inhibits angulation between the first rod slot and the second rod slot as a locking mechanism.

In Example 8, the subject matter of Example 7 optionally includes wherein the ball connector further includes a neck configured to couple the pivot ball to the first connector block, wherein the neck includes a fastener bore configured to receive a fastener, wherein the fastener bore includes threading in the upper portion and the lower portion of the pivot ball, and wherein engaging the fastener bore with the fastener increases the separation distance defined by the expansion slot to inhibit angulation between the first rod slot and the second rod slot as the locking mechanism.

In Example 9, the subject matter of Example 7 optionally includes wherein the expansion slot extends into the first connector block and intersects with the first closure bore, and wherein engaging the first closure bore with the first closure device increases the separation distance defined by the expansion slot to inhibit angulation between the first rod slot and the second rod slot as the locking mechanism.

In Example 10, the subject matter of Example 1, optionally includes wherein the pivot mechanism comprises: a pivot pin; at least one bore on the first connector block that is operable to receive the pivot pin; and a flexible hinge arm on the second connector block that is operable to receive a pivot pin, wherein engaging the pivot pin with the flexible hinge arm inhibits angulation between the first rod slot and the second rod slot as a locking mechanism.

In Example 11, the subject matter of Example 10 optionally includes wherein the flexible hinge arm includes a fastener bore configured to receive a fastener, wherein engaging the fastener bore with the fastener causes the flexible hinge arm to engage the pivot pin to inhibit angulation between the first rod slot and the second rod slot as the locking mechanism.

In Example 12, the subject matter of Example 1 optionally includes wherein at least one of the first connector block and the second connector block includes one or more slots on a side surface that are usable for adjustment of at least one of the first connector block relative to the first stabilization member and the second connector block relative to the second stabilization member when at least one of the first stabilization member and the second stabilization member are fixed in position to a spine of a patient.

Example 13 is a method of connecting stabilization members in a spinal procedure, the method comprising, but is not limited to, securing a first stabilization member in a first connector block by engaging the first stabilization member inserted in a first rod slot of the first connector block with a first closure device inserted in a first closure bore of the first connector block; securing a second stabilization member to a second connector block by engaging the second stabilization member inserted in a second rod slot of the second connector block with a second closure device inserted in a second closure bore of the second connector block; adjusting a pivot mechanism connecting the first connector block and the second connector block to adjust an angular position between the first stabilization member and the second stabilization member; and locking the pivot mechanism to inhibit angulation between the first stabilization member and the second stabilization member.

In Example 14, the subject matter of Example 13 optionally includes wherein the locking the pivot mechanism to inhibit angulation between the first stabilization member and the second stabilization member comprises, but is not limited to: inserting a wedged pivot pin of the first connector block into a pivot socket of a second connector block, wherein the wedged pivot pin and the pivot socket form the pivot mechanism; and engaging a wall of the first connector block and the wedged pivot pin with the second stabilization member following engagement of the second stabilization member with the second closure device.

In Example 15, the subject matter of Example 13 optionally includes wherein the locking the pivot mechanism to inhibit angulation between the first stabilization member and the second stabilization member comprises, but is not limited to: inserting a pivot pin into a first bore in the first connector block and a second bore in the second connector block, wherein the pivot pin, the first bore, and the second bore form the pivot mechanism; and engaging a pivot pin with the first stabilization member following engagement of the first stabilization member with the first closure device.

In Example 16, the subject matter of Example 13 optionally includes wherein the locking the pivot mechanism to inhibit angulation between the first stabilization member and the second stabilization member comprises, but is not limited to: inserting a pivot ball of a ball connector of the first connector block into a ball socket in the second connector block, wherein the ball connector and the ball socket form the pivot mechanism; and engaging the ball socket with the pivot ball by increasing a separation distance defined by an expansion slot between an upper portion and a lower portion of the pivot ball.

In Example 17, the subject matter of Example 16 optionally includes wherein the separation distance defined by the expansion slot between the upper portion and the lower portion of the pivot ball is increased by either: engaging a fastener bore in a neck of the ball connector with a fastener to increase the defined separation distance, or engaging the first closure bore with the first closure device to increase the defined separation distance, where the expansion slot extends into the first connector block and intersects the first closure bore.

In Example 18, the subject matter of Example 13 optionally includes wherein the locking the pivot mechanism to inhibit angulation between the first stabilization member and the second stabilization member comprises, but is not limited to: inserting a pivot pin into at least one bore in the first connector block and a flexible hinge arm on the second connector block, wherein the pivot pin, the at least one bore, and the flexible hinge form the pivot mechanism; and engaging the pivot pin with the flexible hinge arm.

In Example 19, the subject matter of Example 13 optionally includes further comprising, but is not limited to: disengaging at least one of the first connector block from the first stabilization member and the second connector block from the second stabilization member when the pivoting rod connector is in a first position; adjusting the positioning of at least one of the first connector block relative to the first stabilization member and the second connector block relative to the second stabilization member; and re-engaging the at least one of the first connector block to the first stabilization member and the second connector block to the second stabilization member when the pivoting rod connector is in a second, different position, wherein the disengaging, adjusting, and re-engaging occurs when at least one of the first stabilization member and the second stabilization member are fixed in position to a spine of a patient.

Example 20 is a pivoting rod connector for spinal stabilization members, the pivoting rod connector comprising: a first stabilization member; a second stabilization member; and a pivoting rod connector, the pivoting rod connector comprising: a first connector block comprising: a first rod slot for receiving a first end of the first stabilization member; and a first closure bore for receiving a first closure device, wherein engaging the first end of the first stabilization member with the first closure device secures the first stabilization member within the first rod slot; a second connector block comprising: a second rod slot for receiving a second end of a second stabilization member; and a second closure bore for receiving a second closure device, wherein engaging the second end of the second stabilization member with the second closure device secures the second stabilization member within the second rod slot; and a pivot mechanism connecting the first connector block and the second connector block, wherein the pivot mechanism is configured to allow for angulation between the first rod slot and the second rod slot, and wherein the pivoting rod connector is lockable to inhibit angulation of the pivot mechanism.

Example 21 is a pivoting rod connector for spinal stabilization members, the pivoting rod connector comprising: a first connector body comprising: a first rod slot for receiving a stabilization member; and a first closure bore for receiving a closure device; a second connector body comprising: a second rod slot for receiving a stabilization member; and a second closure bore for receiving a closure device; a pivot mechanism connecting the first connector body and the second connector body to allow for angulation between the first and second rod slots; and a locking mechanism to inhibit angulation of the pivot mechanism; wherein operation of the locking mechanism is operable via insertion of a closure device in at least one of the closure bores to secure a stabilization member therein.

In Example 22, the subject matter of Example 21 optionally includes wherein the locking mechanism is configured to push a stabilization member inserted into one of the first and second slots to activate the locking mechanism.

In Example 23, the subject matter of any one or more of Examples 21-22 optionally include wherein the locking mechanism comprises a wedge member configured to bind the pivot mechanism.

In Example 24, the subject matter of Example 23 optionally includes wherein: the pivot mechanism comprises: a socket extending into the first connector body to penetrate the first rod slot; and a pivot post extending from the second connector body into the socket; and the locking mechanism comprises: an end surface of the pivot post extending into the first rod slot; wherein a stabilization member inserted into the first rod slot comprises the wedge.

In Example 25, the subject matter of Example 24 optionally includes wherein the first rod slot comprises a flat surface angled to push a stabilization member toward the end surface.

In Example 26, the subject matter of any one or more of Examples 24-25 optionally include wherein the pivot post comprises a pair of lobes and the socket comprises a pair of mating lobes to allow the first and second connector bodies to be interlocked.

In Example 27, the subject matter of any one or more of Examples 21-26 optionally include wherein: the pivot mechanism comprises a pivot pin connected to the first connector body such that the second connector body is pivotable on the pivot pin; and the locking mechanism comprises a closure device configured to push an elongate stabilization member into engagement with the pivot pin.

In Example 28, the subject matter of Example 27 optionally includes wherein the pivot pin comprises: a threaded portion configured to engage the first connector body; a smooth portion around which the second connector body is configured to rotate; and a head having a diameter larger than the smooth portion to pin the second connector body against the first connector body.

In Example 29, the subject matter of any one or more of Examples 27-28 optionally include wherein rod slot includes an axial lobe to allow the pivot pin to intersect a stabilization member within the rod slot.

In Example 30, the subject matter of any one or more of Examples 21-29 optionally include wherein the locking mechanism comprises an expandable portion of the pivot mechanism.

In Example 31, the subject matter of any one or more of Examples 29-30 optionally include wherein: the pivot mechanism comprises: a pivot ball extending from the first connector body; and a pivot socket positioned on the second connector body, wherein the pivot socket is configured to receive the pivot ball to allow multi-planar angulation between the first and second connector bodies; and the locking mechanism comprises: an expansion slot in the first connector body positioned to split the pivot ball into deflectable portions; wherein a closure device is configured to push apart the deflectable portions to lock the pivot ball into engagement with the pivot socket.

In Example 32, the subject matter of Example 31 optionally includes wherein the expansion slot extends into the first connector body parallel to a surface in which the first closure bore is located to intersect a central axis of the first closure bore.

Example 33 is a method of connecting stabilization members in a spinal procedure, the method comprising: connecting a first connector body to a first stabilization member; connecting a second connector body to a second stabilization member; adjusting a pivot mechanism connecting the first connector body and the second connector body to adjust an angular position between the first stabilization member and the second stabilization member; and adjusting a closure device to simultaneously lock the first stabilization member in the first connector body and lock a position of the first connector body relative to the second connector body.

In Example 34, the subject matter of Example 33 optionally includes wherein adjusting the closure device to simultaneously lock the first stabilization member in the first connector body and lock a position of the first connector body relative to the second connector body comprises: wedging the first stabilization member against a wall of the first connector body and a wedge face of the second connector body extending into the first connector body.

In Example 35, the subject matter of Example 34 optionally includes wherein wedging the first stabilization member against a wall of the first connector body and a wedge face of the second connector body extending into the first connector body comprises: pushing the first stabilization member downward with the closure device; and pushing the first stabilization member laterally with the wall of the first connector body, the wall of the first connector body comprising an angled surface of a slot for the first stabilization member.

In Example 36, the subject matter of any one or more of Examples 33-35 optionally include wherein: adjusting a pivot mechanism connecting the first connector body and the second connector body to adjust an angular position between the first stabilization member and the second stabilization member comprises: rotating the first connector body on a pivot pin extending from the second connector body; and adjusting the closure device to simultaneously lock the first stabilization member in the first connector body and lock a position of the first connector body relative to the second connector body comprises: pressing the first stabilization member against the pivot pin with the closure device.

In Example 37, the subject matter of Example 36 optionally includes tightening the pivot pin into the second connector body to bring a head of the pivot pin into engagement with the first connector body.

In Example 38, the subject matter of any one or more of Examples 33-37 optionally include wherein adjusting the closure device to simultaneously lock the first stabilization member in the first connector body and lock a position of the first connector body relative to the second connector body comprises: expanding a pivot coupler connecting the first connector body and the second connector body.

In Example 39, the subject matter of Example 38 optionally includes wherein expanding the pivot coupler connecting the first connector body and the second connector body comprises: adjusting the closure device to push first and second portions of a pivot ball into engagement with a pivot socket.

In Example 40, the subject matter of Example 39 optionally includes expanding a portion of the first connector body via pushing of the closure device on the first stabilization member.

Example 41 is a pivoting rod connector for spinal stabilization members, the pivoting rod connector comprising: a first connector body comprising: a first rod slot for receiving a stabilization member; and a first closure bore for receiving a closure device; a second connector body comprising: a second rod slot for receiving a stabilization member; and a second closure bore for receiving a closure device; a pivot mechanism connecting the first connector body and the second connector body to allow for angulation between the first and second rod slots, the pivot mechanism comprising: a pivot ball extending from the first connector body; and a pivot socket positioned on the second connector body, wherein the pivot socket is configured to receive the pivot ball to allow multi-planar angulation between the first and second connector bodies; and a locking mechanism to inhibit angulation of the pivot mechanism, the locking mechanism comprising: an expansion slot in the pivot ball to split the pivot ball into deflectable portions; and a fastener configured to be threaded into the first connector body to push the deflectable portions apart.

In Example 42, the subject matter of Example 41 optionally includes wherein the fastener comprises a closure device for engaging the first closure bore to secure a stabilization member in the first rod slot.

In Example 43, the subject matter of Example 42 optionally includes wherein the expansion slot extends into the first connector body to intersect the first rod slot.

In Example 44, the subject matter of Example 43 optionally includes wherein the expansion slot extends across a surface of the first connector body into which the first rod slot extends.

In Example 45, the subject matter of any one or more of Examples 43-44 optionally include wherein the expansion slot extends across a surface of the first connector body from which the pivot ball extends.

In Example 46, the subject matter of Example 45 optionally includes wherein the first connector body comprises two closure bores to receive two closure devices that can both expand the pivot ball.

In Example 47, the subject matter of any one or more of Examples 41-46 optionally include wherein the fastener comprises a set screw extending into the pivot ball.

In Example 48, the subject matter of Example 47 optionally includes wherein the expansion slot extends through the pivot ball and into the first connector body.

In Example 49, the subject matter of any one or more of Examples 41-48 optionally include wherein the first connector body comprises a side surface from which the pivot ball extends, wherein the side surface is convex to allow the second connector body to pivot relative to the first connector body.

In Example 50, the subject matter of any one or more of Examples 41-49 optionally include wherein the first connector body comprises a side surface from which the pivot ball extends, wherein the pivot ball is offset from a center of the side surface.

Example 51 is a method of connecting stabilization members in a spinal procedure, the method comprising: connecting a first connector body to a first stabilization member; connecting a second connector body to a second stabilization member; adjusting a ball and socket pivot mechanism connecting the first connector body and the second connector body to adjust a multi-angular position between the first stabilization member and the second stabilization member; and expanding a ball of the ball and socket pivot mechanism within a socket of the ball and socket pivot mechanism to lock the ball and socket pivot mechanism.

In Example 52, the subject matter of Example 51 optionally includes wherein expanding a ball of the ball and socket pivot mechanism within a socket of the ball and socket pivot mechanism to lock the ball and socket pivot mechanism comprises: adjusting a set screw to push a first portion of the ball away from a second portion of the ball.

In Example 53, the subject matter of any one or more of Examples 51-52 optionally include wherein expanding a ball of the ball and socket pivot mechanism within a socket of the ball and socket pivot mechanism to lock the ball and socket pivot mechanism comprises: adjusting a closure device to simultaneously push a first portion of the ball away from a second portion of the ball and lock the first stabilization member in the first connector body.

In Example 54, the subject matter of Example 53 optionally includes expanding a portion of the first connector body via pushing of the closure device on the first stabilization member.

In additional Examples, any one or more of the above aspects/embodiments as substantially disclosed herein.

In additional Examples, any one or more of the aspects/embodiments as substantially disclosed herein optionally in combination with any one or more other aspects/embodiments as substantially disclosed herein.

In additional Examples, one or means adapted to perform any one or more of the above aspects/embodiments as substantially disclosed herein.

In additional Examples, any one or more of the features disclosed herein.

In additional Examples, any one or more of the features as substantially disclosed herein.

In additional Examples, any one or more of the features as substantially disclosed herein in combination with any one or more other features as substantially disclosed herein.

In additional Examples, any one of the aspects/features/embodiments in combination with any one or more other aspects/features/embodiments.

In additional Examples, use of any one or more of the aspects or features as disclosed herein.

It is to be appreciated that any feature described herein can be claimed in combination with any other feature(s) as described herein, regardless of whether the features come from the same described embodiment.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, examples are also contemplated in which only those elements shown or described are provided. Moreover, examples are also contemplated using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. The transitional phrase "consisting of" excludes any element, step, or ingredient not specified in the claim, but does not exclude additional components or steps that are unrelated to the disclosure such as impurities ordinarily associated therewith. The transitional phrase "consisting essentially of" limits the scope of a claim to the specified materials or steps and those that do not materially affect the basic and novel characteristic(s) of the claimed invention. Moreover, in the following claims, the terms "first," "second," and "third," etc. are used merely as labels, and are not intended to impose numerical requirements on their objects.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B, and C together. When each one of A, B, and C in the above expressions refers to an element, such as X, Y, and Z, or a class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The above description is intended to be illustrative, and not restrictive. For example, the above-described examples (or one or more aspects thereof) may be used in combination with each other. Other embodiments can be used, such as by one of ordinary skill in the art upon reviewing the above description. A number of variations and modifications of the disclosure can be used. It would be possible to provide for some features of the disclosure without providing others. In addition, it would be possible to combine some features of the disclosure without combining all.

References in the specification to "being operable" or "is operable" may be understood as "being configured to" or "is configured to," "being capable of" or "is capable of," and the like.

References in the specification to "one embodiment," "an embodiment," "an example embodiment," "some embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in conjunction with one embodiment, it is submitted that the description of such feature, structure, or characteristic may apply to any other embodiment unless so stated and/or except as will be readily apparent to one skilled in the art from the description. The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

The terms "determine," "calculate," "compute," and variations thereof, as used herein, are used interchangeably, and include any type of methodology, process, mathematical operation, or technique.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and this disclosure.

Unless otherwise indicated, all numbers expressing quantities, dimensions, conditions, ratios, ranges, and so forth used in the specification and claims are to be understood as being modified in all instances by the term "about" or "approximately." Accordingly, unless otherwise indicated, all numbers expressing quantities, dimensions, conditions, ratios, ranges, and so forth used in the specification and claims may be increased or decreased by approximately 5% to achieve satisfactory results. Additionally, where the meaning of the terms "about" or "approximately" as used herein would not otherwise be apparent to one of ordinary skill in the art, the terms "about" and "approximately" should be interpreted as meaning within plus or minus 5% of the stated value.

All ranges described herein may be reduced to any sub-range or portion of the range, or to any value within the range without deviating from the invention. For example, the range "5 to 55" includes, but is not limited to, the sub-ranges "5 to 20" as well as "17 to 54."

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A pivoting rod connector for spinal stabilization members, the pivoting rod connector comprising:
   a first connector block comprising:
     a first rod slot for receiving a first stabilization member; and
     a first closure bore for receiving a first closure device, wherein engaging the first stabilization member with the first closure device when the first stabilization member is inserted into the first rod slot secures the first stabilization member within the first rod slot;
   a second connector block comprising:
     a second rod slot for receiving a second stabilization member; and
     a second closure bore for receiving a second closure device, wherein the second closure device engages the second stabilization member when the second stabilization member is inserted into the second rod slot and applies a force to the second stabilization member that secures the second stabilization member within the second rod slot; and
   a pivot mechanism connecting the first connector block and the second connector block, wherein the pivot mechanism is configured to allow for angulation between the first rod slot and the second rod slot, wherein the pivoting rod connector is lockable to inhibit angulation of the pivot mechanism, and wherein the pivot mechanism comprises:
     a pivot pin integrally formed with and extending from a first side surface of the first connector block; and
     a pivot socket positioned within a second side surface of the second connector block and configured to exit into the second rod slot,
     wherein the pivot socket is shaped to allow the pivot pin of the first connector block to be inserted into or uncoupled from the pivot socket of the second connector block when the pivoting rod connector is in a first orientation about an axis of rotation through the pivot pin,
     wherein, when the pivot pin is inserted into the pivot socket, the first connector block interlocks with the second connector block when the pivoting rod connector is in a second, different orientation about the axis of rotation through the pivot pin, and
     wherein, when the pivot pin is inserted into the pivot socket, the force applied by the second closure device on the second stabilization member pushes the second stabilization member against the pivot pin such that a surface of the second stabilization member contacts a surface of the pivot pin to inhibit angulation between the first rod slot and the second rod slot.

2. The pivoting rod connector of claim 1, wherein the second rod slot comprises a surface that is angled to direct the second stabilization member toward the pivot pin as the second closure device engages the second stabilization member when the second stabilization member is inserted into the second rod slot to wedge the pivot pin within the second rod slot as a locking mechanism.

3. The pivoting rod connector of claim 2, wherein the pivot pin comprises protruding lobes and the pivot socket comprises mating recessed lobes,
   wherein the protruding lobes on the first connector block and the recessed lobes on the second connector block allow the first connector block to be uncoupled from the second connector block when the pivoting rod connector is in a first orientation, and
   wherein the protruding lobes on the first connector block and the recessed lobes on the second connector block cause the first connector block to interlock with the second connector block when the pivoting rod connector is in a second, different orientation.

4. The pivoting rod connector of claim 1, wherein the pivot mechanism comprises:
   a threaded pivot pin configured to engage a first bore in the first connector block; and
   a second bore in the second connector block,
   wherein engaging the first stabilization member with the first closure device when the first stabilization member is inserted into the first rod slot pushes the first stabilization member inserted into the first rod slot against the threaded pivot pin when the threaded pivot pin is inserted into the first bore, and
   wherein the pushing of the first stabilization member against the threaded pivot pin inhibits angulation between the first rod slot and the second rod slot as a locking mechanism.

5. The pivoting rod connector of claim 4, wherein the threaded pivot pin comprises:
   a head configured to engage an exterior surface of the first connector block;
   a smooth portion configured to pass through the first bore and around which the first connector block is configured to rotate; and
   a threaded portion configured to engage threading within the second bore of the second connector block,
   wherein the first stabilization member engages the smooth portion of the threaded pivot pin when the threaded pivot pin is inserted into the first bore and the first closure device engages the first stabilization member when the first stabilization member is inserted into the first rod slot.

6. The pivoting rod connector of claim 1, wherein the pivot mechanism comprises:

a ball connector including a pivot ball extending from the first connector block; and a ball socket positioned on the second connector block, wherein the ball socket is configured to receive the pivot ball to allow multi-planar angulation between the first and second connector blocks.

7. The pivoting rod connector of claim 6, wherein the pivot ball includes an upper portion and a lower portion separated by an expansion slot, wherein increasing a separation distance defined by the expansion slot causes the upper portion and the lower portion to engage with the ball socket when the pivot ball is inserted into the ball socket, and wherein the engaging of the upper portion and the lower portion of the pivot ball with the ball socket inhibits angulation between the first rod slot and the second rod slot as a locking mechanism.

8. The pivoting rod connector of claim 7, wherein the ball connector further includes a neck configured to couple the pivot ball to the first connector block, wherein the neck includes a fastener bore configured to receive a fastener, wherein the fastener bore includes threading in the upper portion and the lower portion of the pivot ball, and wherein engaging the fastener bore with the fastener increases the separation distance defined by the expansion slot to inhibit angulation between the first rod slot and the second rod slot as the locking mechanism.

9. The pivoting rod connector of claim 7, wherein the expansion slot extends into the first connector block and intersects with the first closure bore, and wherein engaging the first closure bore with the first closure device increases the separation distance defined by the expansion slot to inhibit angulation between the first rod slot and the second rod slot as the locking mechanism.

10. The pivoting rod connector of claim 1, wherein the pivot mechanism comprises:

a pivot pin;

at least one bore on the first connector block that is operable to receive the pivot pin; and a flexible hinge arm on the second connector block that is operable to receive a pivot pin, wherein engaging the pivot pin with the flexible hinge arm inhibits angulation between the first rod slot and the second rod slot as a locking mechanism.

11. The pivoting rod connector of claim 10, wherein the flexible hinge arm includes a fastener bore configured to receive a fastener, wherein engaging the fastener bore with the fastener causes the flexible hinge arm to engage the pivot pin to inhibit angulation between the first rod slot and the second rod slot as the locking mechanism.

12. The pivoting rod connector of claim 1, wherein at least one of the first connector block and the second connector block includes one or more slots on a side surface that are usable for adjustment of at least one of the first connector block relative to the first stabilization member when the first stabilization member is inserted into the first rod slot and the second connector block relative to the second stabilization member when the second stabilization member is inserted into the second rod slot, and when at least one of the first stabilization member and the second stabilization member are fixed in position to a spine of a patient.

13. A method of connecting stabilization members in a spinal procedure, the method comprising:

securing a first stabilization member in a first connector block of a pivoting rod connector by engaging the first stabilization member inserted in a first rod slot of the first connector block with a first closure device inserted in a first closure bore of the first connector block;

securing a second stabilization member to a second connector block of the pivoting rod connector by engaging the second stabilization member inserted in a second rod slot of the second connector block with a second closure device inserted in a second closure bore of the second connector block, wherein the second closure device applies a force to the second stabilization member;

adjusting a pivot mechanism of the pivoting rod connector connecting the first connector block and the second connector block to adjust an angular position between the first stabilization member and the second stabilization member, wherein the pivot mechanism comprises:

a pivot pin integrally formed with and extending from a first side surface of the first connector block; and a pivot socket positioned within a second side surface of the second connector block and configured to exit into the second rod slot, wherein the pivot socket is shaped to allow the pivot pin of the first connector block to be inserted into or uncoupled from the pivot socket of the second connector block when the pivoting rod connector is in a first orientation; and locking the pivot mechanism to inhibit angulation between the first stabilization member and the second stabilization member following the inserting the pivot pin of the first connector block into the pivot socket of the second connector block, wherein pivot pin of the first connector block interlocks with the pivot socket of the second connector block when the pivoting rod connector is in a second, different orientation, and wherein the pivot pin is in direct contact with the second stabilization member such that a surface of the second stabilization member contacts a surface of the pivot pin when the pivoting rod connector is in the second, different orientation following the applying of the force by the second closure device on the second stabilization member to push the second stabilization member against the pivot pin.

14. The method of claim 13, wherein the locking the pivot mechanism to inhibit angulation between the first stabilization member and the second stabilization member comprises:

engaging a wall of the second connector block and the pivot pin with the second stabilization member, wherein the wall directs the second stabilization member toward the pivot pin following engagement of the second stabilization member with the second closure device to wedge the pivot pin within the second rod slot as a locking mechanism.

15. The method of claim 13, wherein the locking the pivot mechanism to inhibit angulation between the first stabilization member and the second stabilization member comprises:

inserting a pivot pin into a first bore in the first connector block and a second bore in the second connector block, wherein the pivot pin, the first bore, and the second bore form the pivot mechanism; and engaging a pivot pin with the first stabilization member following engagement of the first stabilization member with the first closure device.

16. The method of claim 13, wherein the locking the pivot mechanism to inhibit angulation between the first stabilization member and the second stabilization member comprises:

inserting a pivot ball of a ball connector of the first connector block into a ball socket in the second connector block, wherein the ball connector and the ball socket form the pivot mechanism; and engaging the ball socket with the pivot ball by increasing a separation distance defined by an expansion slot between an upper portion and a lower portion of the pivot ball.

17. The method of claim 16, wherein the separation distance defined by the expansion slot between the upper portion and the lower portion of the pivot ball is increased by either:

engaging a fastener bore in a neck of the ball connector with a fastener to increase the separation distance defined by the expansion slot between the upper portion and the lower portion of the pivot ball, or engaging the first closure bore with the first closure device to increase the separation distance defined by the expansion slot between the upper portion and the lower portion of the pivot ball, where the expansion slot extends into the first connector block and intersects the first closure bore.

18. The method of claim 13, wherein the locking the pivot mechanism to inhibit angulation between the first stabilization member and the second stabilization member comprises:

inserting a pivot pin into at least one bore in the first connector block and a flexible hinge arm on the second connector block, wherein the pivot pin, the at least one bore, and the flexible hinge arm form the pivot mechanism; and engaging the pivot pin with the flexible hinge arm.

19. The method of claim 13, further comprising:

disengaging at least one of the first connector block from the first stabilization member and the second connector block from the second stabilization member when the pivoting rod connector is in a first position;

adjusting the positioning of at least one of the first connector block relative to the first stabilization member and the second connector block relative to the second stabilization member; and re-engaging the at least one of the first connector block to the first stabilization member and the second connector block to the second stabilization member when the pivoting rod connector is in a second, different position, wherein the disengaging, adjusting, and re-engaging occurs when at least one of the first stabilization member and the second stabilization member are fixed in position to a spine of a patient.

20. A spine stabilization system, the system comprising:
a first stabilization member;
a second stabilization member; and
a pivoting rod connector, the pivoting rod connector comprising:
a first connector block comprising:

a first rod slot for receiving a first end of the first stabilization member; and a first closure bore for receiving a first closure device, wherein engaging the first end of the first stabilization member with the first closure device secures the first stabilization member within the first rod slot;

a second connector block comprising:

a second rod slot for receiving a second end of a second stabilization member; and a second closure bore for receiving a second closure device, wherein the second closure device engages the second end of the second stabilization member and applies a force to the second stabilization member that secures the second stabilization member within the second rod slot; and a pivot mechanism connecting the first connector block and the second connector block, wherein the pivot mechanism is configured to allow for angulation between the first rod slot and the second rod slot, and wherein the pivoting rod connector is lockable to inhibit angulation of the pivot mechanism, and wherein the pivot mechanism comprises:

a pivot pin including protruding lobes, wherein the pivot pin is integrally formed with and extending from a first side surface of the first connector block; and a pivot socket including recessed lobes, wherein the pivot socket is cut into a second side surface of the second connector block and configured to exit into the second rod slot, wherein the protruding lobes on the first connector block and the recessed lobes on the second connector block allow the first connector block to be inserted into or uncoupled from the second connector block when the pivoting rod connector is in a first orientation, wherein the protruding lobes on the first connector block and the recessed lobes on the second connector block cause the first connector block to interlock with the second connector block when the pivoting rod connector is in a second, different orientation, and wherein, when the pivot pin is inserted into the pivot socket, the force applied by the second closure device on the second stabilization member pushes the second stabilization member against the pivot pin such that a surface of the second stabilization member contacts a surface of the pivot pin to inhibit angulation between the first rod slot and the second rod slot as a locking mechanism.

* * * * *